US012235272B2

(12) United States Patent
McDevitt et al.

(10) Patent No.: US 12,235,272 B2
(45) Date of Patent: Feb. 25, 2025

(54) SCREENING AND ASSESSMENT OF POTENTIALLY MALIGNANT ORAL LESIONS

(71) Applicant: NEW YORK UNIVERSITY, New York, NY (US)

(72) Inventors: John T. McDevitt, New York, NY (US); Michael P. McRae, Houston, TX (US)

(73) Assignee: New York University, New York, NY (US)

( * ) Notice: Subject to any disclaimer, the term of this patent is extended or adjusted under 35 U.S.C. 154(b) by 477 days.

(21) Appl. No.: 17/147,681

(22) Filed: Jan. 13, 2021

(65) Prior Publication Data

US 2021/0215703 A1  Jul. 15, 2021

Related U.S. Application Data

(60) Provisional application No. 62/960,297, filed on Jan. 13, 2020.

(51) Int. Cl.
| G01N 33/574 | (2006.01) |
| G16H 10/40 | (2018.01) |
| G16H 10/60 | (2018.01) |
| G16H 50/20 | (2018.01) |

(52) U.S. Cl.
CPC ....... G01N 33/57492 (2013.01); G16H 10/40 (2018.01); G16H 10/60 (2018.01); G16H 50/20 (2018.01)

(58) Field of Classification Search
CPC .................. G01N 33/57492; G01N 33/57407
See application file for complete search history.

(56) References Cited

U.S. PATENT DOCUMENTS

| 5,733,721 A | 3/1998 | Hemstreet, III |
| 5,740,270 A | 4/1998 | Rutenberg |
| 7,781,226 B2 | 8/2010 | McDevitt |
| 8,101,431 B2 | 1/2012 | McDevitt |
| 8,105,849 B2 | 1/2012 | McDevitt |
| 8,257,967 B2 | 9/2012 | McDevitt |
| 8,377,398 B2 | 2/2013 | McDevitt |
| 2002/0012938 A1 | 1/2002 | Rutenberg |
| 2006/0073585 A1 | 4/2006 | McDevitt |
| 2006/0079000 A1 | 4/2006 | Floriano |
| 2006/0234209 A1 | 10/2006 | Walker |
| 2006/0257854 A1 | 11/2006 | McDevitt |
| 2006/0257941 A1 | 11/2006 | McDevitt |
| 2006/0257991 A1 | 11/2006 | McDevitt |
| 2008/0038738 A1 | 2/2008 | Weigum |
| 2008/0050830 A1 | 2/2008 | Floriano |
| 2008/0176253 A1 | 7/2008 | Christodoulides |
| 2008/0300798 A1 | 12/2008 | McDevitt |
| 2010/0291431 A1 | 11/2010 | Shih |
| 2012/0208715 A1 | 8/2012 | McDevitt |
| 2012/0322682 A1 | 12/2012 | McDevitt |
| 2013/0130933 A1 | 5/2013 | McDevitt |
| 2013/0274136 A1 | 10/2013 | McDevitt |
| 2013/0295580 A1* | 11/2013 | McDevitt ......... G01N 33/57407 435/6.14 |
| 2014/0080138 A1* | 3/2014 | Ralhan .............. G01N 33/6893 435/7.1 |
| 2014/0094391 A1 | 4/2014 | McDevitt |
| 2014/0235487 A1* | 8/2014 | McDevitt .............. G16H 50/30 702/19 |
| 2015/0111778 A1 | 4/2015 | McDevitt |
| 2018/0322327 A1 | 11/2018 | Smith |
| 2019/0369099 A1 | 12/2019 | McDevitt |

FOREIGN PATENT DOCUMENTS

| WO | WO199201330 | 8/1992 |
| WO | 03090605 | 11/2003 |
| WO | 2004009840 | 1/2004 |
| WO | 2004072097 | 8/2004 |
| WO | 2005083423 | 9/2005 |
| WO | 2005085796 | 9/2005 |
| WO | 2005085854 | 9/2005 |
| WO | 2005085855 | 9/2005 |
| WO | 2005090983 | 11/2005 |
| WO | 2007053186 | 7/2007 |
| WO | 2007134191 | 11/2007 |
| WO | 2007134189 | 7/2008 |
| WO | 2008131039 | 1/2009 |
| WO | 2007002480 | 3/2009 |
| WO | 2011022628 | 2/2011 |
| WO | 2012021714 | 4/2012 |
| WO | 2012065025 | 7/2012 |
| WO | 2012154306 | 11/2012 |
| WO | 2012065117 | 4/2014 |

OTHER PUBLICATIONS

Kelpsch et al., Anatomical Rec, 301:1999-2013, 2018.*
Abram TJ et al., Oral oncology. Sep. 1, 2016;60:103-11.
Abram TJ et al., Oral oncology. May 1, 2019;92:6-11.
Abram TJ et al., Translational oncology. Apr. 1, 2018; 11(2):477-86.
Bosman FT, The Journal of Pathology: A Journal of the Pathological Society of Great Britain and Ireland. Jun. 2001; 194(2):143-4.
Bouquot JE et al., The Journal of the American Dental Association. Jan. 1, 1986;112(1):50-7.
Brands MT et al., Cancer medicine. Sep. 1, 2019.
Carpenter AE et al., Genome biology. Apr. 2006;7(10):R100.
CDx Diagnostics: The Painless Test for Common Oral Spots https://www.cdxdiagnostics.com/brushtest/. Accessed May 10, 2019.
Daniel FI et al., Applied Cancer Research. 2010;30(3):279-88.
De Jong K, Nio CY, Hermans JJ, et al. High prevalence of pancreatic cysts detected by screening magnetic resonance imaging examinations. Clin Gastroenterol Hepatol. 2010;8(9):806-811.

(Continued)

*Primary Examiner* — Mark Halvorson
(74) *Attorney, Agent, or Firm* — Riverside Law LLP

(57) ABSTRACT

The present disclosure is related to systems and methods to be used as aids in the diagnosis of risk for oral cancer, potentially malignant oral lesion (PMOL), and/or oral epithelial dysplasia (OED) by identifying cellular phenotype characteristics of cell samples, including percentage of mature squamous cells, presence or absence of nuclear actin in mature squamous cells, percentage of non-mature squamous cells, percentage of small round cells, percentage of white blood cells, and percentage of lone nuclei.

12 Claims, 30 Drawing Sheets

(56) References Cited

OTHER PUBLICATIONS

El-Naggar AK et al., WHO classification of tumours of the head and neck. 4th ed. Lyon: IARC Press; 2017.
Fife, C M et al. "Movers and shakers: cell cytoskeleton in cancer metastasis." British journal of pharmacology vol. 171,24 (2014): 5507-2.
Hastie T et al., Springer Science & Business Media; Aug. 26, 2009.
Hosmer DW, Lemeshow S. Applied Logistic Regression. 2nd ed. New York: John Wiley & Sons, Inc.; 2004.
Huber MA, Dental Clinics. Jan. 1, 2018;62(1):59-75.
Jolliffe I. Principal component analysis. 2nd ed. New York: Springer; 2011.
Krishna, Akhilesh, et al. "Demographic risk factors, affected anatomical sites and clinicopathological profile for oral squamous cell carcinoma in a north Indian population." Asian Pacific Journal of Cancer Prevention 15.16 (2014):6755-6760.
LaValley MP, Circulation. May 6, 2008;117(18):2395-9.
Lee JJ et al., Oral Surgery, Oral Medicine, Oral Pathology, Oral Radiology, and Endodontology. Aug. 1, 2007;104 (2):217-25.
Li Hx et al., Journal of Oral Pathology & Medicine. Aug. 2013;42(7):547-56.
Lingen MW et al., The Journal of the American Dental Association. Nov. 1, 2017;148(11):797-813.
Lingen MW et al., The Journal of the American Dental Association. Oct. 1, 2017; 148(10):712-27.
Lugli E et al., Cytometry Part A: The Journal of the International Society for Analytical Cytology. May 2007;71(5):334-44.
McDevitt J et al., Spie newsroom. Mar. 28, 2011.
McRae MP et al., Cancer cytopathology. Mar. 2020;128(3):207-20.
McRae MP et al., Journal of dental research. Nov. 12, 2020:0022034520973162,.
Miroshnikova YA, Nava MM, Wickström SA. Emerging roles of mechanical forces in chromatin regulation. J Cell Sci. 2017;130(14):2243-225.
Moore HM, Vartiainen MK. F-actin organizes the nucleus. Nat Cell Biol. 2017;19(12):1386-1388.
National Cancer Institute Surveillance, Epidemiology, and End Results Program. Cancer stat facts: oral cancer and pharynx cancer. https://seer.cancer.gov/statfacts/html/oralcav.html. Accessed May 10, 2019.
Neville BW et al., Oral and maxillofacial pathology. Elsevier Health Sciences; May 13, 2015.
Office Action (Final Rejection) dated Oct. 23, 2023 for U.S. Appl. No. 16/432,324 (pp. 1-10).
Poate TW et al., Oral oncology. Sep. 1, 2004;40(8):829-34.
Rashid A et al., Journal of Oral Pathology & Medicine. May 2015;44(5):307-28.
Schneider CA et al., Nat Meth 9 (7): 671-675, 2012.
Sciubba JJ, The Journal of the American Dental Association. Oct. 1, 1999;130(10):1445-57.
Scott IS et al., British journal of cancer. Apr. 2006;94(8):1170.
Shield KD et al., CA: a cancer journal for clinicians. Jan. 2017;67(1):51-64).
Speight PM et al., Oral surgery, oral medicine, oral pathology and oral radiology. Oct. 1, 2015;120(4):474-82.
Sperandio M et al., Cancer Prevention Research. Aug. 1, 2013;6(8):822-31.
Stevenson CE, Nagahashi M, Ramachandran S, Yamada A, Bear HD, Takabe K. Bevacizumab and breast cancer: what does the future hold?. Future Oncol. 2012;8(4):403-414.
Torres-Rendon A et al., British journal of cancer. Apr. 2009;100(7):1128).
Vigneswaran N et al., Experimental and molecular pathology. Apr. 1, 2006;80(2):147-59.
Wang D et al., Statistics in medicine. Nov. 30, 2004;23(22):3451-67.
Warnakulasuriya S et al., Journal of Oral Pathology & Medicine. Mar. 2008;37(3):127-33.
Weigum SE et al., Cancer Prevention Research. Apr. 1, 2010;3(4):518-28.
Weigum SE et al., Lab on a Chip. 2007;7(8):995-1003.
Williams GH et al., Proceedings of the National Academy of Sciences. Dec. 8, 1998;95(25):14932-7.
Ylipalosaari M et al., Experimental cell research. Oct. 1, 2005;309(2):273-83.
Yu YH et al., Oral surgery, oral medicine, oral pathology and oral radiology. May 1, 2015;119(5):553-65.

\* cited by examiner

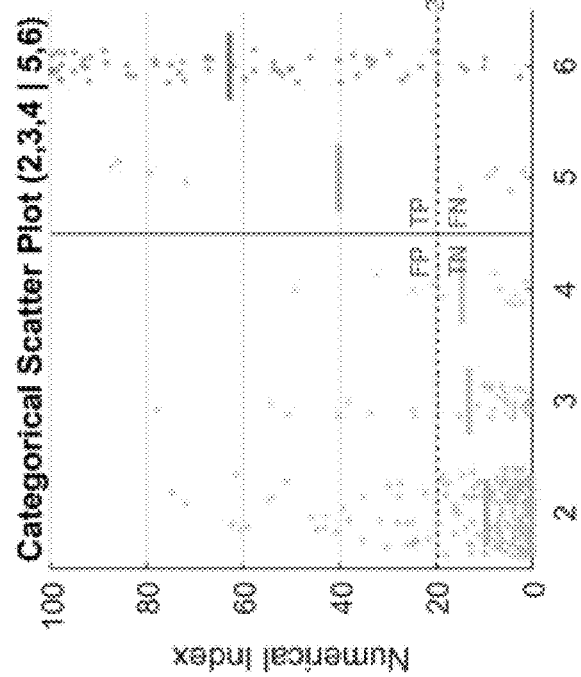
Fig. 25A
Fig. 25B
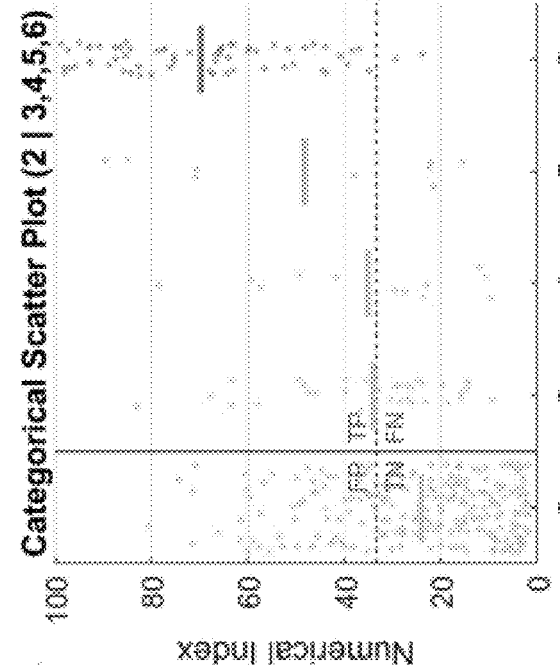
Fig. 25C
| Dichotomous Split | POCOCT Multivariate Model | | |
|---|---|---|---|
| | Sensitivity | Specificity | AUC |
| 2 \| 3,4,5,6 | 0.72 (0.67-0.76) | 0.73 (0.69-0.78) | 0.82 (0.77-0.87) |
| 2,3 \| 4,5,6 | 0.79 (0.74-0.83) | 0.85 (0.81-0.89) | 0.89 (0.84-0.93) |
| 2,3,4L \| 4H,5,6 | 0.80 (0.75-0.84) | 0.82 (0.78-0.86) | 0.89 (0.84-0.93) |
| 2,3,4 \| 5,6 | 0.86 (0.82-0.90) | 0.84 (0.80-0.88) | 0.93 (0.88-0.97) |
| 2 vs. 6 | 0.89 (0.85-0.92) | 0.90 (0.85-0.93) | 0.95 (0.91-0.98) |
| 1 vs. 6 | 0.94 (0.89-0.97) | 0.92 (0.87-0.95) | 0.97 (0.94-1.00) |

SCREENING AND ASSESSMENT OF POTENTIALLY MALIGNANT ORAL LESIONS

CROSS-REFERENCE TO RELATED APPLICATIONS

This application claims priority to U.S. Provisional Patent Application No. 62/960,297, filed Jan. 13, 2020, the contents of which are incorporated by reference herein in its entirety.

STATEMENT REGARDING FEDERALLY SPONSORED RESEARCH OR DEVELOPMENT

This invention was made with government support under Grant Nos. 1RC2DE020785-01, 5RC2DE020785-02, 3RC2DE020785-02S1, 3RC2DE020785-02S2, and R01 DE024392 awarded by the National Institutes of Health (NIH). The government has certain rights in the invention.

BACKGROUND OF THE INVENTION

Cancers of the lip, oral cavity, and pharyngeal subsites are estimated to affect over 500,000 people globally each year (Shield K D et al., CA: a cancer journal for clinicians. 2017 January; 67(1):51-64). The National Cancer Institute's Surveillance, Epidemiology, and End Results (SEER) program estimates 53,000 new cases and 10,860 deaths attributed to oral and pharyngeal cancer (OPC) in 2019 in the US alone, of which approximately 50% involve oral cavity subsites. Collectively, OPCs represent approximately 3% of all cancers (National Cancer Institute Surveillance, Epidemiology, and End Results Program. Cancer stat facts: oral cancer and pharynx cancer. https://seer.cancer.gov/statfacts/html/oralcav.html. Accessed May 10, 2019). Approximately two-thirds of OPCs are diagnosed at Stage III or IV when the 5-year survival rate is just 45% and 32%, respectively (Neville B W et al., Oral and maxillofacial pathology. Elsevier Health Sciences; 2015 May 13). For the remaining third of OPCs detected at early stages,[4] survival increases to 84% (National Cancer Institute Surveillance, Epidemiology, and End Results Program. Cancer stat facts: oral cancer and pharynx cancer. https://seer.cancer.gov/statfacts/html/oralcav.html. Accessed May 10, 2019). Despite steady improvements in overall survival rates for OPC over the last four decades, identifying OPCs at an early stage remains a challenge for oral health care providers (Huber M A, Dental Clinics. 2018 Jan. 1; 62(1):59-75). The current diagnostic paradigm of procuring a biopsy is based on remote lab services which can take days/weeks to provide results, and this further prolongs anxiety for patients. A point-of-care (POC) solution could provide immediate feedback within the same visit.

A successful diagnostic adjunctive test for primary care settings should be able to discriminate potentially malignant oral lesions (PMOLs) that are at "risk" (i.e., malignant lesions or those with an elevated risk for undergoing malignant transformation) from more common benign lesions with no malignant potential, thus improving the referral efficiency to secondary or tertiary care (e.g., reducing over-referral of patients with benign lesions and improving the early identification and prompt referral of malignant or high-grade dysplastic PMOLs for oncologic care). Numerous adjunctive tests are available to assist in the diagnosis of PMOLs. In a meta-analysis of oral cancer adjuncts, vital staining and visualization adjuncts (e.g., autofluorescence and tissue reflectance) demonstrated insufficient accuracy to be recommended for use as lesion triage tools by general dentists (Lingen M W et al., The Journal of the American Dental Association. 2017 Oct. 1; 148(10):712-27). Cytology, however, has demonstrated greater sensitivity and specificity relative to the other adjuncts, suggesting its potential as a surrogate for gold-standard histopathology. This evidence to support the accuracy of cytology is largely based on accuracy studies performed in secondary and tertiary care settings. Although cytology is unable to replace histopathologic diagnosis based on tissue architecture, this relatively inexpensive, easy to perform, and minimally-invasive method may be useful for triaging lesions in any setting: primary care settings such as a dental office, low-resource/remote settings, and secondary/tertiary settings. Incisional biopsy followed by histopathologic examination represents the current standard of care for diagnosing PMOLs. However, incisional biopsy of PMOLs, particularly in those that are large non-homogeneous leukoplakias, leads to underestimation of the severity of OED up to 30% of the time because the biopsy sample (typically 5 mm in diameter) may not be representative of the variable pathology across the field of the entire PMOL (Lee J J et al., Oral Surgery, Oral Medicine, Oral Pathology, Oral Radiology, and Endodontology. 2007 Aug. 1; 104(2):217-25). Brush cytology could enable a wider sampling of PMOLs that encompass larger areas or are multifocal with the potential to reduce sampling errors encountered with incisional biopsies.

Thus, there is a strong need for technology-driven solutions that can precisely and rapidly diagnose the entire spectrum of oral epithelial dysplasia (OED) and oral squamous cell carcinoma (OSCC) using minimally invasive sampling at the POC.

SUMMARY OF THE INVENTION

In one aspect, a method of assessing oral disease in a subject comprising: identifying at least one cellular phenotype of one or more cells in a sample of the subject; determining a cellular phenotype characteristic that is a percent of mature squamous cells of the sample that express nuclear actin based upon the identified cellular phenotype of the cells; and using the cellular phenotype characteristic to assess a presence or severity of oral disease in the subject.

In one embodiment, the oral disease is selected from the group consisting of: oral cancer, potentially malignant oral lesion (PMOL), and oral epithelial dysplasia (OED). In one embodiment, the percent of mature squamous cells expressing nuclear actin between 10% and 100% indicates the presence of oral disease in the subject. In one embodiment, the percent of mature squamous cells expressing nuclear actin below 10% indicates the absence of oral disease in the subject.

In one embodiment, the determining step further comprises one or more cellular phenotype characteristics selected from the group consisting of: percent of mature squamous cells, percent of non-mature squamous cells, percent of small round cells, percent of white blood cells, and percent of lone nuclei.

In one embodiment, the method further comprises determining one or more morphological characteristics from individual cells of the sample, said morphological characteristics selected from nuclear area, cell area, cell circularity, cell aspect ratio, and cell roundness; transmitting the one or more morphological characteristics to a computer; and using the cellular phenotype characteristics and morphological characteristics to assess the severity of oral disease in the subject.

In one embodiment, the method further comprises determining one or more biomarker levels in cells of the sample, said biomarker selected from the group consisting of alpha V beta 6 (AVB6), Epidermal Growth Factor Receptor (EGFR), Ki67, Geminin, Mini Chromosome Maintenance protein (MCM2), beta catenin, EMPPRIN, CD147, Cofilin, Importin 9, Profilin, thymosin-β4, Wiskott-Aldrich syndrome protein (WASp), Arp2/3 complex, and formins; transmitting the one or more biomarker levels to a computer; and using the cellular phenotype characteristics and biomarker levels to assess the severity of oral disease in the subject.

In one embodiment, the method further comprises transmitting one or more demographic data of the subject to a computer, said demographic data selected from the group consisting of gender, age, alcohol intake, and smoking status of the subject; and using the cellular phenotype characteristics and biomarker levels to assess the severity of oral disease in the subject.

In one embodiment, the method allows for the distinguishing between at least: 1) normal, 2) benign lesions, 3) mild dysplasia, 4) moderate dysplasia, 5) severe dysplasia, and 6) carcinoma in situ/malignant lesion.

In one embodiment, the method further comprises calculating a risk score based upon the cellular phenotype characteristics. In one embodiment, the method further comprises displaying the risk score on an output device. In one embodiment, said calculation is based on artificial neural nets, logistic regression, linear discriminate analysis, or random forests. In one embodiment, the method further comprises transmitting the one or more cellular phenotype characteristics to a remote processor to be assessed by a pathologist.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 3A (left) shows the four distinct cell phenotypes that were identified: Type 1 ('mature squamous cells'), Type 2 ('small round cells'), Type 3 ('leukocytes'), and Type 4 ('lone nuclei'). Principal component analysis (right) shows cell phenotypes clustered into distinct groups with substantial separation between cell phenotype labels, demonstrating strong promise for an effective cell phenotype recognition algorithm. Boxplots in FIG. 3B show the study population distributions of mature squamous cells (left), small round cells (center), and leukocytes (right), representing the predicted mean cell type percentages across six biomarker assays (αvβ6, CD-147, EGFR, geminin, Ki-67, and MCM2) within each lesion class: normal (n=121), benign (n=241), dysplasia (n=59), and malignant (n=65). The results shown include only patients with definitive lesion determinations and patients with evaluable data for all six biomarkers. FIG. 3C shows limited field of view cytology pseudocolor images (fluorescence images acquired with a monochrome camera and digitally assigned to red, green, and blue color channels) of benign (left) and malignant (right) lesions with the cell phenotype model output labels overlaid as follows: "M" for mature squamous cells, "S" for small round cells, "W" for leukocytes, and "L" for lone nuclei (Unknown type "U" not shown). Fluorescent staining shows the cytoplasm (red), nuclei (blue), and Ki-67 biomarker (green).

FIG. 4A shows the ROC curve for the model. The lasso logistic regression coefficients are provided in FIG. 4B. The predictors are as follows: "1-% TYPE 1" (percent of cells that are non-mature squamous cells), "% TYPE 2" (percent of cells that are small round cells), "% TYPE 3" (percent of cells that are leukocytes), "AGE", "SEX", "PACKYR" (pack years), "LSIZEMAX" (lesion diameter of the major axis), "LICHENFN" (clinical impression of lichen planus), and "LESIONCOLOR" (red, white, or red/white). The boxplot in FIG. 4C shows cross-validated algorithm response ("numerical index") for the lasso logistic regression on the test set averaged over all biomarker assays. Distribution of scores are represented for benign (n=241), mild dysplasia (n=38), moderate/severe dysplasia (n=21), and malignant lesions (n=65). FIG. 4D shows a model calibration plot of the predicted responses (numerical index) sorted and grouped into deciles vs. the observed proportions of dysplasia and malignant lesions.

Figure 7:
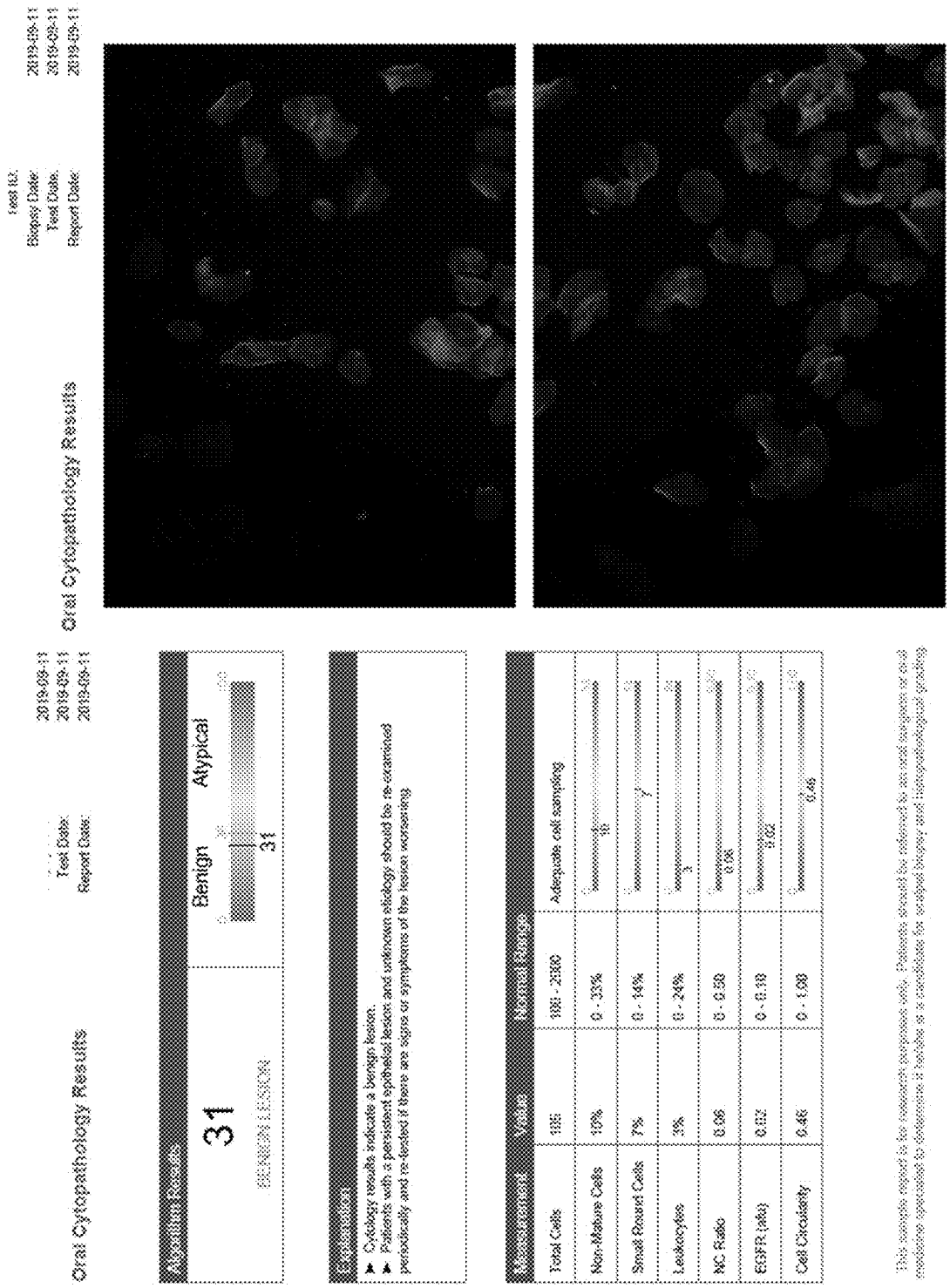

FIG. 7 depicts oral cytopathology test results. The algorithm result is a numerical index between 0 and 100 with a cutoff of 36 that distinguishes benign and dysplasia/malignant ("atypical") lesions (left). Other informative cytopathology results are displayed on a reference range, including total cell counts, cell phenotype distributions, mean values for NC ratio, molecular biomarker fluorescence intensity, and cell circularity. Images and outlines of the cells are provided for additional test context (right).

Figure 8:
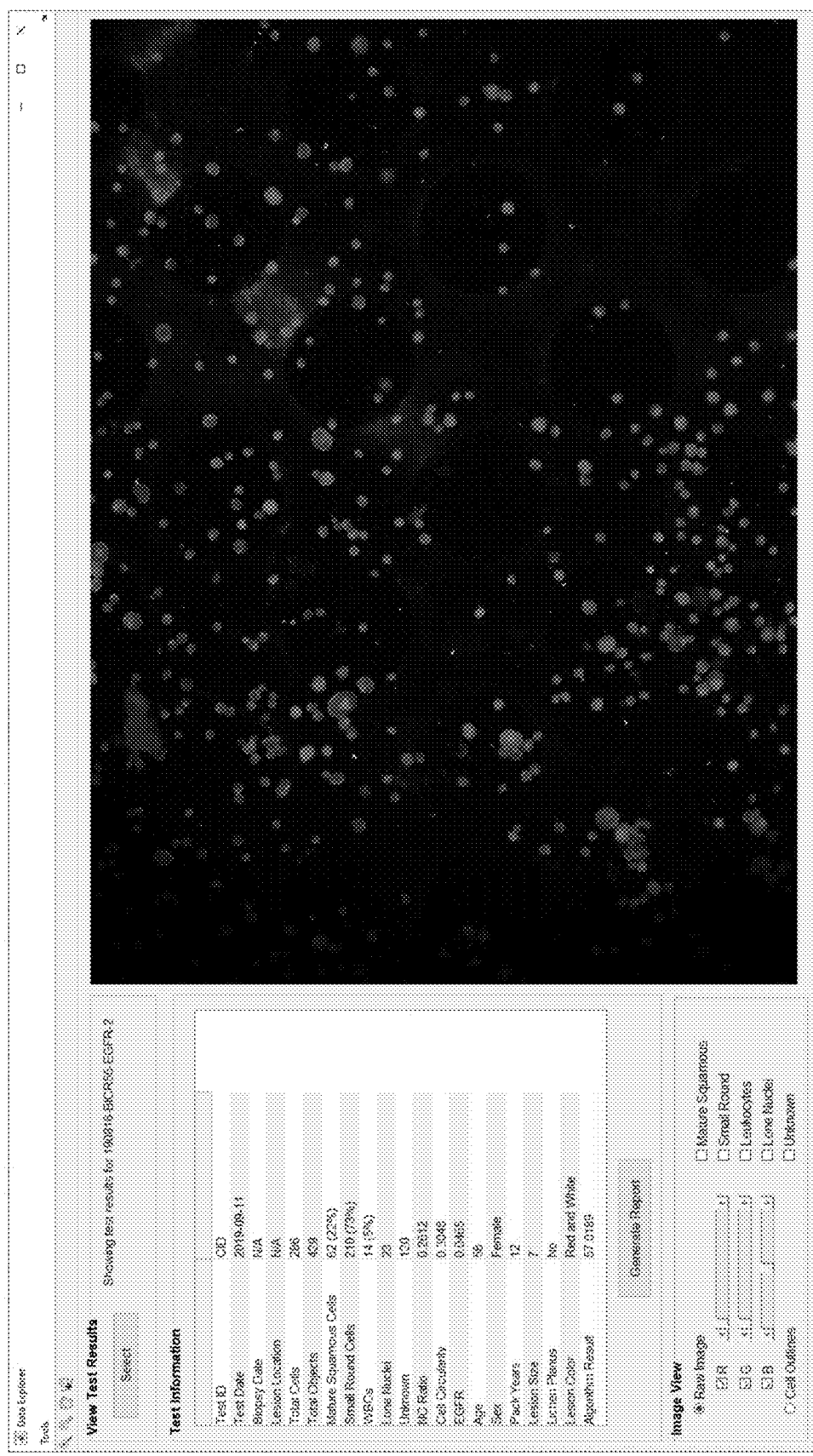

FIG. 8 depicts a screenshot of cytopathology interface showing BICR 56 cancer cells with all three fluorescent labels (red: phalloidin, green: EGFR, blue: DAPI).

Figure 9:
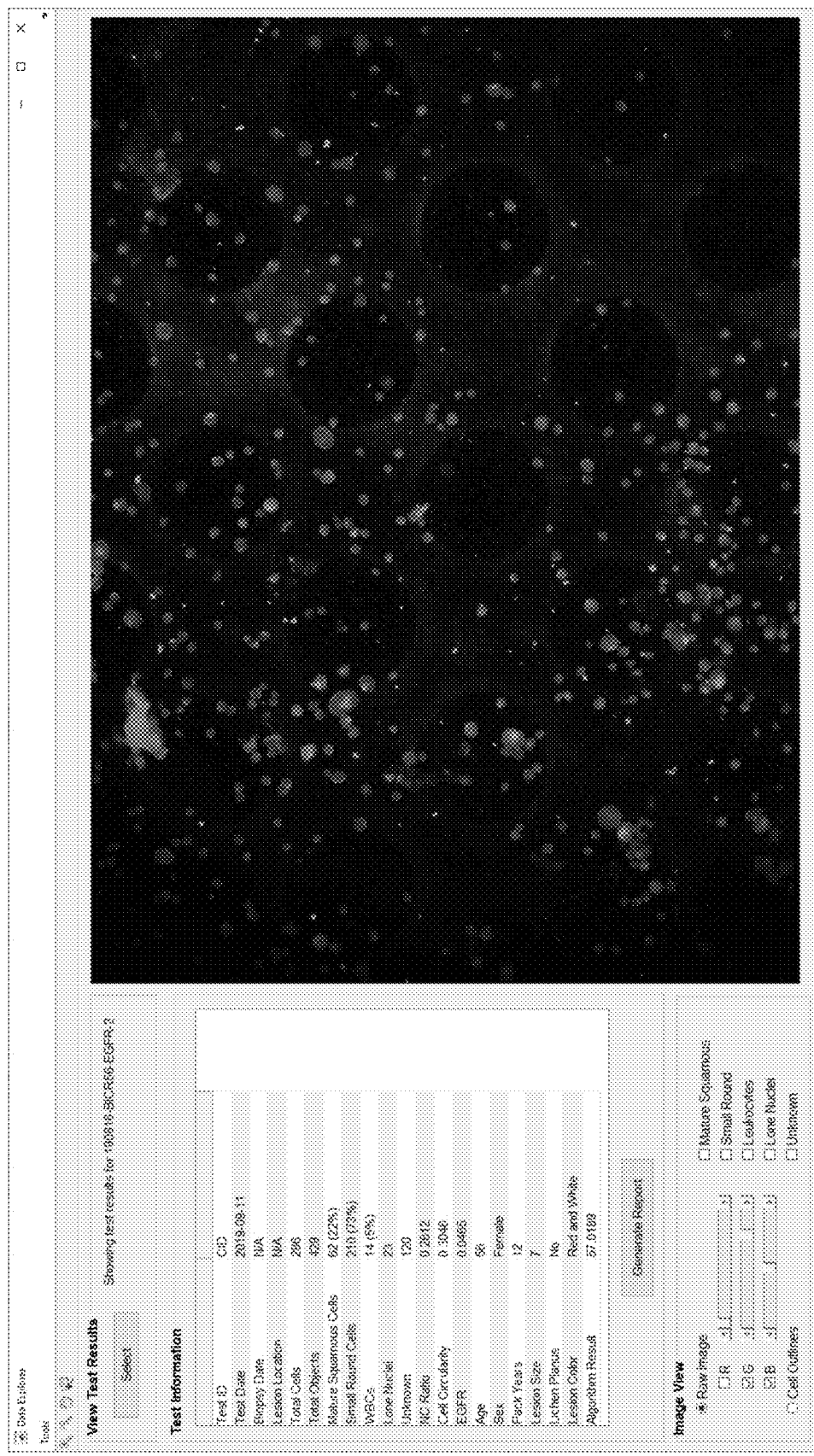

FIG. 9 depicts a screenshot of cytopathology interface showing BICR 56 cancer cells with green (EGFR) and blue (DAPI) fluorescent labels.

Figure 10:
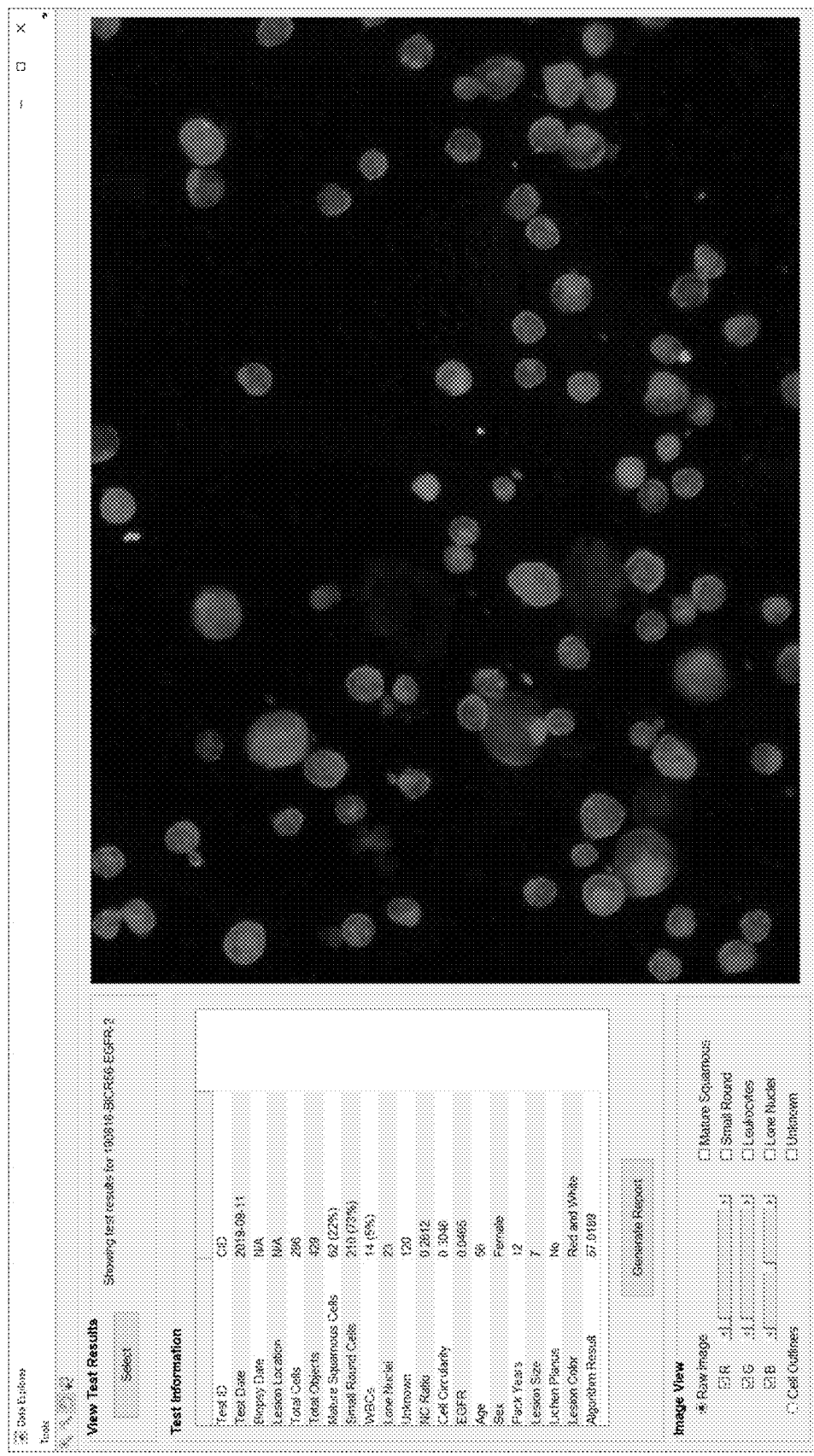

FIG. 10 depicts a screenshot of cytopathology interface showing BICR 56 cancer cells magnified view with all three fluorescent labels (red: phalloidin, green: EGFR, blue: DAPI).

Figure 11:
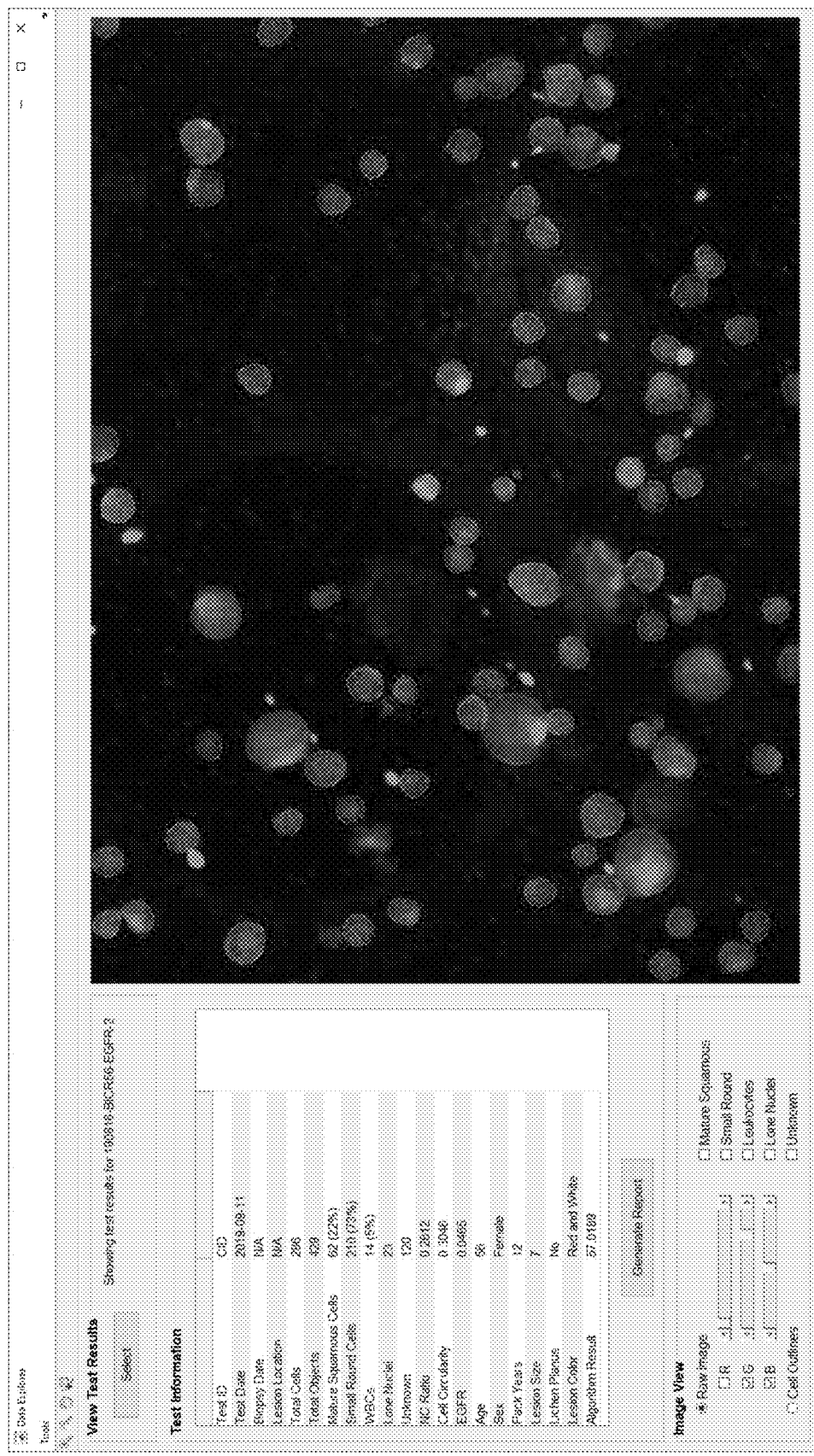

FIG. 11 depicts a screenshot of cytopathology interface showing BICR 56 cancer cells magnified view with green (EGFR) and blue (DAPI) fluorescent labels.

Figure 12:
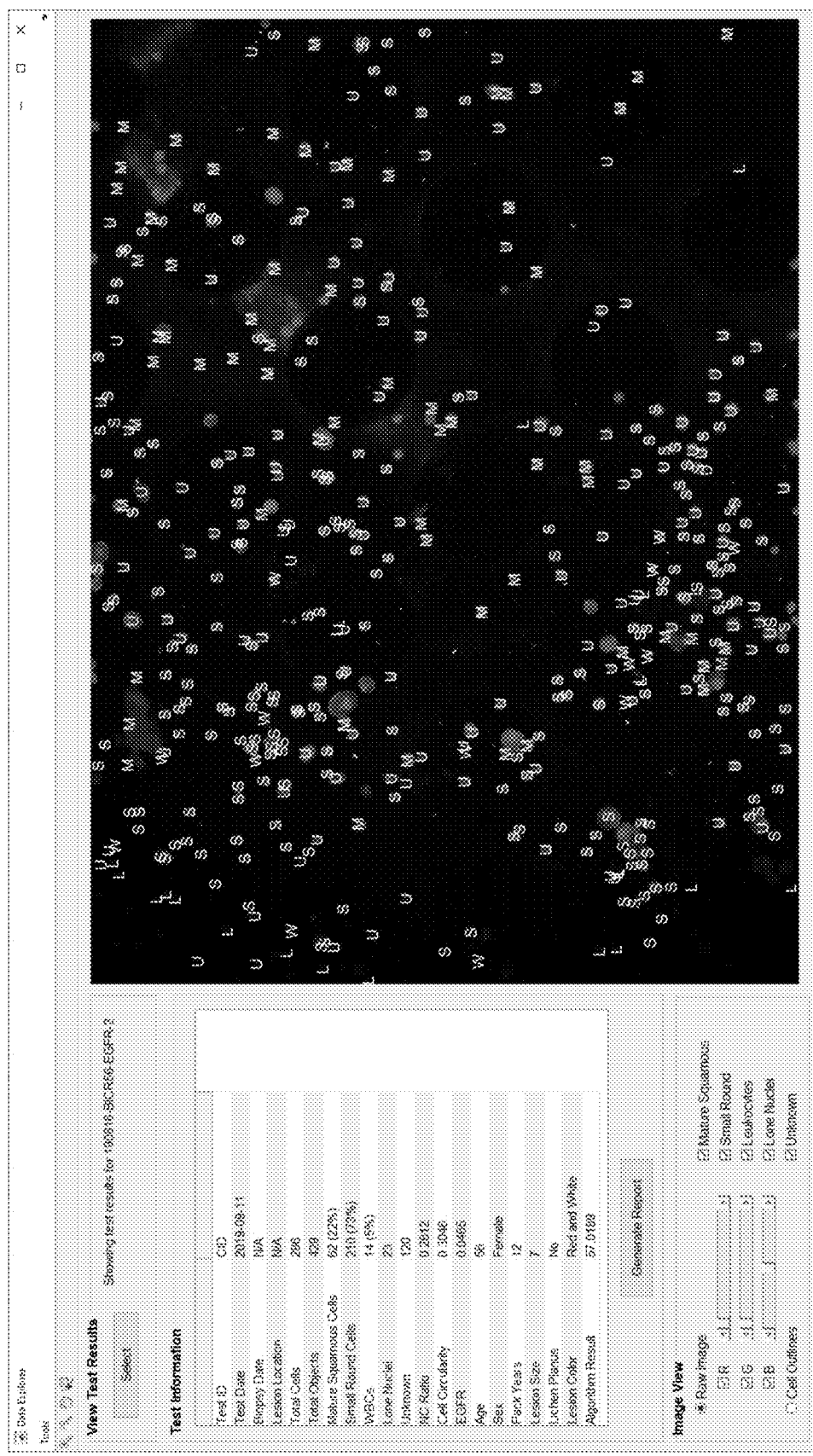

FIG. 12 depicts a screenshot of cytopathology interface showing BICR 56 cancer cells with cell phenotype labels overlaid (M: mature squamous, S: small round, W: leukocytes, L: lone nuclei, U: unknown).

Figure 13:
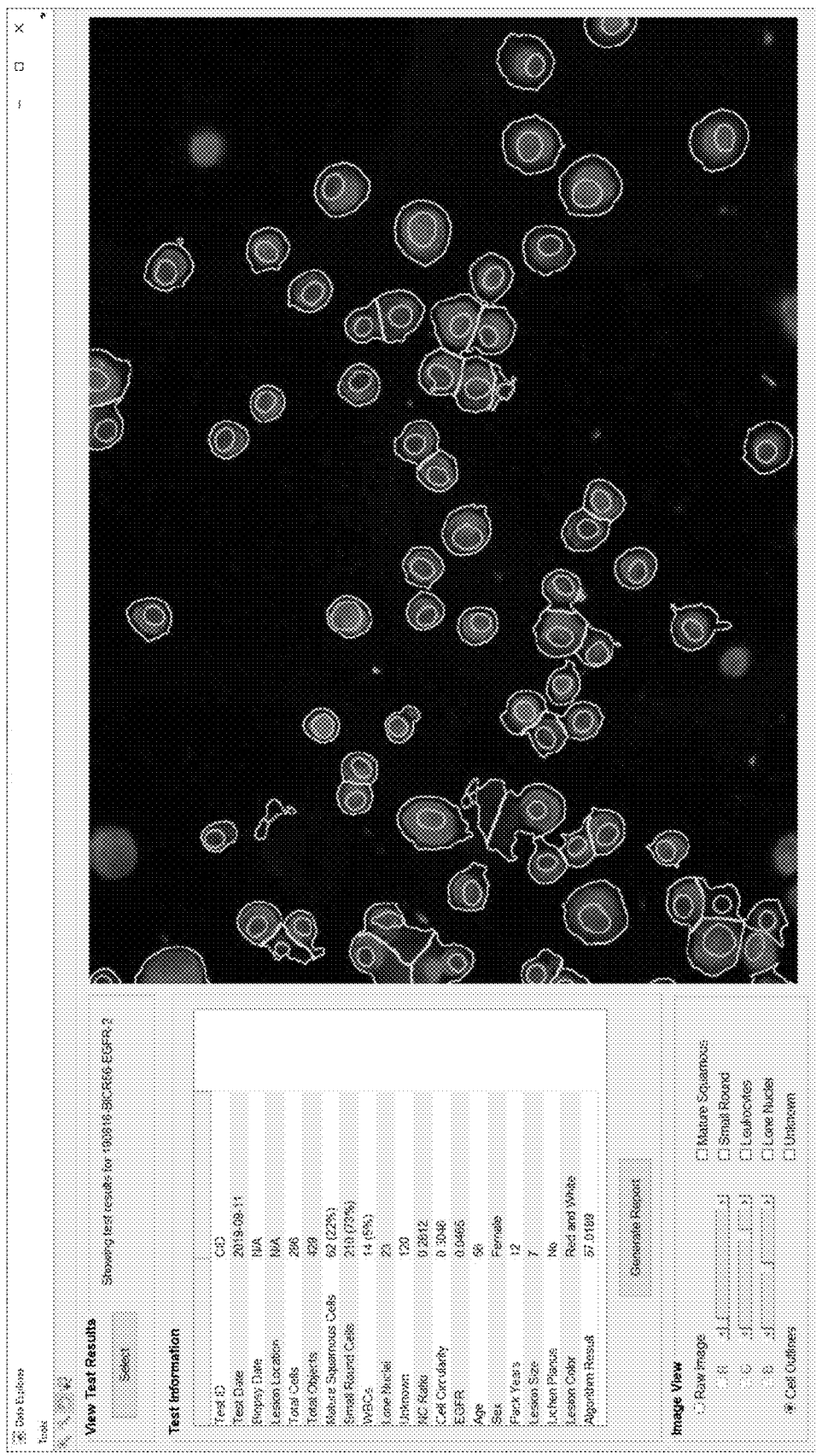

FIG. 13 depicts a screenshot of cytopathology interface showing BICR 56 cancer cells magnified view with cell outlines overlaid.

Figure 14:
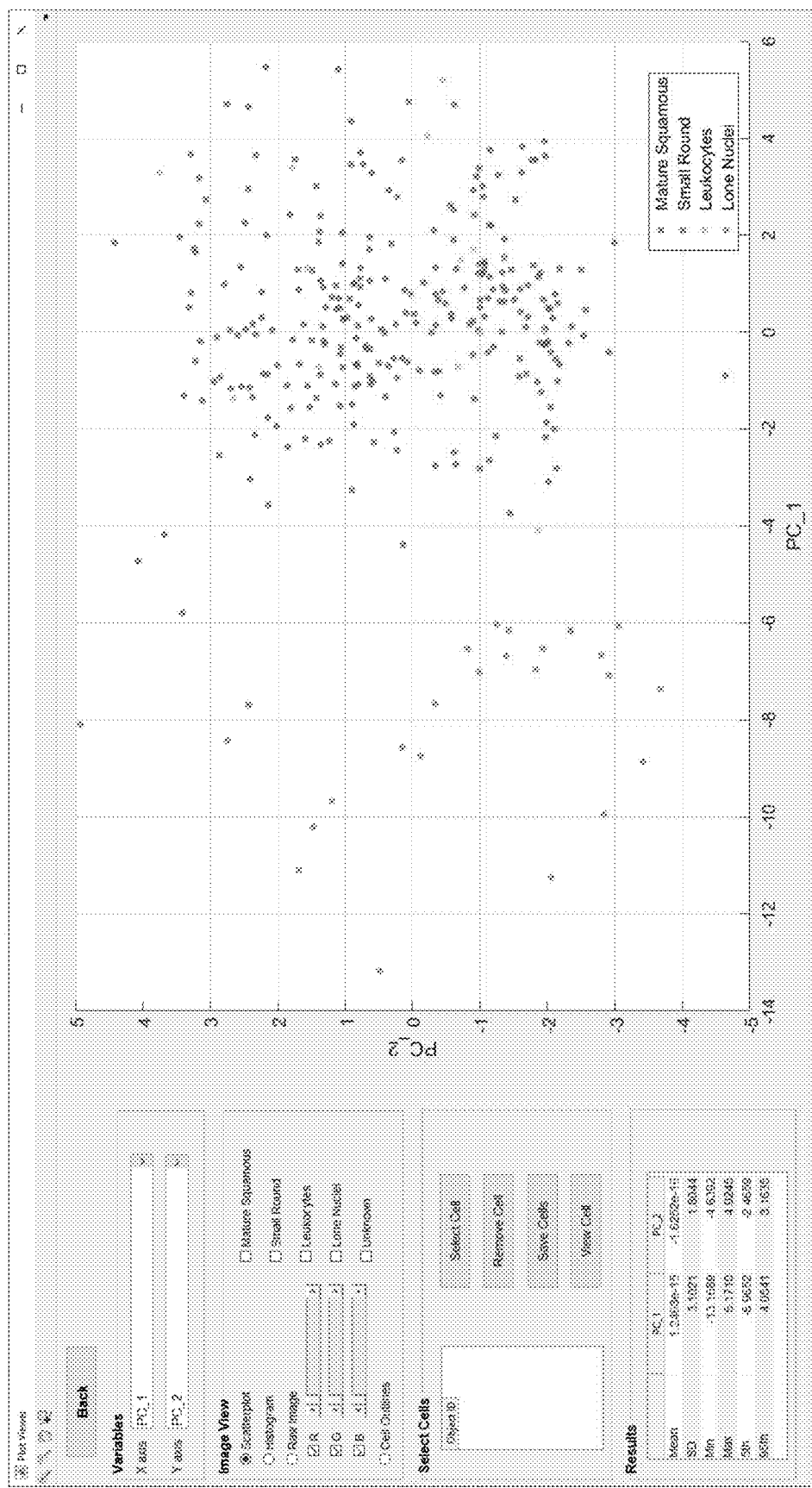

FIG. 14 depicts a screenshot of cytopathology interface showing a principal component scatter plot from a sample of BICR 56 cancer cells.

Figure 15:
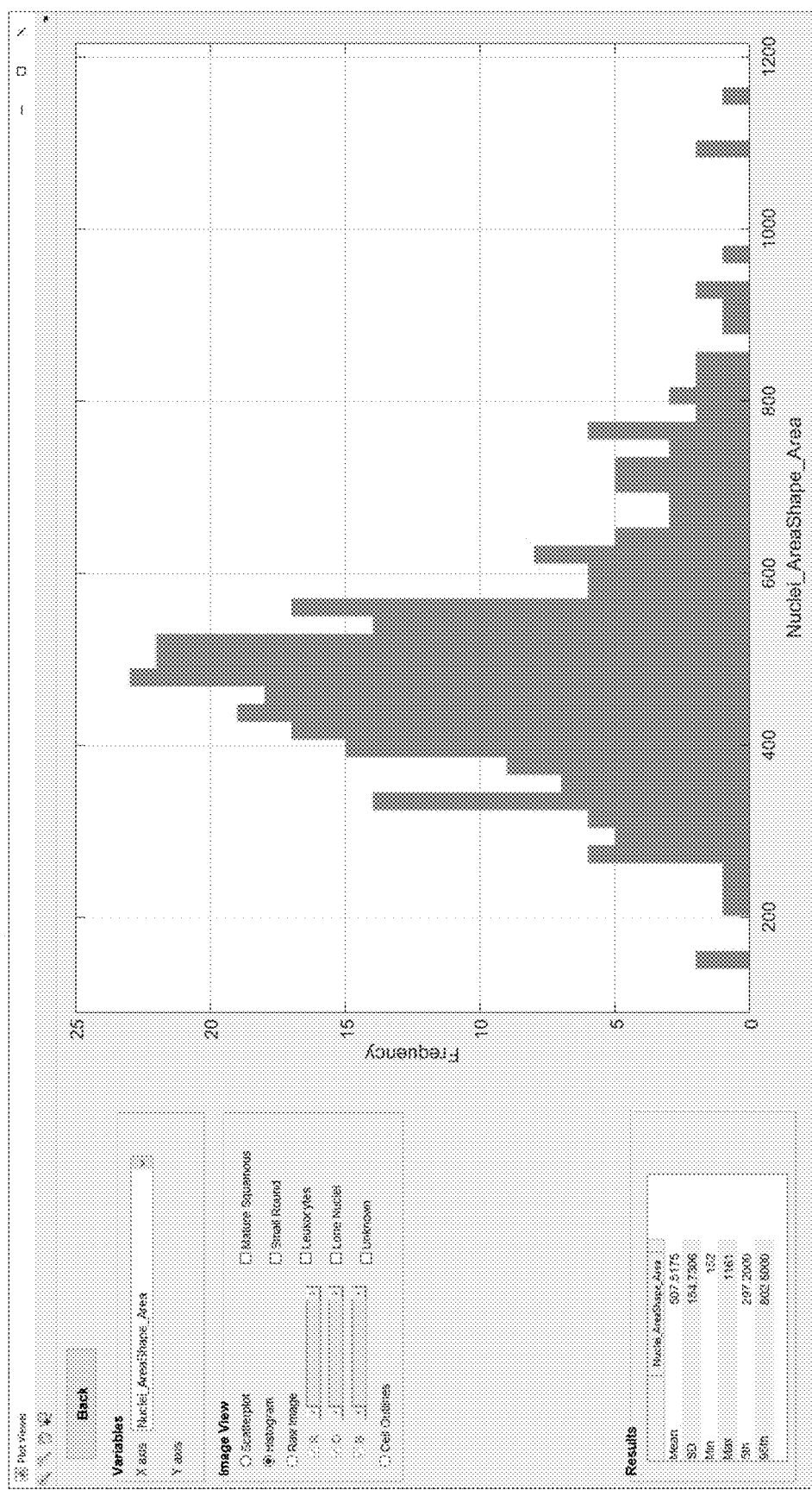

FIG. 15 depicts a screenshot of cytopathology interface showing histogram of nuclear area measurements from a sample of BICR 56 cancer cells.

Figure 16:

FIG. 16 depicts a screenshot of cytopathology interface showing brush biopsy sample of healthy control cells magnified view with all three fluorescent labels (red: phalloidin, green: EGFR, blue: DAPI).

Figure 17:
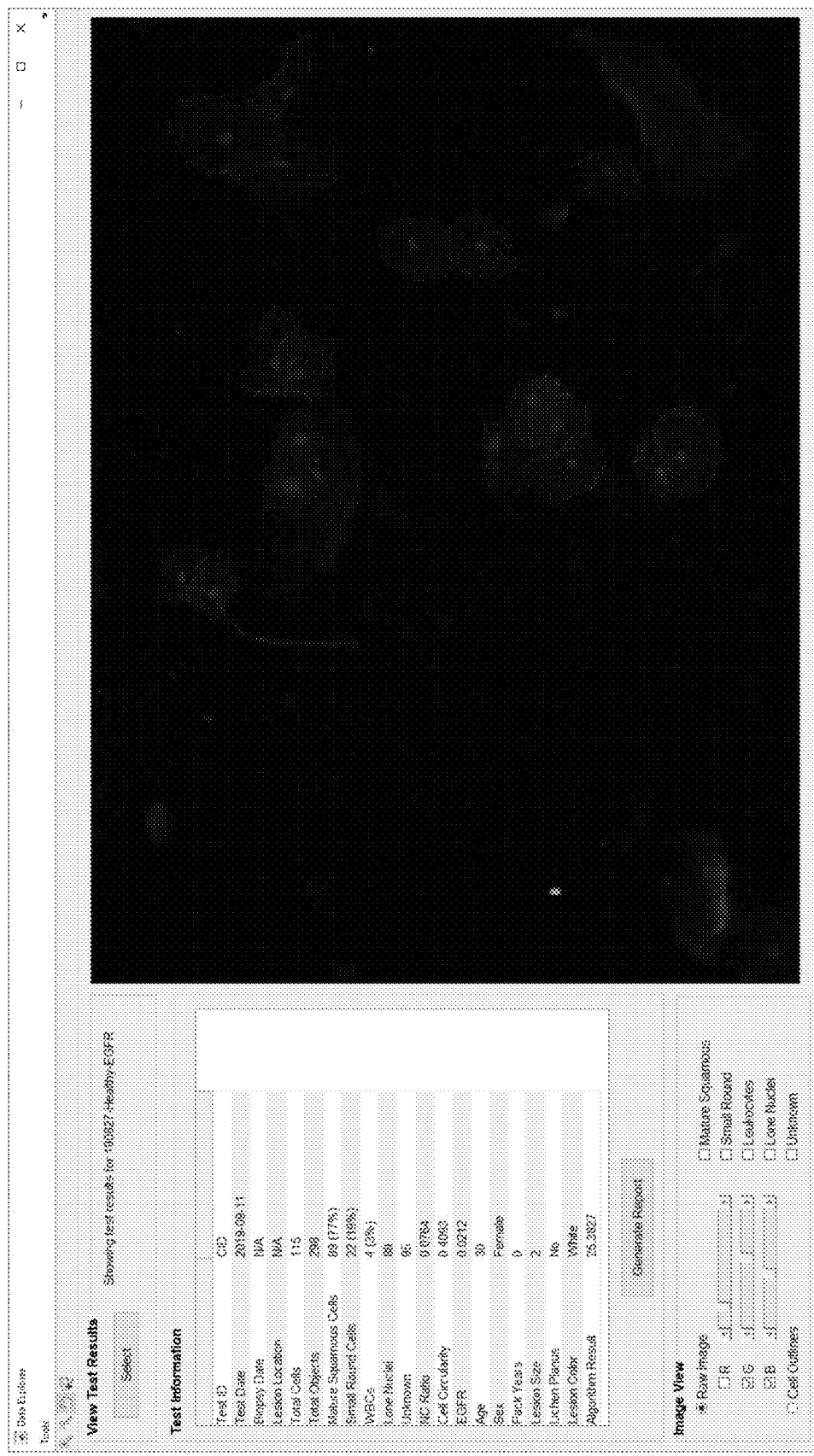

FIG. 17 depicts a screenshot of cytopathology interface showing brush biopsy sample of healthy control cells magnified view with green (EGFR) and blue (DAPI) fluorescent labels.

Figure 18:
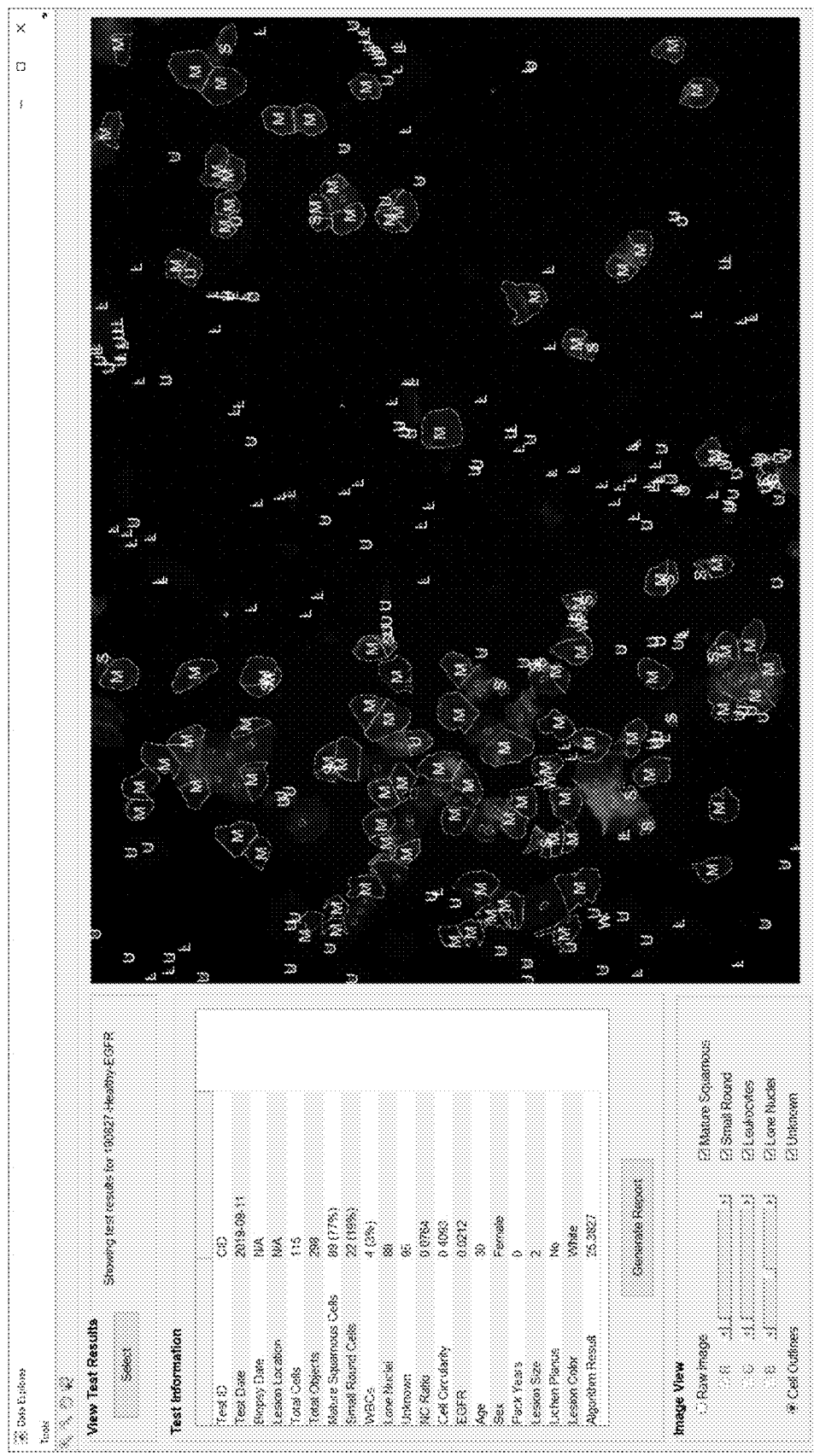

FIG. 18 depicts a Screenshot of cytopathology interface showing brush biopsy sample of healthy control cells with cell phenotype labels overlaid (M: mature squamous, S: small round, W: leukocytes, L: lone nuclei, U: unknown, not shown).

Figure 19:
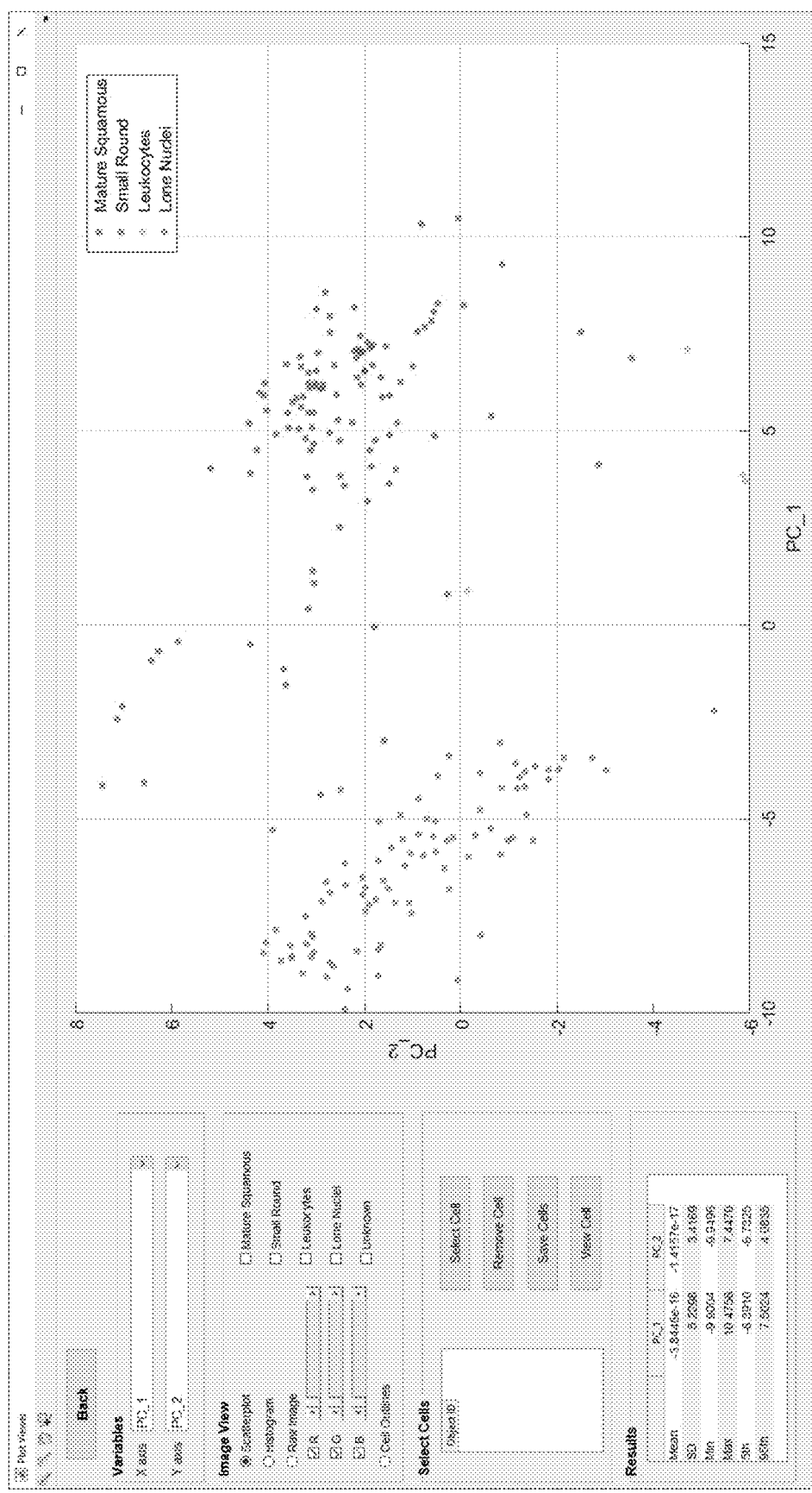

FIG. 19 depicts a screenshot of cytopathology interface showing a principal component scatter plot from a brush biopsy sample of healthy control cells.

Figure 20A:
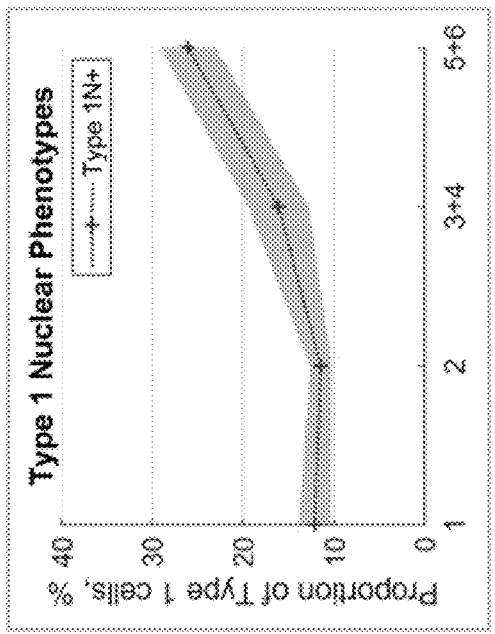
Figure 20B:
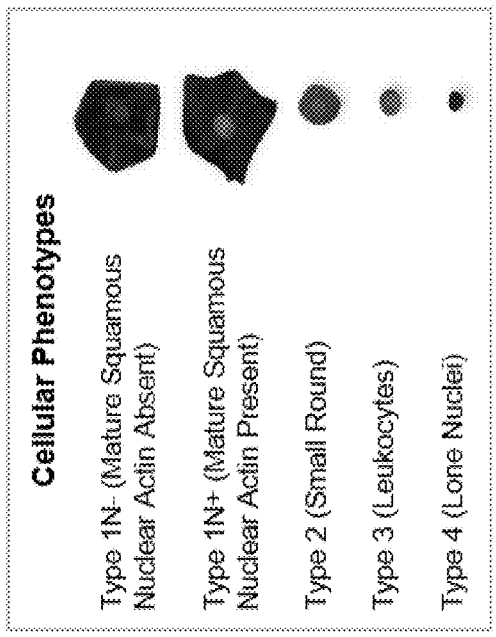
Figure 20C:
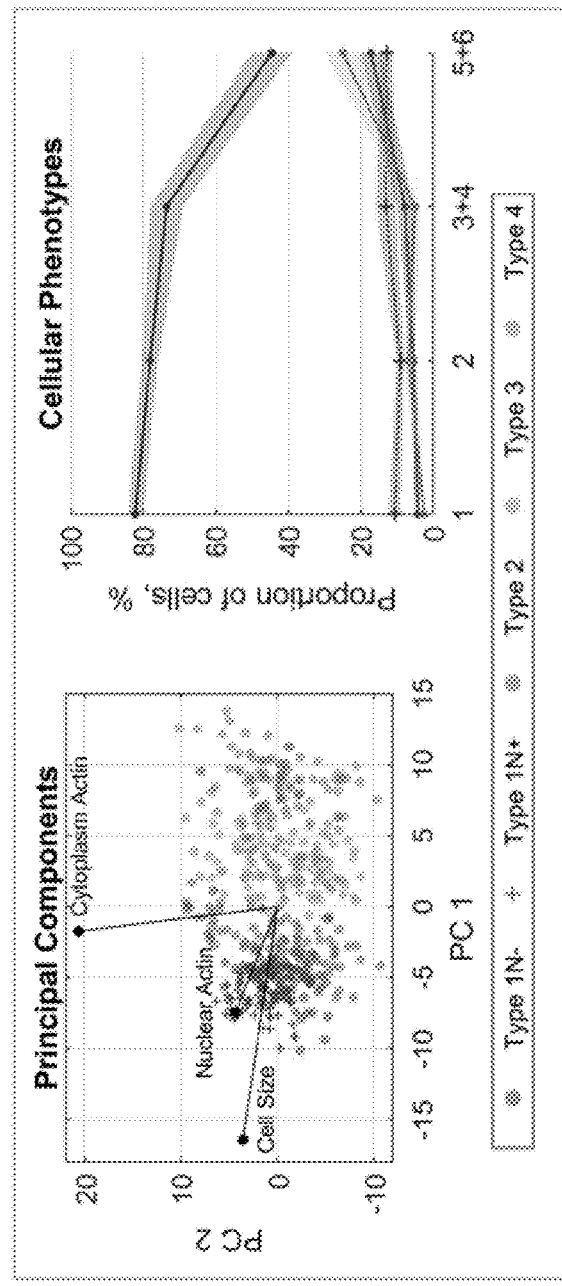

FIG. 20A-FIG. 20C depict the results of example experiments where cellular phenotype models were developed to identify five phenotypes (FIG. 20A): Type 1N- ('mature squamous cells with nuclear actin absent'), Type 1N+('mature squamous cells with nuclear actin present'), Type 2 ('small round cells'), Type 3 ('leukocytes'), and Type 4 ('lone nuclei'). Line plots (FIG. 20B) show the distribution of Type 1N+ cells out of the total Type 1 cells. Principal component analysis (FIG. 20C, left) shows cellular phenotypes with substantial separation between cellular phenotype labels. Select variables are represented as vectors (black lines) in which the direction and length of each vector indicate how each variable contributes to the first two principal components (PC1 and PC2). Line plots (FIG. 20C, right) show the distributions Types 1N+, 1N-, 2, and 3 (excludes Type 4 objects without cytoplasm) within the study population, representing the predicted mean cell type percentages and 95% CI within each lesion class: normal ('1', n=121), benign ('2', n=241), mild/moderate dysplasia ('3+4', n=50), severe dysplasia and malignant ('5+6', n=74).

Figure 21A:
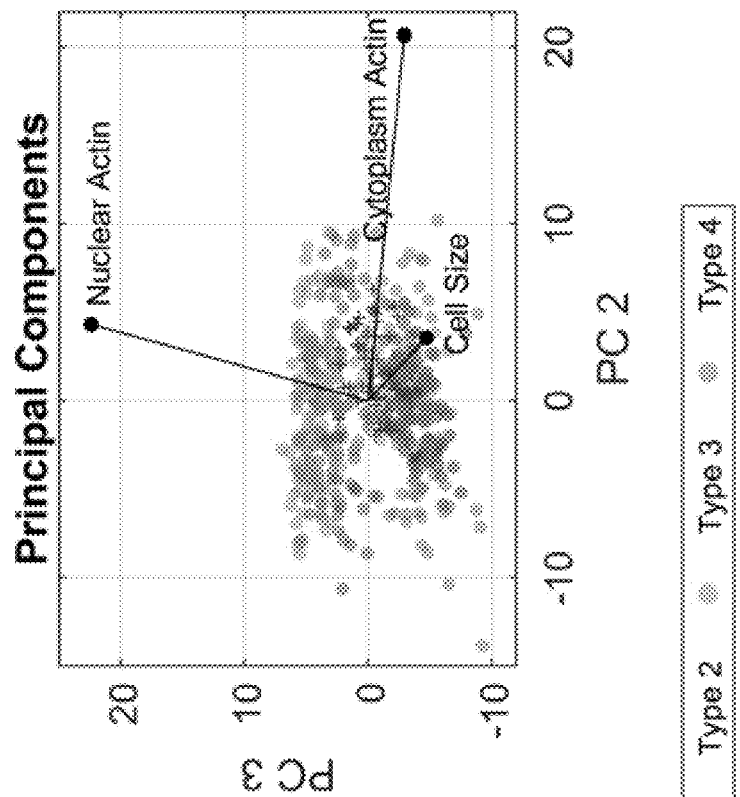
Figure 21B:
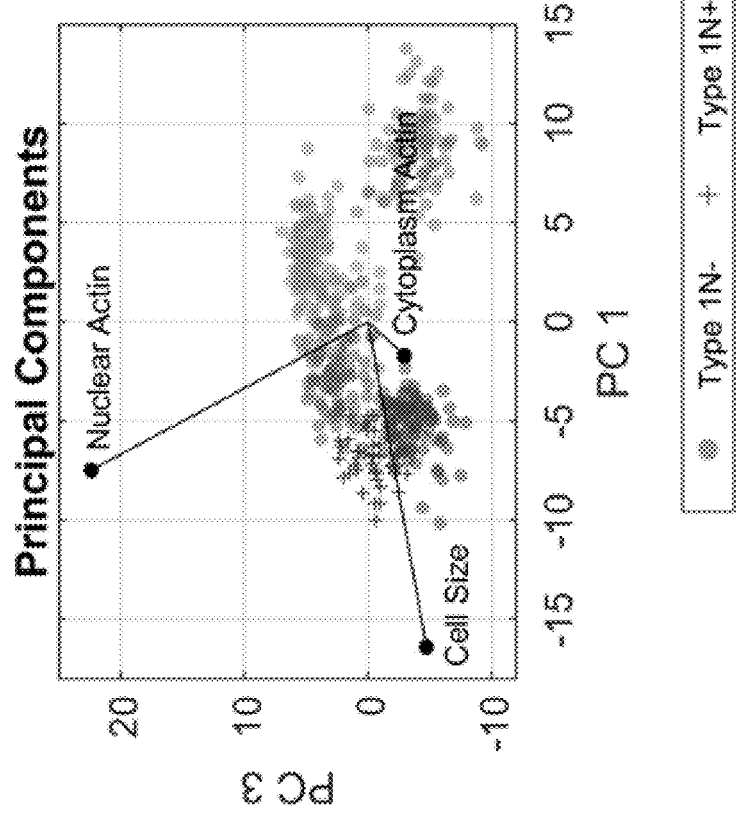

FIG. 21A and FIG. 21B depict the principal component analysis of cellular identification models for the five phenotypes that were identified: Type 1N- ('mature squamous cells with nuclear actin absent'), Type 1N+ ('mature squamous cells with nuclear actin present'), Type 2 ('small round cells'), Type 3 ('leukocytes'), and Type 4 ('lone nuclei'). Select variables are represented as vectors (black lines) in which the direction and length of the vector indicate how each variable contributes to the principal components (PC). FIG. 21A and FIG. 21B show PCs 1 vs. 3 and 2 vs. 3, respectively, in which the majority of the variance may be explained by PCs 1-3 which are largely represented by cell size, cytoplasm actin, and nuclear actin, respectively.

Figure 22A:
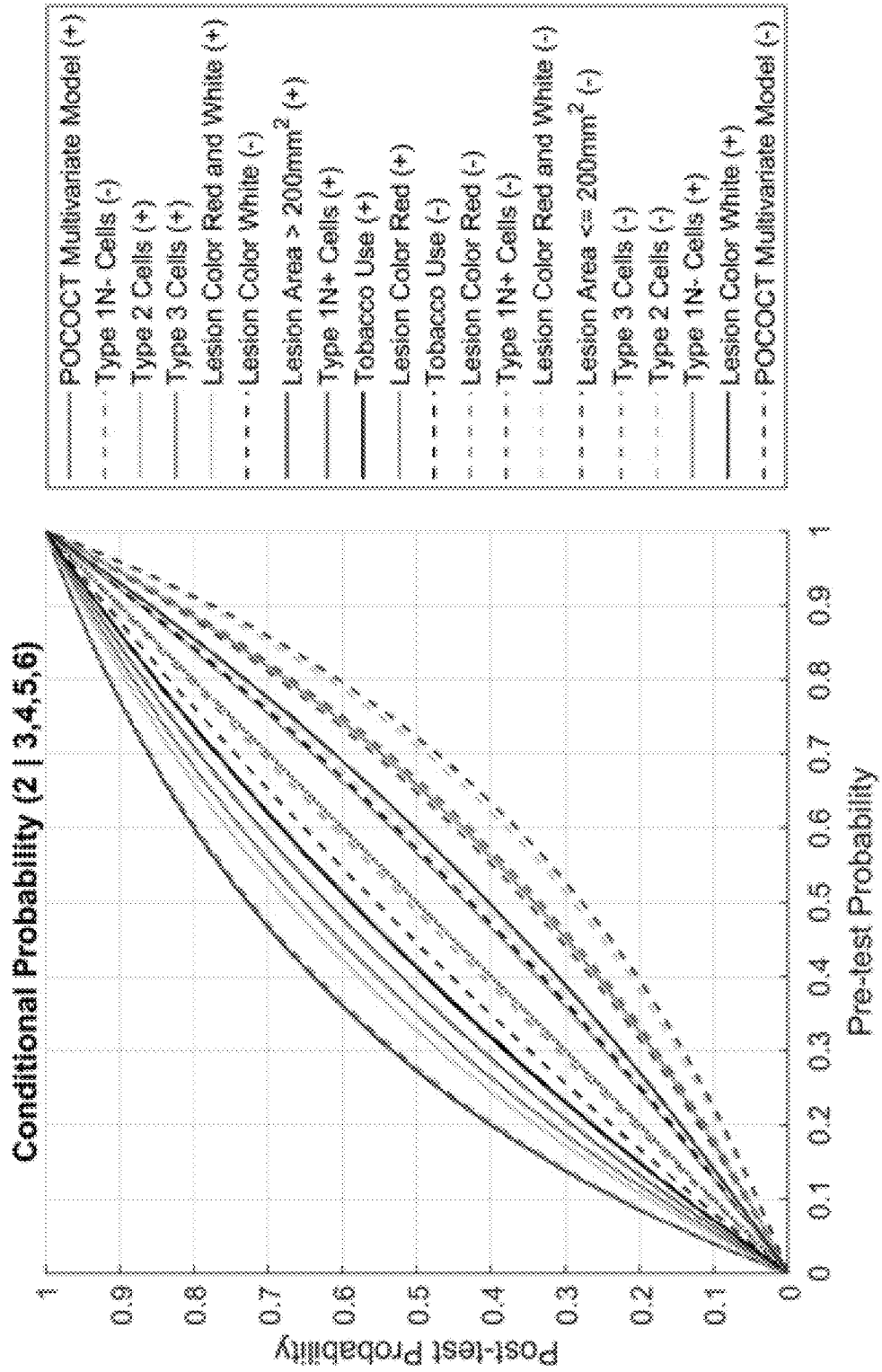
Figure 22B:
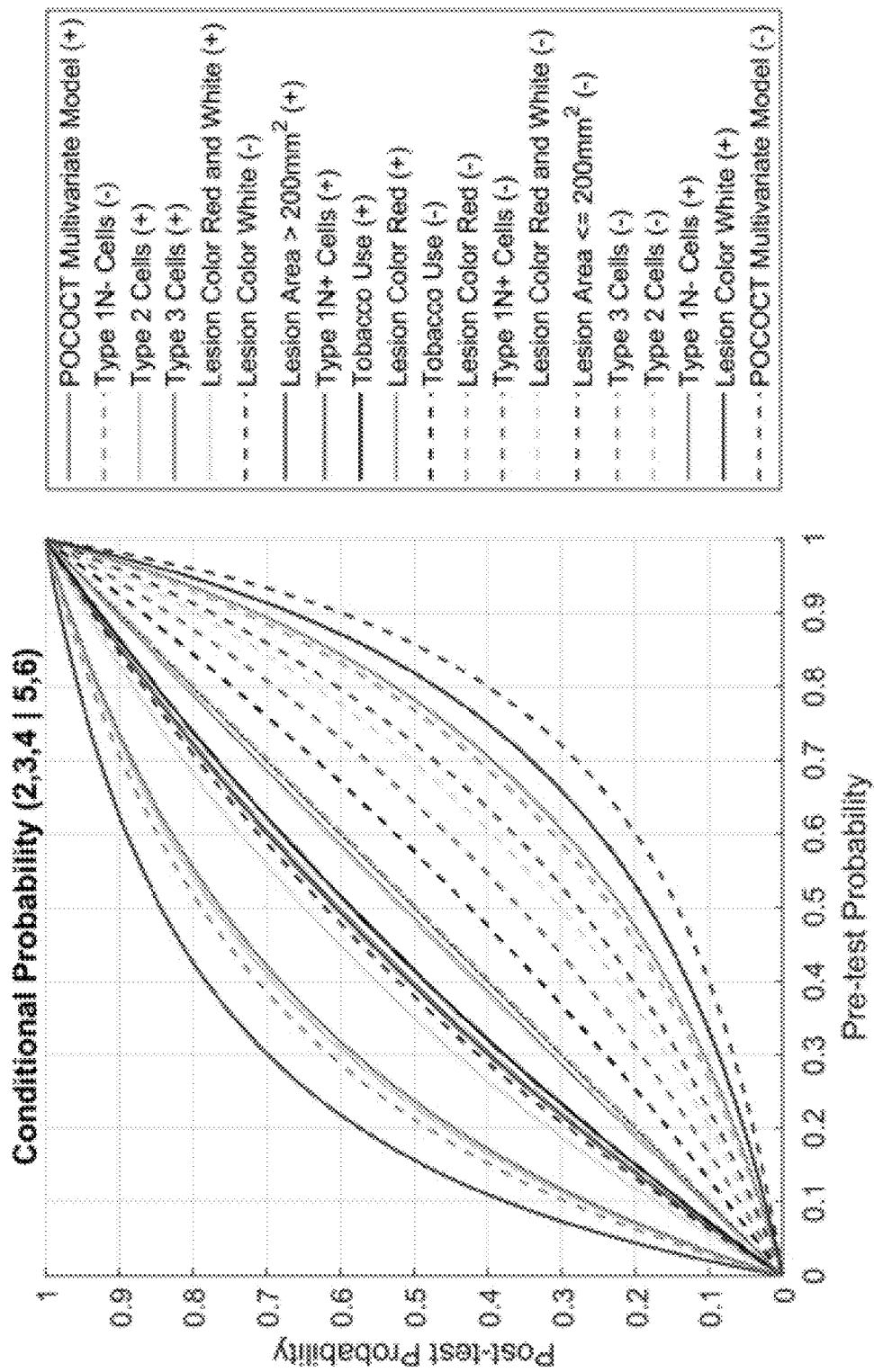

FIG. 22A and FIG. 22B depict conditional probability plots in distinguishing benign|mild dysplasia (FIG. 22A) and moderate severe dysplasia patients (FIG. 22B). Post-test probabilities are plotted as a function of pre-test probability for patients with positive (solid lines) and negative (dashed lines) indications for clinical risk factors (lesion color, lesion area, smoking), cellular phenotypes (Types 1N-, 1N+, 2, and 3), and the multivariate POCOCT model.

Figure 23:
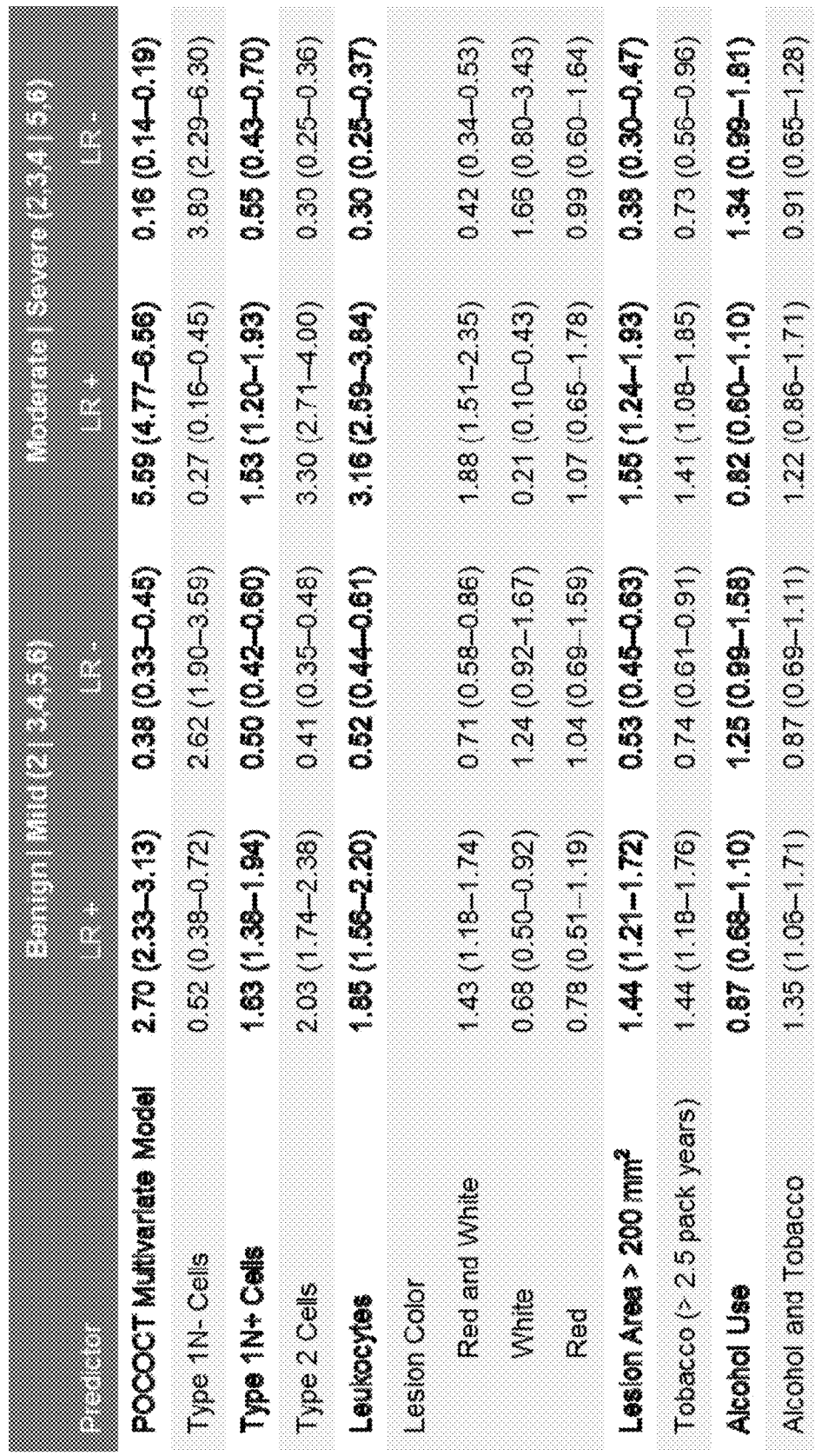

FIG. 23 depicts a table showing the positive (+) and negative (-) likelihood ratios (LR) for clinical and cytological predictors in distinguishing benign|mild dysplasia and moderate|severe dysplasia patients.

Figure 24A:
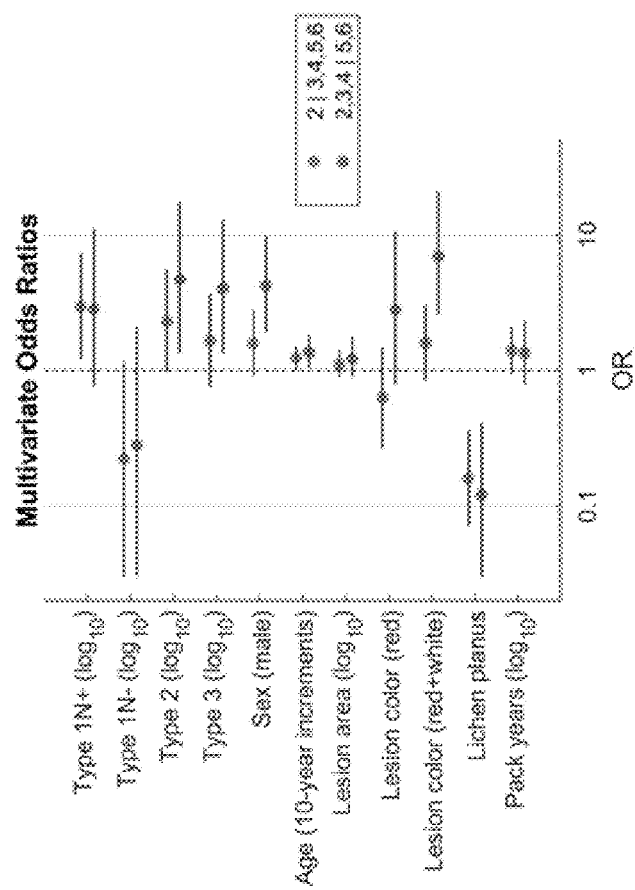
Figure 24B:
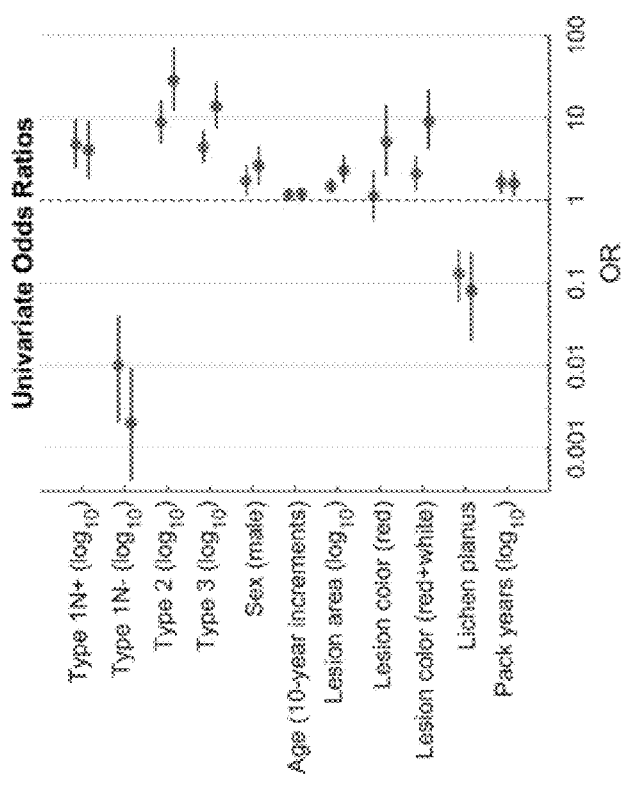

FIG. 24A and FIG. 24B depict the univariate (FIG. 24A) and multivariate (FIG. 24B) adjusted odds ratios and 95% confidence intervals for distinguishing benign|mild dysplasia and moderate|severe dysplasia patients.

FIG. 25A-FIG. 25C depict the results of diagnostic models for the OED spectrum. Results are shown for the cross-validated dichotomous algorithms for benign|mild dysplasia (2|3,4,5,6), mild|moderate dysplasia (2,3|4,5,6), low vs. high risk (2,3,4L|4H,5,6), moderate severe dysplasia (2,3,4|5,6), benign vs. malignant (2|6), and healthy control (no lesion) vs. malignant (1|6) models. Model responses for each subject were averaged over all biomarker assays to inform diagnostic performance. AUC, sensitivity, and specificity are means and 95% confidence intervals for the cross-validated test set.

DETAILED DESCRIPTION

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The word "morphometric" as used herein means the measurement of such cellular shape or morphological characteristics as cell shape, size, nuclear to cytoplasm ratio, membrane to volume ratio, and the like.

The phrase "based on" includes both contemporaneous use as well as prior use to establish parameter weights. Thus, a calculation based on earlier data training using neural nets would still be "based on" such neural net analysis, even if this part of the computational analysis does not need to be repeated.

Nuclear to cytoplasmic ratio is calculated based on cell area and nuclear area e.g., NA/CA-NA.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present disclosure relates to systems and methods for the automated identification and classification of cellular phenotypes among a cell population within a biological sample for the detection of the presence or progression of a cancer (for example oral cancer), a lesion (for example a potentially malignant oral lesion or PMOL), or a dysplasia (for example an oral epithelial dysplasia or OED). For example, in certain embodiments, the invention relates to the automated detection of mature squamous cells, small round cells, leukocytes, and lone nuclei in a sample. In certain aspects, the invention serves as an aid in the diagnosis, assessment of progression, classification of severity, scoring, and assessment of the effectiveness of treatment for oral cancer, a PMOL, and/or an OED.

In certain embodiments, the invention relates to the automated detection of the presence and absence of actin in cells, including actin content and distribution. Actin is a monomeric globular protein ("G-actin") which can polymerize to form filaments of filamentous actin ("F-actin"), and is involved in many cellular processes such as morphogenesis, intracellular transport, cell division, muscle contraction and cell migration. The actin cytoskeleton is also altered in disease processes such as in tumor cells. While actin is typically abundant in cell cytoplasm, actin has been found in cell nuclei and plays an important role in certain nuclear processes such as transcriptional regulation. The presence and distribution of actin, particularly in cell nuclei, may thereby be used as marker or target in cell-based screening methods and therapeutic approaches.

In certain embodiments, the invention relates to the automated detection of the onset of actin polymerization within cell nuclei. As actin is generally more abundant within cell cytoplasm, the formation of actin with cell nuclei involves numerous actin-binding proteins that transport actin from the cytoplasm to the nucleus and initiate polymerization. Detecting one or more of these actin-binding proteins can predict the onset of nuclear actin formation, and thereby predict the onset of an oral disease. Nucleocytoplasmic transporters of actin include but are not limited to Cofilin, Importin 9, and the like. Actin polymerizers include but are not limited to Profilin, thymosin-β4, Wiskott-Aldrich syndrome protein (WASp), Arp2/3 complex, formins, and the like.

In certain embodiments, the method integrates multiple parameters including, but not limited to, cellular phenotype, cell morphological data, biomarker data, lesion characteristics, and/or demographic information to guide health care professionals on the management of subjects having, or at risk for developing, malignant lesions. For example, in one embodiment, the method uses multiple binary classifications as inputs to create a numerical scale. The integration of the parameters described herein provides an improved ability to assess disease risk and evaluate disease progression.

A biological sample of a subject is obtained and prepared for analysis. The sample may be any suitable cytological sample. For example, in certain embodiments, the sample is a suspension of cells collected with a brush, such as a rotating brush. The sample may be obtained from a lesion or suspected lesion in the oral cavity to assess the risk or presence of oral cancer, PMOL, and/or OED. In certain embodiments, the sample is derived from a solid tissue sample or biopsy sample. In certain embodiments, the sample comprises a saliva sample or a cheek swabbed sample.

In certain embodiments, the sample is processed prior to analysis. For example, the sample may be processed to permeabilize and fix the cells contained therein. However, in certain embodiments, processing of the sample is not necessary. For example, in certain instances sample collection using a rotating brush is sufficient to permeabilize the cells.

In one embodiment, the sample is filtered, for example by collecting cells on a permeable membrane that allows debris to pass through, but not whole cells. In one embodiment, the sample is enriched for a specific cell population or subpopulation. For example, magnetic beads coupled, e.g., to a receptor or cell surface proteins, such as an antibody for EGFR, can be used to isolate and enrich specific populations.

Figure 2:
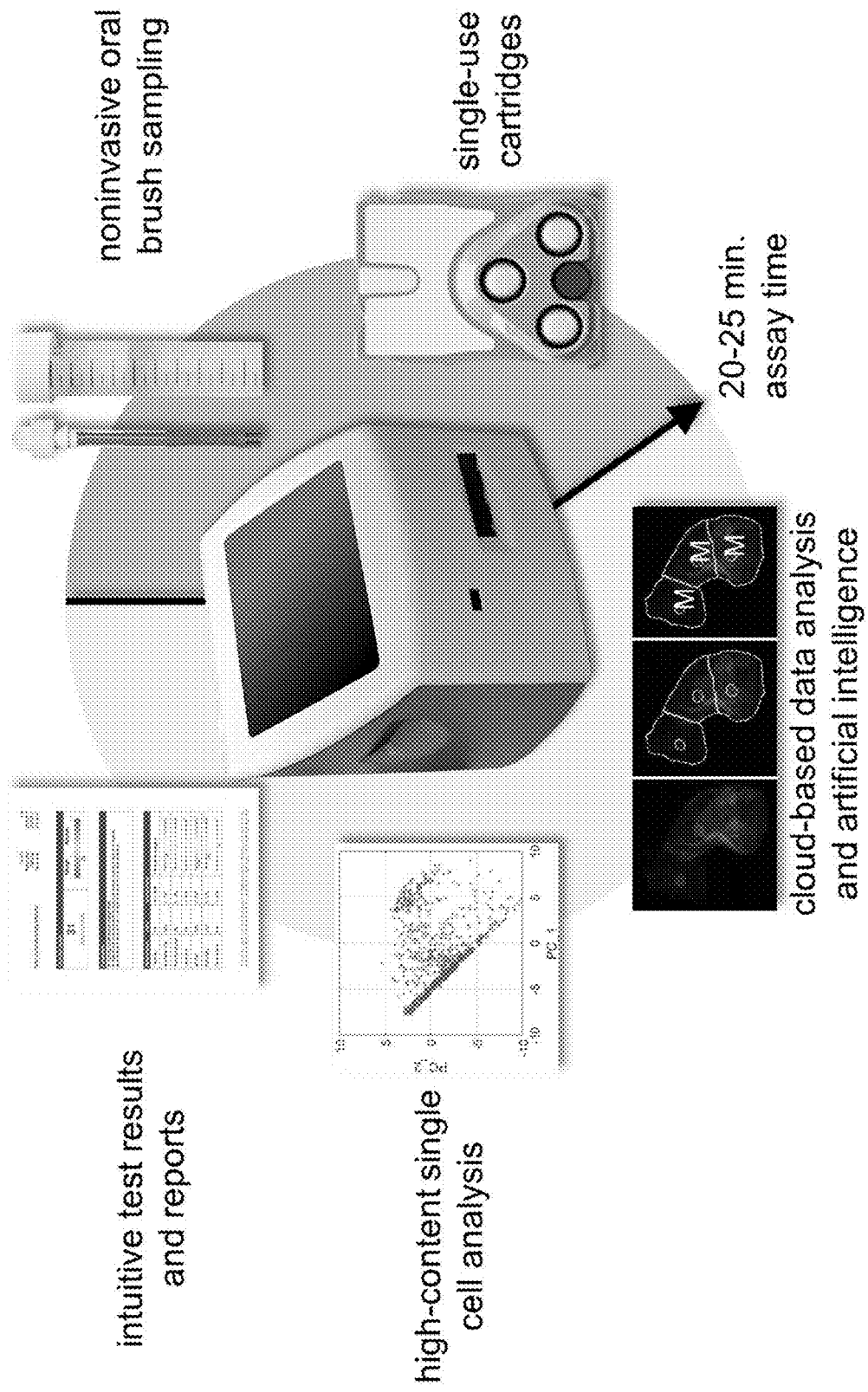
FIG. 2 depicts the Point of Care Oral Cytology Tool (POCOCT) assay platform, which allows for the analysis of cellular samples obtained from a minimally invasive brush cytology sample. The cell suspension collected in this manner allow for the simultaneous quantification of cell morphometric data and expression of molecular biomarkers of malignant potential in an automated manner using refined image analysis algorithms based on pattern recognition techniques and advanced statistical methods. This novel approach turns around cytology results in a matter of minutes as compared to days for traditional pathology methods, thereby making it amenable to POC settings. The POC testing is expected to have tremendous implications for disease management by enabling dental practitioners and primary care physicians to circumvent the need for multiple referrals and consultations before obtaining assessment of molecular risk of PMOL.

In one embodiment, the sample can be processed and analyzed using system comprising a cartridge and a reader (FIG. 2). The cartridge can comprise at least one inlet, fluidic channels, and a plurality of reagents including cellular dyes, nuclear dyes, bioaffinity ligands, antibodies, and the like, used to assess cellular phenotype, cell morphology, and/or biomarker expression. Suitable bioaffinity ligands include any molecule that binds to a biomarker of interest. Exemplary bioaffinity ligands include, but are not limited to, antibodies, antibody fragments, proteins, peptides, peptidomimetics, nucleic acid molecules, bacteriophages, aptamers, and small molecules. The reader can comprise a housing containing a slot for receiving a cartridge, a processor having a user interface, an optical or energy sensing means, and a means for moving fluid. In one embodiment, the housing also contains heating and cooling means, such as a piezoelectric heater/cooler, radiant heater and fan, peltier, or the like. The optical sensing means is configured to receive a signal from cells within the assay chamber, and the microfluidics are configured so as to allow fluid movement to and from the assay chamber. The processor and user interface control the system and the processor records data from said optical sensing means. In one embodiment, the reader includes a display means operably connected to said processor for displaying said data, but the display means is optional, and a data-port can instead connect to independent processors and/or display means. In certain embodiments, the system comprises a dedicated reader manufactured to be specific for this application, thus minimizing the size and complexity of the device, while maximizing ease of use.

In an exemplary method, a sample can be obtained using a rotating brush during a dental visit. It will be understood however, that any oral sample obtained in any setting is encompassed by the present invention. In certain embodiments, the sample is transported to a dedicated facility for analysis. In other embodiments, the sample is applied to a cartridge and reader in a point-of-care system. The cartridge and reader are used for the identification of cellular phenotype parameters, as well as, in certain embodiments, for the detection of morphological and biomarker data. In certain embodiments, the obtained data is sent over a network or to the cloud for analysis by a health care professional.

The system detects a variety of cellular phenotype, morphological and biological markers in individual cells, including for example, DAPI for DNA, and phalloidin for F-actin. These two stains provide a great deal of information about cell morphology, for example, nuclear to cytoplasm ratio (an important indicator that a cell is transforming) and cell shape (cancer cells are rounder). Other parameters that can be measured and used in the model include but are not limited to:

Area (WCArea[red]): Area of whole cell (WC) selection in square pixels determined in red from a Phalloidin stain.

Mean Intensity Value (WCMean[red], [green]): Average value within the WC selection. This is the sum of the intensity values of all the pixels in the selection divided by the number of pixels. [red] has QA/QC value and [blue] has limited descriptive value, whereas [green] is the most important for surface markers. For intracellular markers, the NuMean[green] is most descriptive.

Standard Deviation (WCStdDev[red], [green]): Standard deviation of the intensity values used to generate the mean intensity value. [red] useful for Phalloidin, QA/QC and descriptive, [green] for surface markers.

Modal Value (WCMode[red], [green]): Most frequently occurring value within the selection. Corresponds to the highest peak in the histogram. Similar to Mean in terms of value.

Min & Max Level (WCMin and WCMax[red], [green], [blue]): Minimum and maximum intensity values within the selection. Limited descriptive value, may be used for QA/QC.

Integrated Density (WCIntDen[red], [green], [blue]): Calculates and displays "IntDen" (the product of Area and Mean Gray Value)–Dependent values.

Median (WCMedian[red], [green]): The median value of the pixels in the image or selection. This again is similar to Mean and Mode in terms of utility.

Circ. (circularity): $4\pi*area/perimeter^2$: A value of 1.0 indicates a perfect circle. As the value approaches 0.0, it indicates an increasingly elongated shape. Values may not be valid for very small particles.

AR (aspect ratio): diameters of major_axis/minor_axis.

Round (roundness): $4*area/(\pi*major\_axis^2)$: Could also use the inverse of the aspect ratio.

The present invention also includes the detection and identification of the cellular phenotype of cells within the sample. For example, the presence and relative amount of mature squamous cells, presence or absence of nuclear actin in mature squamous cells, small round cells, leukocytes, and/or lone nuclei in a sample are determined to assess oral disease status in a sample of interest. In certain embodiments, the various cellular phenotypes are identified using complex object recognition routines as defined by machine learning methods. For example, in one embodiment, a user (e.g., a cytology expert) initially selects the cell types of interest. Then, various unsupervised learning routines are exploited. In doing so, the learning cell-level visual representation can obtain a rich mix of features that are highly reusable for various tasks, such as cell-level classification, nuclei segmentation, and cell counting. The cell recognition procedures use various parameters, including, but not limited to, morphological parameters, protein expression, nucleation size, shape, and intensity parameters, to recognize and identify a cell as being of a particular cellular phenotype.

In certain embodiments, the percentage of cells of a particular cellular phenotype is used to diagnose, assess the risk of developing, and/or assess the progression of oral cancer, potentially malignant oral lesions (PMOL), and/or oral epithelial dysplasia (OED).

For example, in one embodiment, a sample with about 0% to about 85% mature squamous cells indicates the presence or progression of oral cancer, PMOL, and/or OED, while a sample with about 90%-100% of mature squamous cells indicates normal tissue.

In one embodiment, a sample with nuclear actin present in about 10% to about 100% of mature squamous cells indicates the presence or progression of oral cancer, PMOL, and/or OED, while a sample with nuclear actin present in about 0% to about 10% of mature squamous cells indicates normal tissue.

In one embodiment, a sample with about 15% to about 100% of non-mature squamous cells indicates the presence or progression of oral cancer, PMOL, and/or OED, while a sample with about 0%-10% of non-mature squamous cells indicates normal tissue.

In one embodiment, a sample with about 5% to about 100% small round cells indicates the presence or progression of oral cancer, PMOL, and/or OED, while a sample with about 0% to about 5% of small round cells indicates normal tissue.

In one embodiment, a sample with about 5% to about 100% white blood cells indicates the presence or progression of oral cancer, PMOL, and/or OED, while a sample with about 0% to about 5% of white blood cells indicates normal tissue.

In one embodiment, a sample with about 20% to about 100% lone nuclei indicates the presence or progression of oral cancer, PMOL, and/or OED, while a sample with about 0% to about 20% of lone nuclei indicates normal tissue.

Cells can also be stained with labeled bioaffinity ligands (e.g. antibodies) for the various disease markers discussed herein. Generally, different biomarkers should be labeled with different labels, so that they can be distinguished. However, some overlap is allowable where the markers are spatially distinguished in the cell, e.g., EGFR on the cell surface and Ki67 in the nucleus.

As yet another alternative, the initial analysis can be on a whole cell basis, then the cells lysed and studied, and this may provide additional information about intracellular antigens. Of course, the data would then be an average over the cells in the sample, unless the cells are fixed in a particular location and the cell contents do not mix.

This disclosure also describes an expanded panel of biomarkers to cover early detection and progression of oral cancer, PMOL, and/or OED. The samples can be analyzed for the expression of molecular biomarkers including AVB6, EGFR, Ki67, Geminin, CD147, MCM2, Beta Catenin, and EMPPRIN. Other exemplary biomarkers include, but are not limited to, IL-1β, CD44, IGF-1, MMP-2, MMP-9, CD59, Catalase, Cofilin, Importin 9, Profilin, thymosin-β4, Wiskott-Aldrich syndrome protein (WASp), Arp2/3 complex, formins, S100A9/MRP14, M2BP, CEA, and Carcinoma associated antigen CA-50. The presence and/or abundance of biomarkers can be accomplished via detection of the biomarkers in whole cells or in a protein sample detected by way of an immunoassay, such as a bead-based cartridge described in U.S. Patent Application Publication No.: US20140094391, which is incorporated by reference in its entirety.

In certain embodiments, the system and methods further utilize demographic data of the subject, including, but not limited to, gender, age, alcohol intake, and smoking status of the subject.

In one embodiment, the invention provides a method of diagnosing, determining the risk of developing, assessing progression of, or scoring of an oral cancer lesion, a PMOL, and/or an OED. In one embodiment, the method comprises inputting the following data points into a computer: one or more cellular phenotype characteristics from a population of oral cells from a subject, the cellular phenotype characteristics selected from percentage of mature squamous cells, presence or absence of nuclear actin in mature squamous cells, percentage of non-mature squamous cells, percentage of small round cells, percentage of white blood cells, and percentage of lone nuclei.

In one embodiment, the method further comprises inputting the following data points into a computer: one or more morphological characteristics from individual oral cells from a patient, said morphological characteristics selected from nuclear area, cell area, cell circularity, cell aspect ratio, and cell roundness. In one embodiment, the method further comprises inputting the following data points into a computer: one or more of gender, age, alcohol intake, and smoking status of said patient. In one embodiment, the method further comprises inputting the following data points into a computer: one or more biomarker levels from individual oral cells from said patient, said biomarker selected from the group consisting of alpha V beta 6 (AVB6), Epidermal Growth Factor Receptor (EGFR), Ki67, Geminin, Mini Chromosome Maintenance protein (MCM2), beta catenin, EMPPRIN, CD147, CD44, IGF-1β, MMP-2, MMP-9, CD59, Catalase, Cofilin, Importin 9, Profilin, thymosin-β4, Wiskott-Aldrich syndrome protein (WASp), Arp2/3 complex, formins, S100A9/MRP14, M2BP, CEA, and Carcinoma associated antigen CA-50.

In one embodiment, the method comprises calculating a risk score based on each of the above inputs, said risk score allowing a user to distinguish at least the following: i) benign lesions, ii) dysplastic lesions, iii) cancerous lesions, and iv) potentially malignant lesions. In one embodiment, the method comprises displaying said risk score on an output device.

In one embodiment, the method comprises inputting the following data points into a computer: one or more cellular phenotype characteristics from a population of oral cells from a subject, the cellular phenotype characteristics selected from percentage of mature squamous cells, presence or absence of nuclear actin in mature squamous cells, percentage of non-mature squamous cells, percentage of small round cells, percentage of white blood cells, and percentage of lone nuclei.

In one embodiment, the method further comprises inputting the following data points into a computer: one or more morphological characteristics from individual oral cells from a patient, said morphological characteristics selected from cell area, nuclear area, cell circularity, cell aspect ratio, and cell roundness; one or more of gender, age, alcohol intake, and smoking status of said patient. In one embodiment, the method further comprises inputting the following data points into a computer: one or more biomarker levels from individual oral cells from said patient, said biomarker selected from the group consisting of AVB6, EGFR, Ki67, MCM2, beta catenin, EMPPRIN, and CD147, IL-1β, CD44, IGF-1, MMP-2, MMP-9, CD59, Catalase, Cofilin, Importin 9, Profilin, thymosin-β4, Wiskott-Aldrich syndrome protein (WASp), Arp2/3 complex, formins, S100A9/MRP14, M2BP, CEA, and Carcinoma associated antigen CA-50.

In certain embodiments, the method comprises detecting the level of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty of the biomarkers described herein.

In certain embodiments, the method comprises detecting the level of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty of the biomarkers of: AVB6, EGFR, Ki67, MCM2, beta catenin, EMPPRIN, CD147, IL-1β, CD44, IGF-1, MMP-2, MMP-9, CD59, Catalase, Cofilin, Importin 9, Profilin, thymosin-β4, Wiskott-Aldrich syndrome protein (WASp), Arp2/3 complex, formins, S100A9/MRP14, M2BP, CEA, and Carcinoma associated antigen CA-50.

In one embodiment, the method comprises calculating a risk score based on each of the above inputs, wherein said calculation is based on logistic regression or neural network training using data points from patients with known disease status, said risk score providing at least 3 disease classifications. Additional information related to the calculation of a risk score can be found at least in U.S. Patent Application Publication No.: US20140235487, which is incorporated by reference in its entirety.

In one embodiment, the calculation results in 4-way, 5-way or 6-way ordinal scales of disease progression. In certain embodiments, the calculation allows a user to distinguish the following: 1) normal, 2) benign lesions, 3) mild dysplasia, 4) moderate dysplasia, 5) severe dysplasia, and 6) carcinoma in situ/malignant lesion.

In one embodiment, the method allows a user to distinguish between benign conditions, mild dysplastic conditions, moderate dysplastic conditions, severe dysplastic conditions and cancerous conditions or allows a user to distinguish the following: 1) benign conditions, 2) dysplastic conditions, 3) moderate disease, 4) high risk disease.

In certain embodiments, the calculation is based on artificial neural nets, logistic regression, linear discriminate analysis, or random forests or based on feed forward artificial neural nets. In some methods, the calculation is based on prior artificial neural network model training using data points from patients with known disease states, or is based on continued neural network model training using data points from patients with known disease states and outcomes. In certain embodiments, each inputted data point corresponds to a node, and each node is linked to serve as an input in a neural network in creating a single output risk score on a continuous scale between 1 and 10. In certain embodiments, the calculation is based on inputting nodes into an input layer, said nodes obtained through logistic regression of all possible classifications of patient samples having known disease states according to at least 3-way classifications; optimizing the artificial neural network as to the number of hidden layers and computing nodes, and outputting a normalized score between 1 and 10, 1 corresponding to benign and 10 corresponding to malignant.

In one embodiment, the calculation is made using the following: Oral Cancer Risk Score=$a0+a1 \times P1+a2 \times P2+ \ldots$ an $X$ Pn, where each of P1, P2, ... Pn is a node of a logistic regression model, where n is the number of nodes and where $a0-an$ is a weight factor determined by training with input data from patients having known disease status.

Typically, in "classification" models, a single measure is collected per biomarker in each sample (e.g. panel of molecular biomarkers concentrations, or morphologic biomarker measures). In some embodiments, the biomarkers are measured for each cell, resulting in hundreds to thousands of measurements per biomarker per sample. Thus, each biomarker has an entire distribution of measurements per sample. In some embodiments, these distributions of biomarker values are further complicated by the fact that the cells within a sample may be heterogeneous, with some cells being benign and other cells being dysplastic or malignant. A homogeneous sample of cells would likely have a bell-shaped distribution on either the arithmetic or logarithmic scales. However, a sample with a heterogeneous mixture of cell types would likely (if the biomarker had good discriminatory properties) be skewed or bi-modal in distribution. Further, the heterogeneous mixture of cell types may increase the biomarker's variance, standard deviation, coefficient of variability (cv), interquartile range, flatness (kurtosis), and skewness. Thus, in certain instances when analyzing biomarker concentration over all cells within a sample, it is useful to try multiple measures of the biomarker distribution in fitting the statistical models. For example, biomarker parameters can be was summarized using the following distributional measures: Mean, Median, Variance, Standard deviation, Coefficient of variation (cv), Skewness, Kurtosis (any measure of the "peakedness" of the probability distribution), 10th Percentile, 25th Percentile, 75th Percentile, 90th Percentile, >0.5 Z-Score (percent of cells with biomarker values greater than 0.5 standard deviations away from healthy cells), >2.0 Z-Score (percent of cells with biomarker values greater than 2.0 standard deviations away from healthy cells), or >3.0 Z-Score (percent of cells with biomarker values greater than 3.0 standard deviations away from healthy cells). Biomarker measurements include, but are not limited to intensity, or biomarker index (% of positive cells per patient/assay based on comparison of each cell's intensity to the intensity of the Control population for that particular biomarker), as well as morphological measurements, including but not limited to nuclear area, cell area, nuclear to cytoplasm ratio distribution, indices, or mean. Some or all of these are combined to establish the largest area under the curve (AUC), or ability to discriminate between two classes, one defined as the cases, the other as the non-cases.

The term "neural network" is traditionally used to refer to a network or circuit of biological neurons, however, modern usage of the term often refers to artificial neural networks, which are composed of artificial neurons or nodes. Thus, the term as used herein refers to artificial neural networks for solving artificial intelligence problems.

An artificial neural network (ANN), often just called a neural network (NN), consists of an interconnected group of artificial neurons, and processes information using a connectionist approach to computation. In most cases a neural network is an adaptive system changing its structure during a learning phase. Neural networks are used for modeling complex relationships between inputs and outputs or to find patterns in data. Neural Networks have several unique advantages as tools for cancer prediction. A very important feature of these networks is their adaptive nature, where "learning by example" replaces conventional "programming by different cases" in solving problems.

There are three major learning paradigms, each corresponding to a particular abstract learning task. These are supervised learning, unsupervised learning and reinforcement learning.

Most of the algorithms used in training artificial neural networks employ some form of gradient descent. This is done by taking the derivative of the cost function with respect to the network parameters and then changing those parameters in a gradient-related direction. Evolutionary methods, gene expression programming, simulated annealing, expectation-maximization, non-parametric methods and particle swarm optimization are some commonly used methods for training neural networks.

This disclosed method can be used by health care providers to determine the risk of oral cancer, PMOL, and/or OED and the/or the need for additional testing. In one example, a score higher than 5 means a patient needs to be referred to scalpel biopsy. A score between 3 and 5 may mean a patient needs to be seen in one month for a repeat brush biopsy. A clear quantitative score such as one produced here will empower clinicians to make these decisions with more assurance.

In certain embodiments, the method comprises treating a subject with an oral disease treatment regimen based upon the assessment using the system and method described herein. For example, in certain embodiments, a subject is treated with chemotherapy, radiation, hormone therapy, surgery, targeted therapy (e.g. small molecules and therapeutic antibodies) or the like based at least in part upon an assessment produced by a system or method of the present invention.

In certain embodiments, the method comprises performing a subsequent analysis on a subsequent sample obtained from the subject after a treatment regimen is administered, in order to assess the efficacy of the administered treatment regimen.

In one embodiment, a method of training a neural network includes obtaining images of a plurality of tissue samples from a plurality of subjects, analyzing the plurality of tissue samples to calculate or obtain one or more morphological characteristics as disclosed herein, obtaining measures or calculating a plurality of biomarkers corresponding to the plurality of subjects as disclosed herein, obtaining a set of binary or non-binary output classification values for the plurality of subjects as described herein, and training a neural network to assign weight factors to the plurality of input parameters (comprising the images of the tissue samples, the morphological characteristics, and the biomarkers), in order to generate a predictive model for the one or more binary or non-binary output classifiers based on the input parameters. In some embodiments, the predictive model is configured to generate one or more risk factors based on the binary or non-binary output classification values. In some embodiments, the method further comprises obtaining a set of demographic data or other characteristics from the plurality of subjects and training the machine learning algorithm to optimize one or more weight factors of the biomarkers and/or demographic data in order to build the predictive model.

In one embodiment, the invention provides a kit for diagnosing or assessing oral disease. In one embodiment, the kit comprises a cartridge of the invention. In one embodiment, the cartridge is wrapped in an airtight package. In one embodiment, the kit further comprises a vial of assay fluid. The kit can include other components, e.g., instructions for use.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, and/or 5G networks, Bluetooth®, Bluetooth® Low Energy (BLE), Near Field Communication (NFC), or Zigbee® communication links, or any other method by which one electronic device is capable of communicating with another.

In some embodiments, elements of the networked portion of the invention may be implemented over a Virtual Private Network (VPN).

Aspects of the invention relate to a machine learning algorithm, machine learning engine, or neural network. A neural network may be trained based on various attributes of one or more cells, examples of which are disclosed herein, and may output one or more predictive values based on the attributes. The resulting predictive values may then be judged according their success rate in matching one or more binary classifiers or quality metrics for known input values, and the weights of the attributes may be optimized to maximize the average success rate for binary classifiers or quality metrics. In this manner, a neural network can be trained to predict and optimize for any binary classifier or quality metric that can be experimentally measured. Examples of binary classifiers or quality metrics that a neural network can be trained on are discussed herein, including cancer severity, effectiveness of cancer treatment, or cancer diagnosis. In some embodiments, the neural network may have multi-task functionality and allow for simultaneous prediction and optimization of multiple quality metrics.

In embodiments that implement such a neural network, a neural network of the present invention may identify one or more attributes whose predictive value (as evaluated by the neural network) has a high correlative value, thereby indicating a strong correlation with one or more results.

In some embodiments, the neural network may be updated by training the neural network using additional inputs having known outcomes. Updating the neural network in this manner may improve the ability of the neural network in predictive accuracy. In some embodiments, training the neural network may include using a value of a desirable parameter associated with a known outcome. For example, in some embodiments, training the neural network may include predicting a value of an output parameter for a set of cell images, comparing the predicted value to the corresponding value associated with a known output parameter from the subject from which the cell images were drawn, and training the neural network based on a result of the comparison. If the predicted value is the same or substantially similar to the observed value, then the neural network may be minimally updated or not updated at all. If the predicted value differs from that of the known output parameter, then the neural network may be substantially updated to better correct for this discrepancy. Regardless of how the neural network is retrained, the retrained neural network may be used to propose additional attributes and weightings for new or existing attributes.

Although the techniques of the present application are in the context of disease diagnosis, assessment, and treatment, it should be appreciated that this is a non-limiting application of these techniques as they can be applied to other types of parameters or attributes. Depending on the type of data used to train the neural network, the neural network can be optimized for different types of diagnosis and treatment. Querying the neural network may include inputting an initial data set and set of one or more attributes disclosed herein. The neural network may have been previously trained using different data set. The query to the neural network may be for one or more predictive output values. A binary or non-binary output value may be received from the neural network in response to the query.

The techniques described herein associated with iteratively querying a neural network by inputting a training data set, receiving an output from the neural network that has one or more output values, and successively providing further data sets as an input to the neural network, can be applied to other machine learning applications.

In some embodiments, an iterative process is formed by querying the neural network for one or more output parameters based on an input data set, receiving the one or more output parameters, and identifying one or more changes to be made to the input data set based on the output received. An additional iteration of the iterative process may include inputting the data set from an immediately prior iteration with one or more changes. The iterative process may stop when one or more output values substantially match the output values from a training iteration.

Cloud, cloud service, cloud server, and cloud database relate to information storage and storage related services provided remotely by a third party to a repository of data. A cloud service may include one or more cloud servers and cloud databases that allows for remote storage of information, hosted by a third party and stored outside of a repository of data. A cloud server may include an HTTP/HTTPS server sending and receiving HTTP/HTTPS messages in order to provide web browsing user interfaces to client web browsers. A cloud server may be implemented in one or more actual servers as known in the art, and may send and receive data, user supplied information, or configuration data, among other data, that may be transferred to, read from, or stored in a cloud database. A cloud database may include a relational database such as an SQL database, or fixed content storage system, used to store collected information or any other configuration or administration information required to implement the cloud service. A cloud database may include one or more physical servers, databases, or storage devices that are necessary to implement the cloud service's storage requirements.

A cloud service may also include one or more computing platforms configured to execute algorithms in computer software. The cloud service may access or retrieve sample data stored on the one or more cloud servers and cloud databases for the purpose of processing the stored sample data for image and statistical analysis using the algorithms and computational models described herein. The cloud service may output data in the form of images or scores of stored sample data and upload the output data to one or more cloud servers and cloud databases for retrieval by a user, such as a clinician.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1

Effective detection and monitoring of potentially malignant oral lesions (PMOL) are critical to identifying early stage cancer and improving outcomes. Described herein are cytopathology tools including machine learning algorithms, clinical algorithms, and test reports developed to assist pathologists and clinicians with PMOL evaluation. Data were acquired from a multi-site clinical validation study of 999 subjects with PMOLs and oral squamous cell carcinoma (OSCC) using a cytology-on-a-chip approach. A machine learning model was trained to recognize and quantify the distributions of four cell phenotypes. A least absolute shrinkage and selection operator (lasso) logistic regression model was trained to distinguish PMOLs and cancer across a spectrum of histopathologic diagnoses ranging from benign, to increasing grades of oral epithelial dysplasia (OED), to OSCC using demographics, lesion characteristics, and cell phenotypes. Cytopathology software was developed to assist pathologists in reviewing brush cytology test results, including high-content cell analyses, data visualization tools, and results reporting. Cell phenotypes were accurately determined through an automated cytological assay and machine learning approach (99.3% accuracy). Significant differences in cell phenotype distributions across diagnostic categories were found in three phenotypes (Type 1 'mature squamous', Type 2 'small round', and Type 3 'leukocytes'). The clinical algorithms resulted in acceptable performance characteristics (AUC=0.81 for benign vs. mild dysplasia and 0.95 for benign vs. malignancy). These new cytopathology tools represent a practical solution for rapid PMOL assessment with the potential to facilitate screening and longitudinal monitoring in primary, secondary, and tertiary clinical care settings.

Previously, the conceptual basis and the efficacy of chip-based cell capture, multispectral fluorescence measurements, and single-cell analysis approaches have been demonstrated yielding high content diagnostic information related to oral lesions (Weigum S E et al., Lab on a Chip. 2007; 7(8):995-1003; Weigum S E et al., Cancer Prevention Research. 2010 Apr. 1; 3(4):518-28; McDevitt J et al., SPIE newsroom. 2011 Mar. 28). This compact and integrated lesion diagnostic adjunct approach has been studied previously through a multi-site clinical validation effort that has led to the development of one of the largest oral cytology databases ever assembled for PMOLs (Abram T J et al., Oral oncology. 2016 Sep. 1; 60:103-11; Speight P M et al., Oral surgery, oral medicine, oral pathology and oral radiology. 2015 Oct. 1; 120(4):474-82). These efforts included the development of an "enhanced gold standard" adjudication process (Speight P M et al., Oral surgery, oral medicine, oral pathology and oral radiology. 2015 Oct. 1; 120(4):474-82) that was used to correlate brush cytology measurements with six levels of histopathological diagnosis, ranging from benign, to OED, to OSCC. The same approach showed strong promise for OSCC surveillance in Fanconi Anemia patients (Abram T J et al., Translational oncology. 2018 Apr. 1; 11(2):477-86) and for the development of a cytology based numerical risk index for cancer progression (Abram T J et al., Oral oncology. 2019 May 1; 92:6-11). Overall, these past efforts have revealed that microfluidic-based cell capture systems with integrated imaging and embedded diagnostic algorithms can yield diagnostic accuracies that rival and exceed the capabilities of previously developed adjunct devices. These tools were developed previously to serve as adjunctive aids capable of distinguishing between high risk and low risk oral lesions with the goal of improving the pipeline of referrals from primary care settings to secondary and tertiary treatment centers. Thus, these models were intended for assisting primary care providers in making binary referral decisions and considered hundreds of complicated image-based cytomorphometric features with minimal clinical interpretability (i.e., "black box").

Described herein is the development of a Point of Care Oral Cytology Tool (POCOCT), the first precision oncology technology capable of high content cell analysis for near patient testing. The POCOCT platform comprises a minimally invasive brush cytology test kit, disposable assay cartridge, instrument, clinical algorithms, and cloud-based software services that automate the quantification and analysis of cellular and molecular signatures of dysplasia with results available in a matter of minutes as compared to days for traditional labor intensive lab-based pathology methods. The experiments described herein features the development of new diagnostic models using the same database described above with the goal of greatly simplifying the diagnostic algorithms and their interpretation through the classification and quantification of cellular phenotypes, resulting in more informative and transparent models for cytopathologists. Likewise, this work explores the utility of cell phenotype identification through machine learning, their implementation in diagnostic models with interpretable predictors and responses, and the practical application of these software tools in a cytopathology service.

The methods and materials employed in these experiments are described.

Oral Cytology Data

Data used in this study originated from the 999-patient multisite prospective non-interventional study evaluating the cytology-on-a-chip system for the measurement of cytological parameters on brush cytology samples to assist in the diagnosis of PMOL (Abram T J et al., Oral oncology. 2016 Sep. 1; 60:103-11; Speight P M et al., Oral surgery, oral medicine, oral pathology and oral radiology. 2015 Oct. 1; 120(4):474-82). Briefly, both histopathological and brush cytological samples for 714 subjects from three patient groups were measured: (1) subjects with PMOL who underwent scalpel biopsy as part of the standard of care for microscopic diagnosis, (2) subjects with recently diagnosed malignant lesions, and (3) healthy volunteers without lesions. Histopathological assessment of scalpel biopsy specimens classified lesions into six categories (benign, mild-, moderate- or severe-dysplasia, carcinoma-in-situ, and OSCC), including healthy controls without lesions. While traditionally the grading of OED has been considered subjective and lacking intra- and inter-observer reproducibility (Bosman F T, The Journal of Pathology: A Journal of the Pathological Society of Great Britain and Ireland. 2001 June; 194(2):143-4; Warnakulasuriya S et al., Journal of Oral Pathology & Medicine. 2008 March; 37(3):127-33), this new study implemented an "enhanced gold standard" adjudication (Speight P M et al., Oral surgery, oral medicine, oral pathology and oral radiology. 2015 Oct. 1; 120(4):474-82). Here, two adjacent serial histologic sections were independently scored by two pathologists. In the event that the pathologists disagreed, a third independent adjudicating pathologist reviewed both sections. If the adjudicator did not agree with either of the initial two pathologists, a third stage consensus review was conducted to attain a final diagnosis. This "enhanced gold standard" process was able to achieve 100% consensus agreement compared to an initial pre-adjudication 69.9% agreement rate.

Brush cytology specimens were collected and processed using protocols published previously (Abram T J et al., Oral oncology. 2016 Sep. 1; 60:103-11; Speight P M et al., Oral surgery, oral medicine, oral pathology and oral radiology. 2015 Oct. 1; 120(4):474-82). Cytopathological assessment of brush cytology specimens implemented a cytology-on-a-chip approach which measured morphological and intensity-based cell metrics as well as the expression of six molecular biomarkers ($\alpha v\beta 6$, EGFR, CD147, McM2, Geminin, and Ki67), resulting in a total of 13 million cells analyzed with over 150 image-based parameters. The molecular biomarkers were selected based on their capacity to distinguish benign, dysplastic, and malignant oral epithelial cells through prior immunohistochemistry studies (Weigum S E et al., Cancer Prevention Research. 2010 Apr. 1; 3(4):518-28; Vigneswaran N et al., Experimental and molecular pathology. 2006 Apr. 1; 80(2):147-59; Torres-Rendon A et al., British journal of cancer. 2009 April; 100(7):1128). Specific details on the molecular biomarker selection, patient characteristics, sample collection and processing, cytology assay, and cytological parameters were published previously (Abram T J et al., Oral oncology. 2016 Sep. 1; 60:103-11) and are summarized elsewhere herein.

Biomarker Selection Rationale

Six molecular biomarkers were selected ($\alpha v\beta 6$, CD147, EGFR, geminin, Ki67, and MCM2) based on their capacity to distinguish benign, dysplastic, and malignant oral epithelial cells through prior immunohistochemistry studies (Vigneswaran N et al., Experimental and molecular pathology. 2006 Apr. 1; 80(2):147-59; Torres-Rendon A et al., British journal of cancer. 2009 April; 100(7):1128; Weigum S E et al., Cancer Prevention Research. 2010 Apr. 1; 3(4):518-28). These markers fall into three groups based on their localization: cell membrane, cytoplasm, and nucleus. Table 1 summarizes the molecular biomarkers used in the study.

TABLE 1

Summary of molecular biomarkers

| Biomarker | Localization | Function |
|---|---|---|
| $\alpha v\beta 6$ | CM | an integrin receptor undetectable in normal oral epithelium, but highly expressed in dysplasia and OSCC (Li HX et al., Journal of Oral Pathology & Medicine. 2013 August; 42(7):547-56; Ylipalosaari M et al., Experimental cell research. 2005 October 1; 309(2):273-83) |
| CD147 | CM | a multifaceted molecule that facilitates tumor progression by several mechanisms (Yu YH et al., Oral surgery, oral medicine, oral pathology and oral radiology. 2015 May 1; 119(5):553-65) |
| EGFR | CM + C | a transmembrane glycoprotein whose overexpression may contribute to tumor progression (Daniel FI et al., Applied Cancer Research. 2010; 30(3):279-88) |
| Geminin | N + C | a marker of proliferation (Torres-Rendon A et al., British journal of cancer. 2009 April; 100(7):1128) |

TABLE 1-continued

Summary of molecular biomarkers

| Biomarker | Localization | Function |
|---|---|---|
| Ki67 | N | a marker of proliferation that is overexpressed at initial stages of oral carcinogenesis (Daniel FI et al., Applied Cancer Research. 2010; 30(3):279-88) |
| MCM2 | N | an essential component for DNA replication associated with deregulated expression in dysplastic and malignant epithelial cells (Williams GH et al., Proceedings of the National Academy of Sciences. 1998 December 8; 95(25): 14932-7; Scott IS et al., British journal of cancer. 2006 April; 94(8):1170) |

*CM: cell membrane; C: cytoplasm; N: nucleus

Patient Recruitment

Data used in this study originated from the 999-patient multisite prospective non-interventional study evaluating the cytology-on-a-chip system for the measurement of cytological parameters on brush cytology samples to assist in the diagnosis of PMOL. Briefly, both histopathological and brush cytological samples for 714 subjects from three patient groups were measured: (1) subjects with PMOL who underwent scalpel biopsy as part of the standard of care for microscopic diagnosis, (2) subjects with recently diagnosed malignant lesions, and (3) healthy volunteers without lesions. Only subjects with complete biomarker results were included in the analysis (N=486). Table 2 summarizes the patient characteristics of those subjects included in the analysis.

TABLE 2

Patient characteristics and histopathological diagnoses

| Characteristics and Histopathological Diagnoses | N (%) |
|---|---|
| Total | 486 |
| Sex | |
| Male | 211 (43.4) |
| Female | 275 (56.6) |
| Age | |
| >60 | 165 (34.0) |
| ≤60 | 320 (65.8) |
| Patient Group | |
| Healthy Volunteer | 121 (24.9) |
| Subjects with Previously Diagnosed Malignant Lesion | 36 (7.4) |
| Subject with a Potentially Malignant Lesion | 329 (67.7) |
| Histopathological Diagnosis | |
| Normal | 121 (24.9) |
| Benign | 241 (49.6) |
| Mild Dysplasia | 38 (7.8) |
| Moderate Dysplasia | 12 (2.5) |
| Severe Dysplasia | 9 (1.9) |
| Malignant | 65 (13.4) |

Clinical Protocol

The clinical protocol for this study was published previously (Speight P M et al., 2015 Oct. 1; 120(4):474-82) and is summarized as follows. Patients in group 1 underwent brush sampling of the oral lesion and a brush sampling of the contralateral, clinically normal mucosa. The brush cytology sample was taken immediately before the same lesion underwent a scalpel biopsy. Patients in group 2 underwent brush biopsy of the known cancerous lesion, as well as the contralateral, clinically normal mucosa. For healthy volunteers in group 3, a brush biopsy of normal appearing tissue on the lateral or ventral surface of the tongue and a brush biopsy of normal appearing tissue on the left or right buccal mucosa were taken. Brush biopsy samples were taken using a soft Rovers Orcellex oral cytology brush (Rovers Medical Devices B.V., Oss, The Netherlands). The brush was applied directly to the lesion or control oral mucosa using mild pressure and rotated 360 degrees approximately 10-15 times in the same direction to obtain the cytologic sample.

Cytology-On-a-Chip Protocol

The following methods have been published previously (Abram T J et al., Oral oncology. 2016 Sep. 1; 60:103-11) and are summarized here for convenience. Immediately after brush cytology samples were collected, cells were harvested by vortexing the brush head in minimum essential medium (MEM) culture media, followed by a PBS wash, re-suspension in FBS containing 10% of the cryo-preservative dimethyl-sulfoxide (DMSO), frozen, and stored in a −80 degrees C. freezer.

Prior to processing on the device, patient samples were thawed rapidly in a 37 degrees C. water bath, washed with PBS, and fixed for one hour in 0.5% formaldehyde prepared fresh from a 16% stock solution (Polysciences, Warrington, Pa., #18814-20). After fixation, cells were washed twice in PBS, re-suspended in 150 µL 0.1% PBS with 0.1% BSA (PBSA), and stored at 40 degrees C. until ready to process. Before sample delivery, the cell suspension was diluted in a 20% glycerol/0.1% PBSA solution to improve cell distribution across the membrane and to reduce cell clumping.

Using a custom built manifold connecting external fluidic tubing to the inlet and outlet ports of the microfluidic device, the assembly was positioned on a robotically controlled microscope stage (ProScan II, Prior Scientific, Cambridge, UK) and connected to a peristaltic pump (SciQ 400, Watson Marlow, Wilmington, Mass.) and manually controlled 6-position injector valve (Vici, Valco Instruments, Houston, Tex.). Antibody stock solutions were vortexed for 30 seconds and centrifuged at 14,000 rpm for 5 minutes before preparing working dilutions to avoid precipitates.

All assays contained Phalloidin and DAPI in the secondary antibody cocktail, but each was specific for a single molecular biomarker primary-secondary antibody pair. Working dilutions of antibodies were prepared in 0.1% PBSA with 0.1% Tween-20 (EMD Millipore, Billerica, Mass., #655206). Primary monoclonal antibodies were raised from either mouse (EGFR [Life Technologies, Carlsbad, Calif., #MS-378-P, 10 µg/mL]), rabbit (αvβ6 [Abcam, Cambridge, Mass., #Ab124968, 6 µg/mL], Ki67 [Abcam #Ab15580, 29 µg/mL], and MCM2 [Abcam #Ab108935, 10 µg/mL]), or goat (CD-147 [EMMPRIN] [R&D Systems, Minneapolis, Minn., #AF972, 20 µg/mL]. AlexaFluor-488 conjugated secondary antibodies were specific for F (ab')$_2$ fragments of mouse IgG (Life Technologies #A11017, 20 µg/mL for EFGR), rabbit IgG (Life Technologies #A11070, 50 μg/mL for αvβ6, 64 μg/mL for Ki67, and 23.5 μg/mL for MCM2), or goat IgG (Life Technologies #A11078, 40 μg/mL for CD147). A working concentration of 0.33 μM was used for Phalloidin-AlexaFluor-647 (Life Technologies #A22287) and 5 μM for DAPI (Life Technologies #D3571).

In summary, the lab-on-a-chip sample processing was comprised of the following steps: 1) the device was primed with PBS at a flow rate of 735 μL/min for 2 minutes, 2) the cell suspension in 20% glycerol/0.1% PBSA was delivered at 1.5 mL/min for 2 minutes, 3) cells were washed with PBS at 1 mL/min for 2.5 min, 4) the primary antibody solution was delivered through a 0.2 μm PVDF syringe filter at 250 μL/min for 2.5 min, 5) a wash step similar to step 3 was performed, 6) the secondary antibody solution was delivered under the same conditions as step 4, 7) a final wash step was performed, and 8) automated image capture was performed.

Sample Digitization

More complete details on cytology sample digitization and a complete list of intensity and morphological parameters are previously described (Abram T J et al., Oral oncology. 2016 Sep. 1; 60:103-11). Images were recorded with a motorized reflected fluorescence microscope (Olympus BX-RFAA) equipped with a CCD camera (Hamamatsu ORCA-03G) through a 10× objective (10×/0.30NA UPlanFl, Olympus). A total of 25 unique fields of view (FOVs) repeated for 3 different z-focal planes were automatically captured across a 20 mm$^2$ area using a robotic x-y-z microscope stage. Due to the complex three-dimensional morphology of oral squamous cells, multiple z-focal planes were captured and subsequently combined into a single, enhanced depth-of-field image to simplify the multispectral detection of the three fluorescent labels using ImageJ "stack focuser".

Combinations of custom macros and the open-source image analysis tools ImageJ (Schneider C A et al., Nat Meth 9 (7): 671-675) and Cell Profiler (Carpenter A E et al., Genome biology. 2006 April; 7(10):R100) were developed to automatically detect individual cells and define their nuclear and cytoplasmic boundaries as individual regions of interest (ROI). These ROIs were used to obtain intensity measurements associated with the three spectral channels and were used to define morphometric parameters. The DAPI and Phalloidin molecular labels served primarily to assist in the automated segmentation of individual nuclei and cytoplasm, respectively.

Cell Identification Model Training and Validation

A cell phenotype classification model was explored for its ability to discriminate and quantitate the frequency and distributions of four cell phenotypes: Type 1: cells presenting as polygonal in shape with a low nuclear-cytoplasmic ratio (NC ratio) which represent mature squamous epithelial cells; Type 2: cells presenting as small round cells representing immature parabasal cells; Type 3: cells presenting as mononuclear leukocytes; Type 4: cells represented by lone (naked) nuclei without cell membrane and cytoplasm. To recognize these cell types, a machine learning algorithm was trained on 144 cellular/nuclear features from single-cell analyses, including morphological and intensity-based measurements. Prior to model development, principal component analysis (PCA) was performed on the training set. The PCA method is an unsupervised statistical learning technique for exploratory data analysis which improves data visualization by reducing the dimensionality of complex datasets (Jolliffe I. Principal component analysis. 2nd ed. New York: Springer; 2011) and has been used for phenotypic identification in flow cytometric data (Lugli E et al., Cytometry Part A: The Journal of the International Society for Analytical Cytology. 2007 May; 71(5):334-44). Detailed methods for the training and validation of the cell identification model are provided below.

A training set was manually compiled by randomly selecting and labeling cells, resulting in approximately 100-200 single-cell objects for each of the four cell types. All features were log-normalized and standardized for zero mean and unit variance. Principal component analysis (PCA) was performed on the training set, and a scatterplot of the first two principal components was generated to visualize the internal data structure and variance. A k-nearest neighbors (k-NN) classifier was trained on the standardized features using 10-fold cross-validation and configured to find the nearest 7 neighbors in feature space (Euclidean distance). Cross-validated predicted responses by the k-NN classifier were recorded, and accuracy was reported for the overall cross-validation set and individually for each of the four cell types. k-NN model responses with 4 or less out of 7 similar neighbors were labelled "unknown" type, and cross-validated accuracy was reported for the overall training set after accounting for unknown object types.

The cell type classification model was retrained on the entire training dataset, and this final model was applied to the study population and averaged across each of the six molecular biomarker assays. Results are presented for only subjects with evaluable data for all biomarker measurements (N=486). Boxplots were generated to show the distributions of cell phenotypes across 4 diagnostic categories as follows: 121 normal/non-neoplastic, 241 benign, 59 dysplasia, and 65 malignant. Median values of cell phenotypes were compared for all lesion determinations using a two-sided Wilcoxon rank sum test at a significance level of p=0.05. Cell phenotype frequencies and distributions for each subject were retained for use in clinical algorithm development.

The same cell type identification model development process was completed on recently developed integrated instrument, cartridges, and cloud-based analysis tools. Images of benign and malignant lesions were collected with this cloud POC cytology platform, and cell phenotype labels were overlaid on each recognized cell object.

Numerical Index and Diagnostic Models for Assessing PMOL

A numerical index was developed for the purpose of discriminating benign vs. dysplasia/malignant lesions (OED-spectrum model 2|3).

The analysis of dichotomous outcomes with mutually exclusive levels is common in clinical diagnostics, and logistic regression is regarded as the standard method of analysis for these situations attributed to its probabilistic interpretation and ability to function as a dichotomous classifier. Clinical data are often challenged by high-dimensionality and highly correlated predictors that may generate model coefficients with high variance. For these situations, a size penalty as implemented by the lasso technique may be applied to shrink the effect sizes and reduce coefficient variability. Additionally, the lasso technique performs automatic parameter selection by eliminating predictors with less importance. In high-dimensional data sets, reducing the set of predictors often leads to better prediction performance and generalizability and has shown improvements over manual stepwise selection methods. This lasso logistic regression model is suited to our platform because it is inherently more intuitive than previous methods which consider hundreds of measurements from cytology that are difficult to interpret.

Briefly, subjects were dichotomized into "case" and "non-case" outcomes according to their lesion determination (non-case for benign lesions and case for [mild, moderate, severe] dysplasia and malignant lesions). Due to relatively few numbers of moderate and severe dysplasia patients (total of 21), these lesion determinations were combined.

A lasso logistic regression approach was used to prevent overfitting, reduce coefficient variability, and retain a sparse model with improved generalizability and interpretability. Subjects were dichotomized into "case" and "non-case" outcomes according to their lesion determination (non-case for benign lesions and case for [mild, moderate, severe] dysplasia and malignant lesions). Only subjects with evaluable data for all biomarker measurements and PMOL status were considered (N=365). Algorithm results were recorded for 241 benign lesion and 124 dysplasia and malignant lesion subjects.

Lasso logistic regression was selected for its ability to reduce the number of predictors in high-dimensional data-sets to improve prediction performance and generalizability (Hosmer D W, Lemeshow S. Applied Logistic Regression. 2nd ed. New York: John Wiley & Sons, Inc.; 2004; LaValley M P, Circulation. 2008 May 6; 117(18):2395-9; Hastie T et al., Springer Science & Business Media; 2009 Aug. 26; Wang D et al., Statistics in medicine. 2004 Nov. 30; 23(22): 3451-67). Non-zero lasso logistic regression coefficients were retained for the following predictors: percentage of non-mature squamous cells, percentage of small round cells, percentage of leukocytes, age, sex, smoking pack years, lesion major axis diameter, clinical impression of lichen planus, and lesion color (red, white, or red/white).

Diagnostic performance was characterized by area under the curve (AUC), sensitivity, and specificity. The results from six molecular biomarker assays on the POCOCT system were pooled to obtain final estimates. A receiver operating characteristic (ROC) curve was plotted for the cross-validated test set. Non-zero lasso logistic regression coefficients were retained for the following predictors: percentage of non-mature squamous cells, percentage of small round cells, percentage of leukocytes, age, sex, smoking pack years, lesion major axis diameter, clinical impression of lichen planus, and lesion color (red, white, or red/white) (see Table 3). Boxplots of cross-validated algorithm results were generated for the test set responses for benign, mild dysplasia, moderate/severe dysplasia, and malignant lesions. Median numerical indices were compared for each diagnostic classification using a two-sided Wilcoxon rank sum test at a significance level of p=0.05. Internal calibration was performed by sorting and grouping the predicted responses (i.e., numerical index) into deciles and measuring the observed proportions of dysplasia/malignant lesions in each decile. The Hosmer-Lemeshow goodness of fit statistic was used to assess the model fit (Hosmer D W, Lemeshow S. Applied Logistic Regression. 2nd ed. New York: John Wiley & Sons, Inc.; 2004).

Following this same method, diagnostic algorithms for mild vs. moderate dysplasia (OED-spectrum model 3|4), low vs. high risk (4|4), moderate vs. severe dysplasia (4|5), healthy control (no lesion) vs. malignant (0|6), and benign vs. malignant (2|6) were also developed, and AUC, sensitivity, and specificity were reported as mean and 95% confidence interval values for the cross-validated test set.

TABLE 3

Predictor definitions

| Abbreviation | Reference | Details |
| --- | --- | --- |
| 1-% TYPE 1 | percentage of non-mature squamous cells | 1-(number of mature squamous cells/total cells), where 'total cells' is the number of cells Types 1-3 |
| % TYPE 2 | percentage of small round cells | number of small round cells/total cells, where 'total cells' is the number of cells Types 1-3 |
| % TYPE 3 | percentage of leukocytes | number of leukocytes/total cells, where 'total cells' is the number of cells Types 1-3 |
| AGE | age | age in years |
| SEX | sex | male = 1, female = 0 |
| PACKYR | calculated pack years | average cigarettes smoked per day times years smoked divided by 20 |
| LSIZEMAX | lesion size in maximum dimension | lesion diameter along the long axis in mm |
| LICHENFN | clinical impression of lichen planus | binary measure completed by clinician at time of brush cytology sample collection indicating the presence ("1") or absence ("0") of the clinical features of lichen planus |
| LESIONCOLOR | lesion color (red, white, or red/white) | variable indicating lesion color; white = 0, red = 1, red and white = 2 |

Cytopathology Software

Measurements of individual cells, such as morphometric appearance and biomarker staining intensity, were recorded using the open-source software CellProfiler (Carpenter A E et al., Genome biology. 2006 April; 7(10):R100). All model development and data analyses were completed with MATLAB R2017b (MathWorks, Natick, Mass., USA) software. A graphical user interface for visualizing cytopathology results was developed in MATLAB R2017b. The results summary report tool was developed with Python 3.6.3. Fig.s of the cytopathology software interface and results summary were compiled from a test on the integrated POCOCT instrument.

Level of Integration

Data originating from our 999-patient NIH Grand Opportunity (GO) study and used in the cell identification and diagnostic models were collected using non-integrated cytology-on-a-chip flow cell prototypes, syringe pumps, research microscope stations, and a collection of commercial and open-source software packages (Abram T J et al., Oral oncology. 2016 Sep. 1; 60:103-11). More recently, the cytology-on-a-chip technology is integrated into a POC device comprising integrated instrument, microfluidic cartridges with on-board blister packs, and dedicated software. Likewise, sample processing steps have been significantly reduced. Cell identification and diagnostic models developed on the non-integrated platform were translated to the POC instrument, and software screenshots and results reports presented here were completed with this integrated POC platform.

The results of the experiments are now described.

Cell Identification Model

Figure 1:
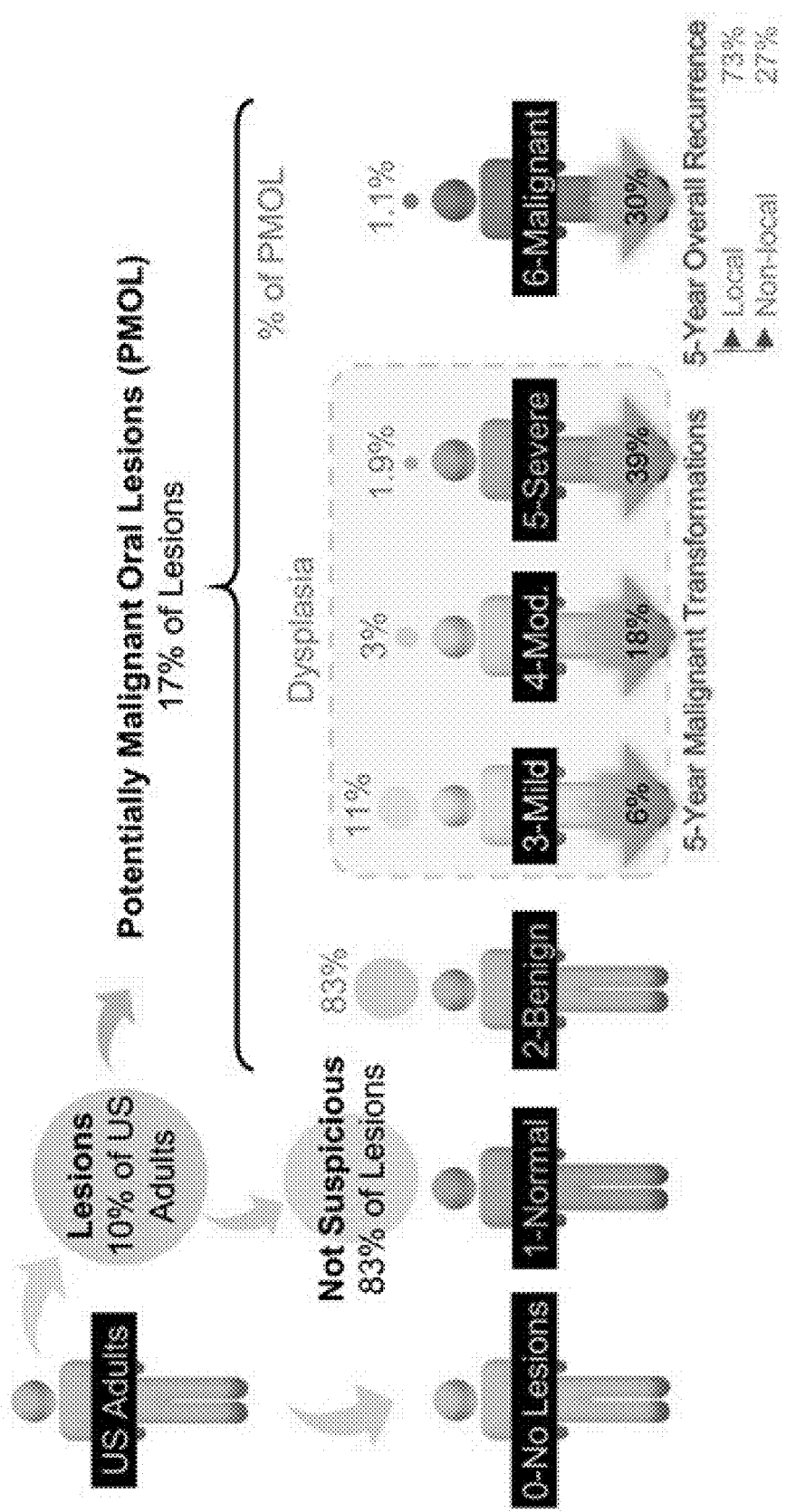
FIG. 1 depicts the diagnostic categories for oral cancer and dysplasia based on WHO classification with 5-year malignant transformations and 5-year cancer recurrence rates. While 10% of US adults may present to their dentist for a routine care visit with an abnormal oral cavity lesion, about 83% of these lesions are diagnosed clinically as having no malignant potential, and 17% have unknown significance and meet the clinical criteria for PMOL. About 17% of PMOLs are histopathologically diagnosed with OED or OSCC. OED is about 15 times more common than OSCC, yet only a fraction of patients with dysplastic PMOLs undergo malignant transformation.

A cell identification tool to assist in the accurate and precise estimation of histopathological endpoints for the entire spectrum of OED and OSCC was developed. FIG. 1 shows the diagnostic categories and rates for oral cancer and dysplasia based on WHO classification (El-Naggar A K et al., WHO classification of tumours of the head and neck. 4th ed. Lyon: IARC Press; 2017) found during mass screening (Bouquot J E et al., The Journal of the American Dental Association. 1986 Jan. 1; 112(1):50-7), showing 5-year malignant transformations (Sperandio M et al., Cancer Prevention Research. 2013 Aug. 1; 6(8):822-31) and 5-year cancer recurrence (Brands M T et al., Cancer medicine. 2019 Sep. 1). The literature presents a range of 5-year transformation and recurrence rates, and the ones listed here are representative of those reported previously.[30]

Figure 3A:
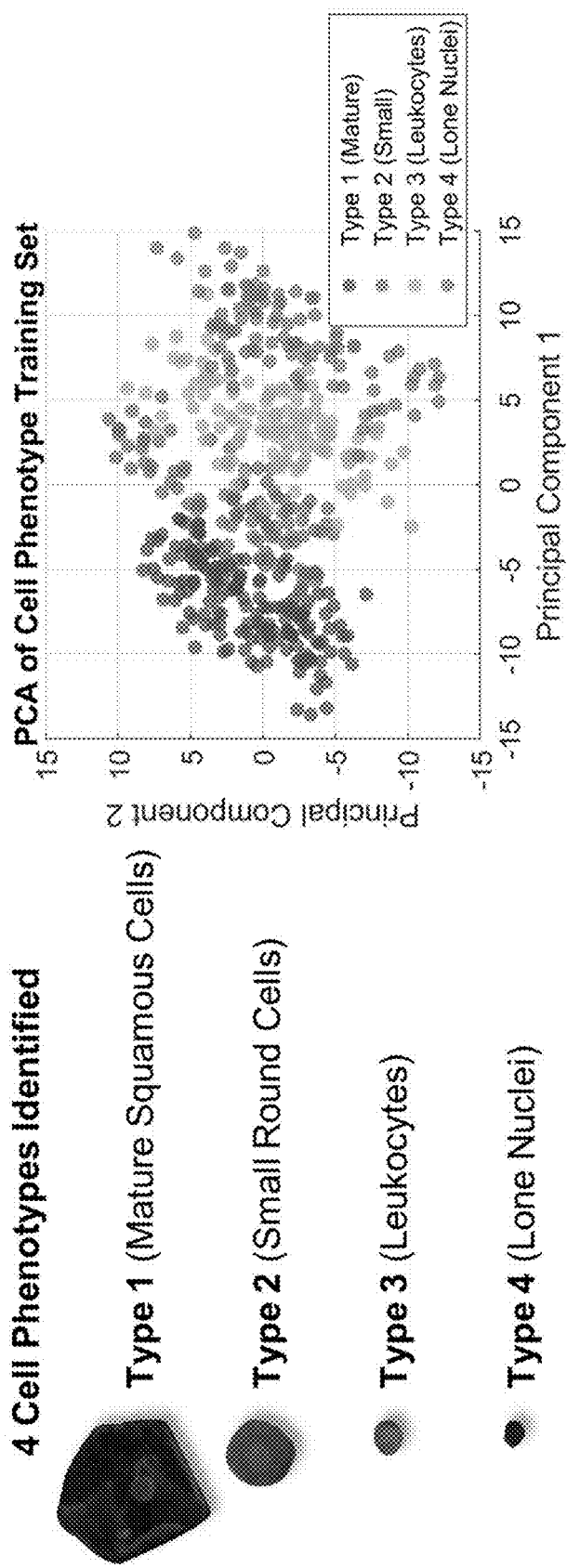
FIG. 3A-FIG. 3C depicts the results of a cell type identification model, which was developed to automatically classify cell Types 1-4.

The POCOCT platform (FIG. 2) comprises a minimally invasive brush cytology test kit, disposable assay cartridge, instrument, clinical algorithms, and cloud-based software services to automate the quantification and analysis of cellular and molecular signatures of dysplasia and OSCC. The cell identification tool automatically classified four distinct cell phenotypes (FIG. 3A). Type 1 'mature squamous' or 'mature keratinocytes' were broad/flat cells, approximately 50-100 μm in diameter, had a low NC ratio, and demonstrated a relatively low cytoplasm staining intensity (Phalloidin-Alexa Fluor® 647). Type 2 'small round' cells were small (12-30 μm in diameter) highly circular cells with high NC ratio and a brightly stained cytoplasm representing immature basaloid keratinocytes. Type 3 'leukocytes' appeared as small, brightly stained pink objects 6-23 μm in diameter representing mononuclear leukocytes. Type 4 'lone nuclei' represented by lone or naked nuclei without a cytoplasm appeared as brightly stained blue objects approximately 5-12 μm in diameter.

The PCA scatter plot of the first two principal components revealed a glimpse of the internal data structure and variance (FIG. 3A). Here, populations according to each cell type were clearly observed. Further, over 90% of the variance was explained by the first 20 principal components from a total of 144, with 30% and 14% variance explained in the first and second principal components, respectively. Despite Types 2 and 3 having similar cytomorphology, the features with the largest association with the first principal component were NC ratio and mean cytoplasm intensity, suggesting that cell size and cellular actin content/distribution play a dominant role in explaining the variance among these cell phenotypes.

Figure 3B:
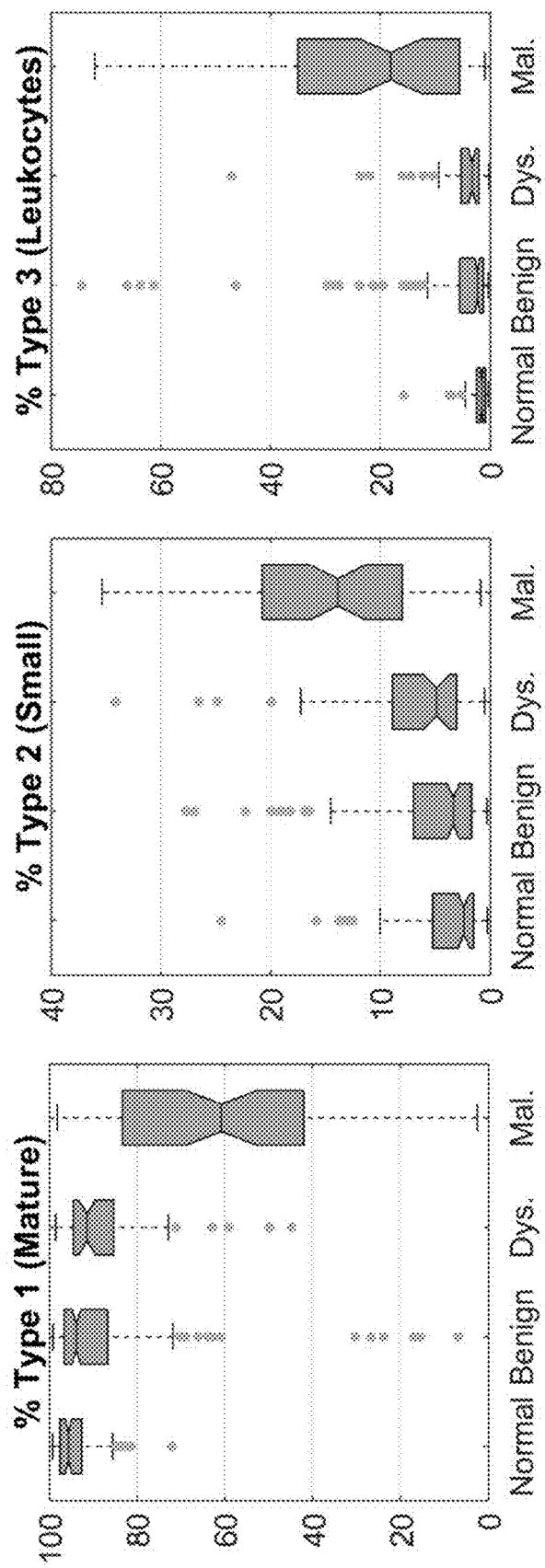

The cross-validated k-nearest neighbors (k-NN) algorithm resulted in overall accuracy of 96.9% and accuracy of 100%, 90.1%, 96.0%, and 99.0% for Types 1 (mature), 2 (small), 3 (leukocytes), and 4 (lone nuclei), respectively. An additional label ('unknown') was added for cells that had four or less similar neighbors. After accounting for this 'unknown' cell type, the overall accuracy was 99.3%. When applied to the study population, cell phenotype distributions showed significant differences across all diagnostic categories (FIG. 3B). The proportion of Type 1 (mature) cells decreased with more advanced disease. In contrast, the proportions of Type 2 (small) and Type 3 (leukocytes) cells increased with disease progression. Median values for Type 1 (mature) and Type 2 (small) cells were significantly different between all lesion determinations. For Type 3 (leukocytes), all lesion determinations had significantly different median values except for benign vs. dysplasia (p=0.0539).

Figure 3C:
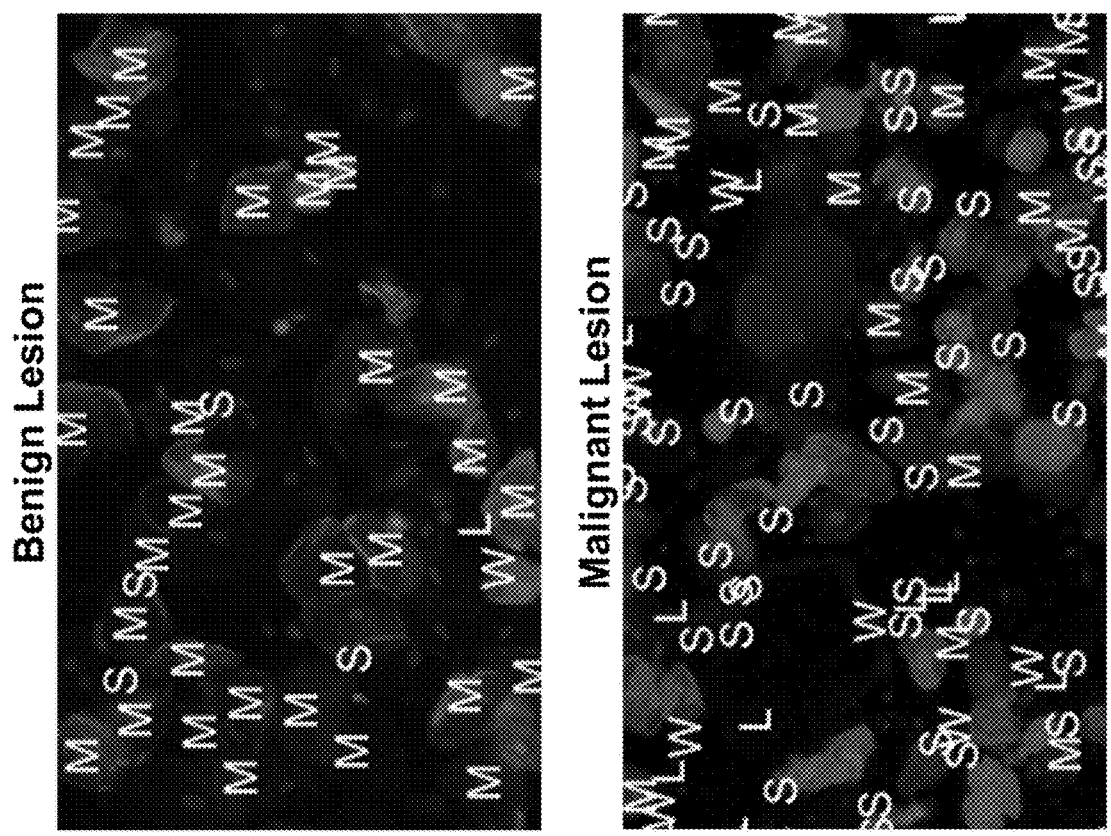

The same cell identification model development process was completed on recently developed integrated instrumentation, cartridges, and cloud-based analysis tools. Images from two samples, one each from benign and malignant lesions, were collected with the POCOCT platform, and cell phenotype labels were overlaid on each recognized cell object (FIG. 3C). Here, the benign lesion sample contained mostly Type 1 (mature) cells, while the malignant sample contained a mixture of primarily Type 2 (small), Type 3 (leukocytes), and Type 4 (lone nuclei).

Numerical Index and Diagnostic Models for Assessing PMOL

Figure 4B:
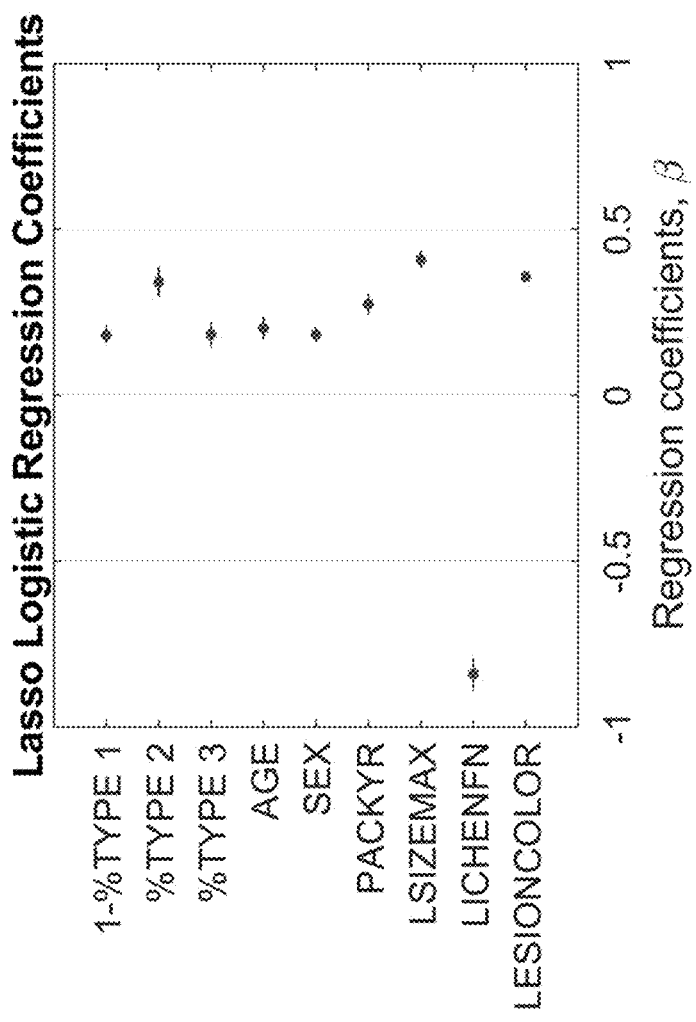
FIG. 4A-FIG. 4D depicts the algorithm results of the dichotomous benign vs. dysplasia/malignant lesion model from 241 benign lesion and 124 dysplasia and malignant lesion subjects for six molecular biomarker assays on the POCOCT system.
Figure 4A:
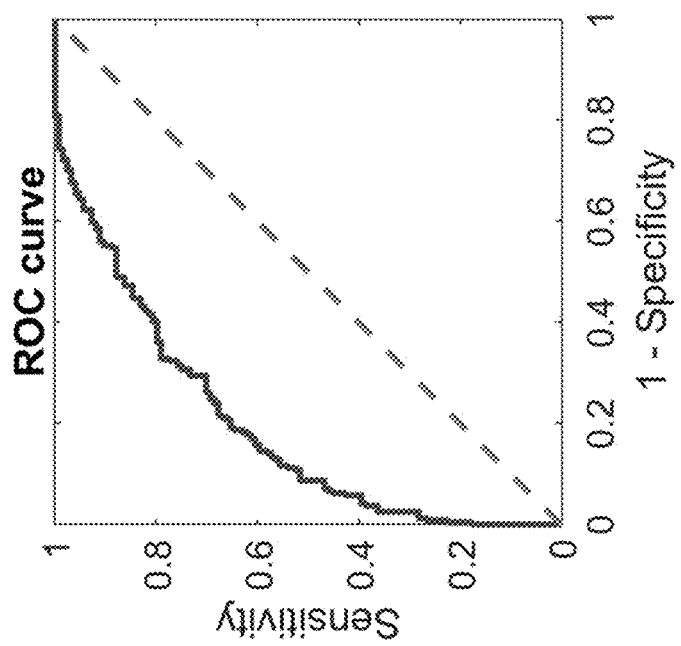
Figure 4D:
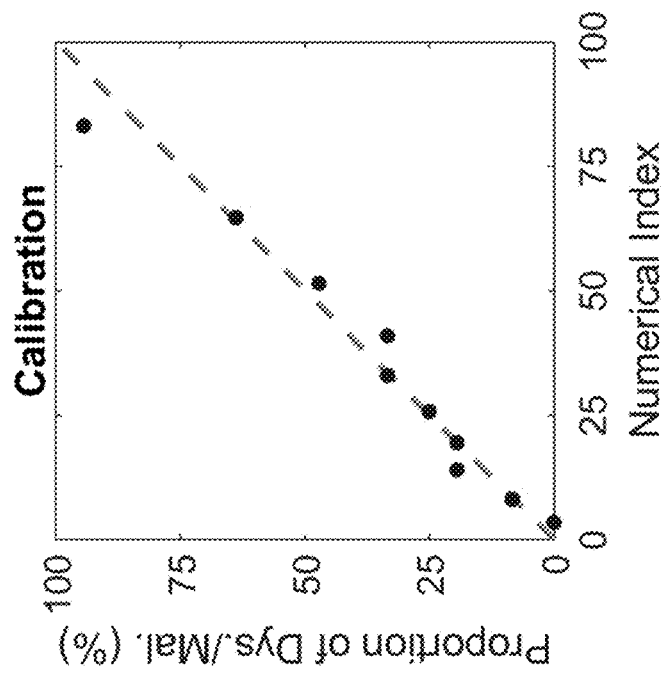
Figure 4C:
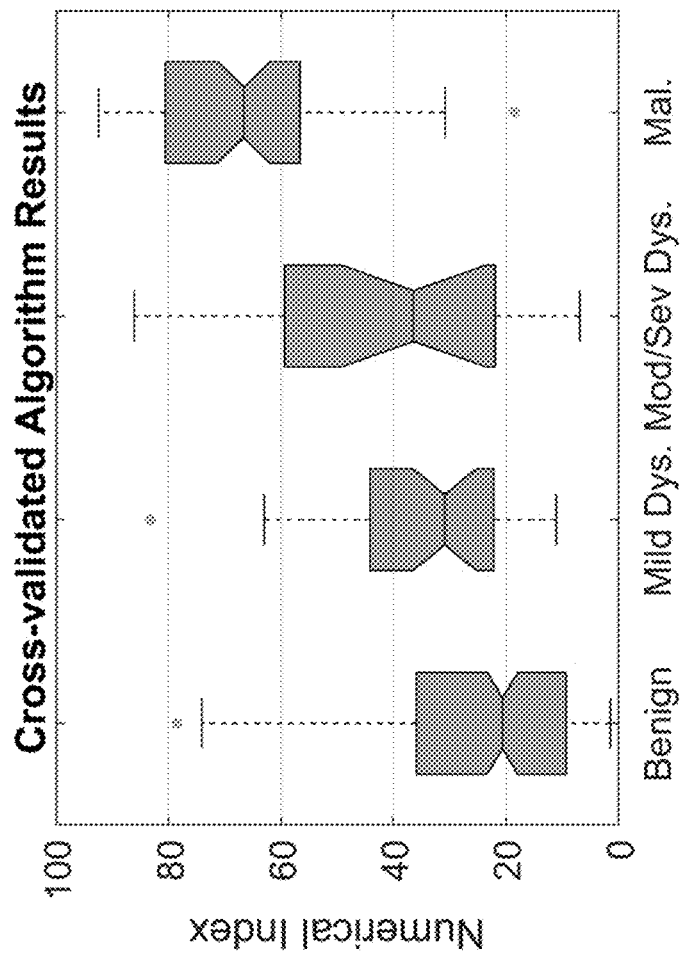

Expanding on this capability, a numerical index for discriminating benign and dysplasia/malignant lesions was developed using the cell phenotypes as predictors. FIG. 4A shows the ROC curve representing discrimination performance of the multivariate model. The numerical index is a score between 0 and 100 that can be interpreted literally as the probability of dysplasia/malignancy. The diagnostic accuracy of the model is defined by the cutoff score that maximizes its AUC (benign vs. dysplasia/malignant numerical index cutoff of 36). Predictors for the model were retained as follows: cell phenotype distributions (Types 1, 2, and 3), age, sex, smoking pack years (i.e., packs per day times years of smoking), lesion size (maximum diameter), clinical impression of lesion as lichen planus, and lesion color (white, red, or both) (FIG. 4B). Minimal differences were observed between training and test error (28% and 27% misclassification rate on the training and test sets, respectively) which suggests no evidence of overfitting. The numerical index showed significant differences between all lesion diagnostic categories studied (p<0.01) except for mild vs. moderate/severe dysplasia (p=0.1519) (FIG. 4C); however, significant differences were observed in a dichotomous model for mild vs. moderate dysplasia (i.e., 314) (p=0.04). Model calibration shows the numerical index relative to the observed proportions of dysplasia/malignant subjects when sorted and grouped into deciles (FIG. 4D). A non-significant result of the Hosmer-Lemeshow goodness of fit test suggests that there is no evidence of a poor fit (p=0.6259).

Figure 5:
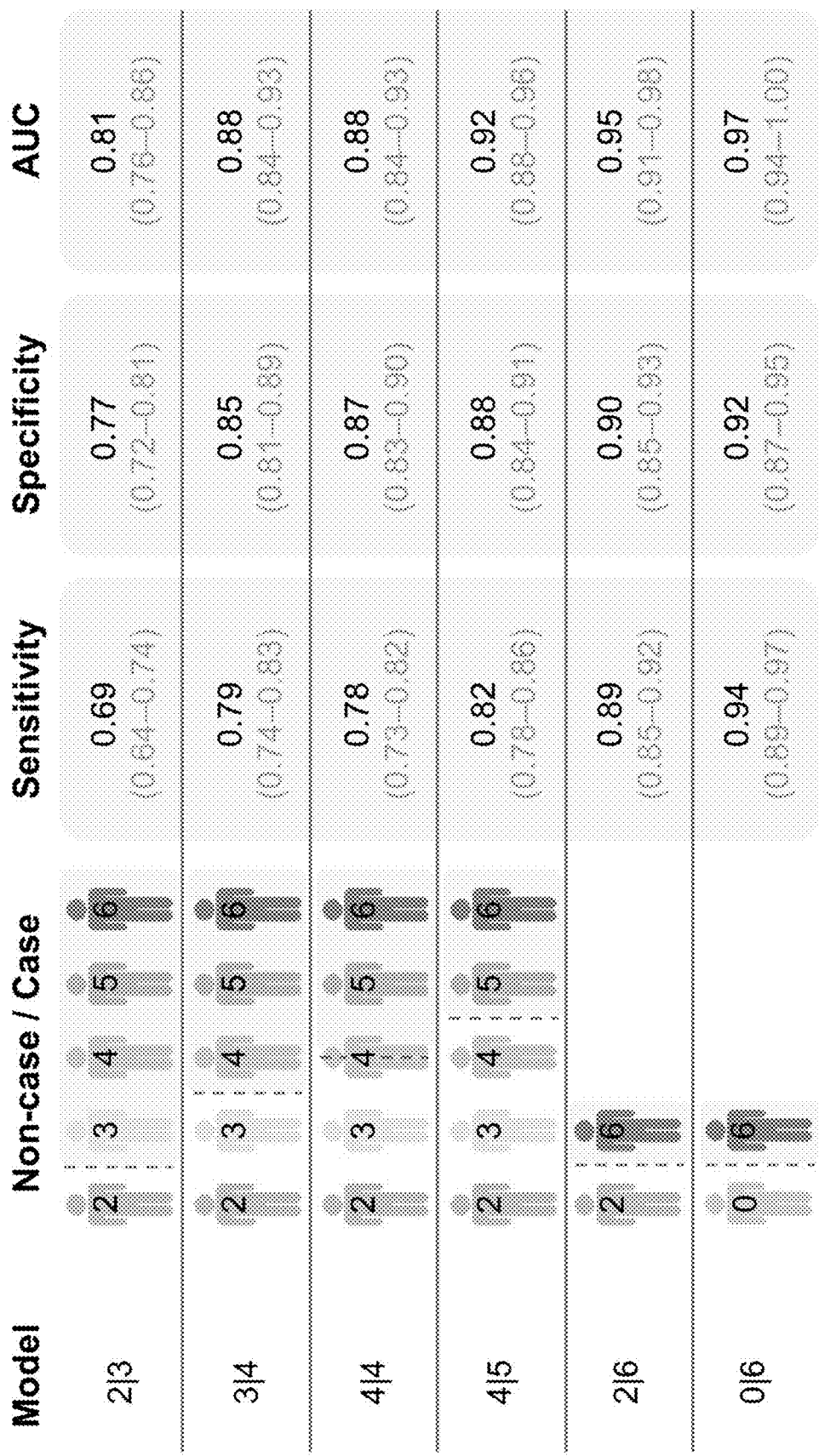
FIG. 5 depicts diagnostic models for the OED spectrum. Results are shown for the cross-validated clinical algorithms for benign vs. dysplasia (2|3), mild vs. moderate dysplasia (3|4), low vs. high risk (4|4), moderate vs. severe dysplasia (4|5), healthy control (no lesion) vs. malignant (0|6), and benign dysplasia vs. malignant (2|6) models. Model responses for each subject were averaged over all biomarker assays to inform diagnostic performance. AUC, sensitivity, and specificity are mean and 95% confidence interval values for the cross-validated test set.
Figure 6A:
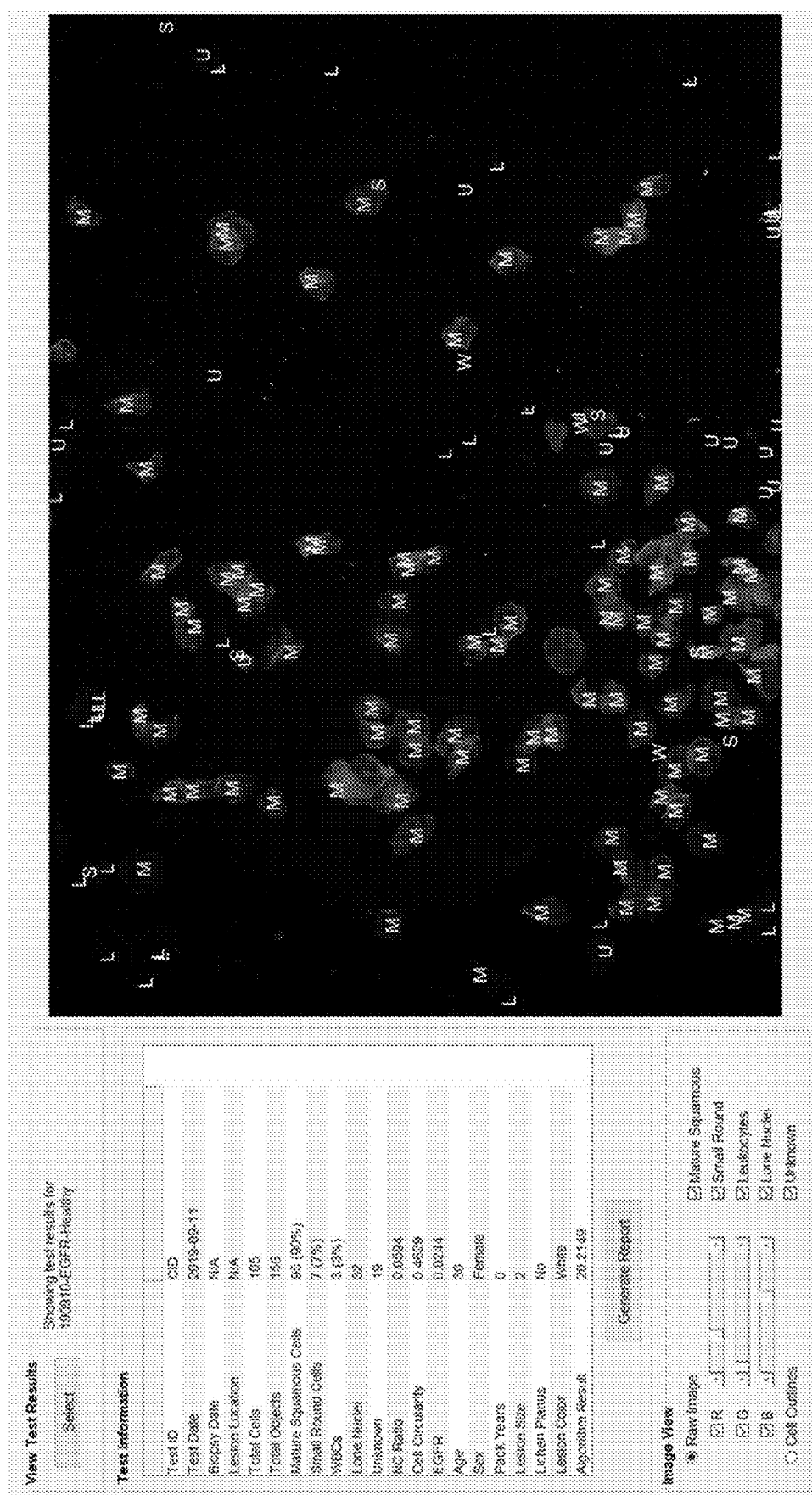
FIG. 6A-FIG. 6C depicts the cytopathology interface tool that provides pathologists with cloud access to test results summaries and detailed data visualizations (FIG. 6A), scatter plots (FIG. 6B), and histograms (FIG. 6C) for over 150 different cytology parameters. With this tool, pathologists can view all cells within the field of view, zoom in for more detail, and isolate individual cells of interest.
Figure 6C:
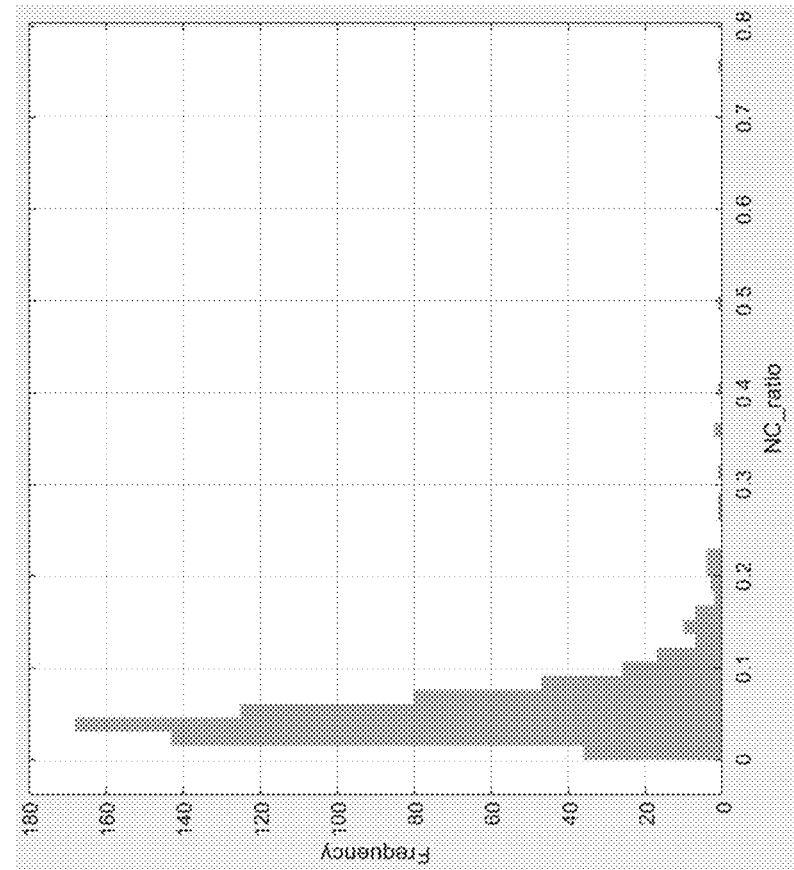
Figure 6B:
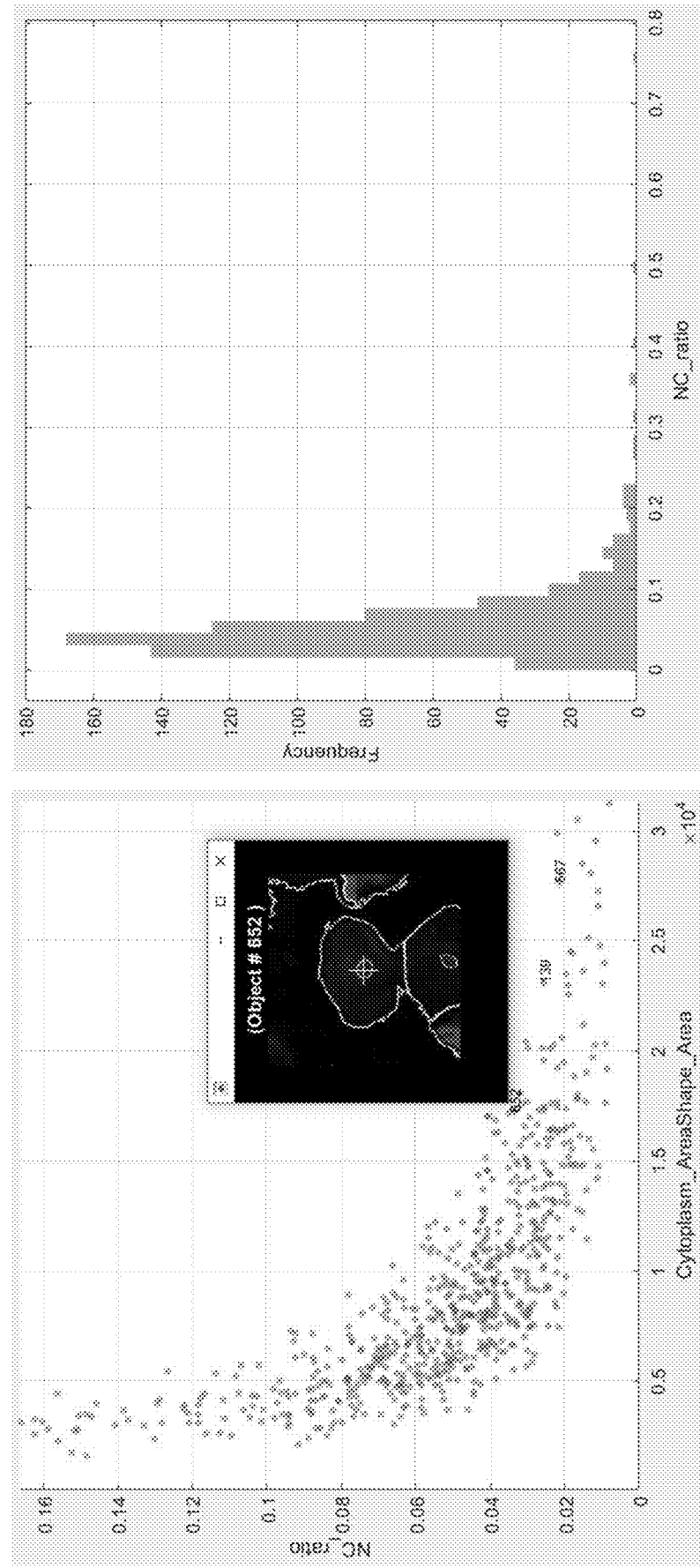

Models were also developed for dichotomous classification across the OED spectrum, and FIG. 5 summarizes the diagnostic performance of these models. The clinical algorithms resulted in AUCs ranging 0.81 (95% CI 0.76-0.86) for benign vs. mild dysplasia (314) to 0.97 (0.94-1.00) for healthy control (no lesion) vs. malignancy (016). While previous work demonstrated AUCs of 0.836 for the binary low vs. high risk (414) split and 0.883 for moderate vs. severe dysplasia (415) (Abram T J et al., Oral oncology. 2016 Sep. 1; 60:103-11), these new optimized models presented here resulted in improved AUCs of 0.88 (0.84-0.93) and 0.92 (0.88-0.96) for the same diagnostic splits, respectively.

Cytopathology Software

A cytopathology interface tool was developed to assist pathologists in reviewing the brush cytology test results, enabling rich content cellular analyses on single- and multi-cell levels (FIG. 6 and FIG. 8-FIG. 19). This interface enables the pathologist users to access data stored and processed on cloud-based services, view results summaries, explore cytology results through data visualization tools, and generate automated oral cytopathology reports (FIG. 7)

which provide the adjunctive referral recommendations and summarize important information from cytology, including total cell count, cell phenotype distributions (Types 1, 2, and 3), and mean values for NC ratio, molecular biomarker fluorescence intensity, and cell circularity. The ability to assess cumulative data on this cloud-based cytopathology platform may improve pathologist decision making (e.g., through learning about their own histopathologic assessment vs. the POCOCT and, ultimately, the surgical pathology).

A Rapid and Simple Brush Cytology Analysis for POC or in a Remote Laboratory Setting This work demonstrates an evolution of the POCOCT technology towards a rapid and simple brush cytology analysis for POC or in a remote laboratory setting. It is demonstrated herein that (1) cell phenotypes can be accurately determined through the automated cytological assay and machine learning approach; (2) significant differences in cell phenotype distributions across diagnostic categories are found in three phenotypes (Types 1, 2, and 3); and (3) these cell phenotypes are valuable predictors for distinguishing lesion diagnostic categories in a multivariate lasso logistic regression model. The compilation of these results suggests that the observed cellular phenotypic variations within cytological samples are equated with disease severity and, thus, may be useful in the evaluation of PMOLs. Although cell phenotyping can be completed by a pathologist by manually identifying cells in a cytological sample, this is a lengthy process subject to human errors. Providing a means to automate metrics, such as the distributions of cell phenotypes, may increase adoption of this POCOCT approach through a cytopathology service and allow for pathologists to complete more efficient and more effective recommendations.

The optimized numerical index for evaluating PMOLs developed here represents a simple, practical, and effective approach that is directly applicable to clinical implementation and interpretation. While previous models relied on complicated high-dimensional cytological parameters, the classification and quantitation of cell phenotypes greatly simplifies the predictive algorithm and its interpretation, substantially improves performance for diagnostic splits relative to these earlier efforts (Abram T J et al., Oral oncology. 2016 Sep. 1; 60:103-11; Abram T J et al., Oral oncology. 2019 May 1; 92:6-11), and supports the translation of research methodologies from laboratory-based microscopy stations to an integrated POC instrument. With a total of 9 predictors, the practical model developed here represents a sparse solution (i.e., reduction of over 150 variables to 9) with greater potential generalizability without sacrificing any diagnostic performance. Further, excellent model calibration performance and significant differences between the diagnostic endpoints demonstrates strong potential for the numerical index as a continuous indicator of PMOL risk. While previous work was primarily focused on delivering binary results for referral decisions (Abram T J et al., Oral oncology. 2016 Sep. 1; 60:103-11), this new work involves a cytopathology interface tool, developed to assist pathologists in reviewing the brush cytology test results, and a numerical index, enabling rich content cellular analyses on single- and multi-cell levels. This interface enables the pathologist to access data stored on cloud-based services, view results summaries, explore cytology data through data visualization tools, and generate a report that provides recommendations. Accurate diagnostic models spanning the entire OED spectrum also demonstrate the potential for the POCOCT to be used for multiple applications, such as screening PMOLs in primary care and the surveillance of patients with a history of OED and OSCC in secondary or tertiary care settings.

Although light-based adjuncts offer clinicians a new perspective to view a lesion at the POC, their diagnostic utility remains unproven (Huber M A, Dental Clinics. 2018 Jan. 1; 62(1):59-75). Rashid and Warnakulasuriya reviewed the performance of light-based adjuncts in discriminating low and high risk lesions (VELscope [sensitivity/specificity: 30-100/15-100], ViziLite Plus [0-100/0-78], and Microlux DL [78/71]) and concluded that there is insufficient evidence to validate their efficacy as screening adjuncts (Rashid A et al., Journal of Oral Pathology & Medicine. 2015 May; 44(5):307-28). Despite the numerous adjunctive tests available to assist in the diagnosis of PMOLs today, only cytology shows potential as a surrogate for gold standard histopathology (Lingen M W et al., The Journal of the American Dental Association. 2017 Nov. 1; 148(11):797-813). Several commercial cytopathology services exist today including OralCDx (CDx Diagnostics, Inc.), OralCyte (ClearCyte Diagnostics, Inc.), Cyt ID (Forward Science), and ClearPrep OC (Resolution Biomedical). OralCDx, for example, provides an oral brush sample collection kit for their BrushTest (CDx Diagnostics: The Painless Test for Common Oral Spots https://www.cdxdiagnostics.com/brushtest/. Accessed May 10, 2019). Despite the ease of collection, samples need to be shipped to a commercial laboratory for analysis, resulting in delays between sample collection and test results. Further, the test often returns an ambiguous "atypical" result for which the positive predictive value for dysplasia or carcinoma has been determined to be only 30-40% (Svirsky J A et al., General dentistry. 2002; 50(6):500-3). Additionally, prior studies of cytology adjuncts demonstrated methodological gaps by only performing matched gold-standard histopathology on a subset of lesions with a higher index of suspicion for malignancy, and not for lesions with a lower index of suspicion which are frequently encountered in primary care settings (Sciubba J J, The Journal of the American Dental Association. 1999 Oct. 1; 130(10):1445-57; Poate T W et al., Oral oncology. 2004 Sep. 1; 40(8):829-34). A clinically validated POC cytology service capable of distinguishing the degree of OED in PMOL and stratifying the risk of malignant progression as a numerical index in near real-time would fulfill a significant unmet need mitigating unnecessary referrals to experts, leading to a more efficient process in surveillance clinics and reducing the patient distress related to waiting for test results.

One limitation is that previous studies of the POCOCT, and cytology adjuncts in general, primarily focused on PMOL evaluation in secondary care settings where the prevalence of dysplastic and malignant lesions may be substantially higher than in the primary care. Additionally, while expert clinicians in secondary and tertiary care settings have extensive training and experience in the recognition and risk stratification of PMOLs, primary care clinicians may have difficulty distinguishing PMOLs from normal/non-neoplastic lesions. Thus, the POCOCT technology may potentially have a larger impact in primary care settings where there is a strong need to accurately interrogate the PMOLs detected there and generate a dichotomous outcome to indicate if referral of patients to higher care settings for expert evaluation and possible biopsy is required and if such referral should be urgent.

These studies provide a key step towards the development of new tools that could pave the way for new capabilities in the area of 'precision lesion diagnostics'. Helping to push forward this theme, the utility of temporal changes in numerical index has been demonstrated in a pilot study of Fanconi Anemia (FA) patients (Abram T J et al., Translational oncology. 2018 Apr. 1; 11(2):477-86). These efforts showed strong potential for patient-specific temporal changes in the lesion numerical index to track early signs of disease for this high risk population. Plans are now in place to (1) evaluate the POCOCT's precision lesion diagnostic capabilities through a prospective longitudinal study of malignant transformation and cancer recurrence and (2) move the POCOCT into a clinical trial to assess the POCOCT's diagnostic performance vs. routine care in primary care clinics.

In summary, the utility of a POC-amenable cytology platform that has the potential to screen and monitor oral lesions across the entire diagnostic spectrum of OED has been demonstrated herein. Cell phenotype distributions provided additional information in the assessment of PMOL. Further, a practical model comprised of patient information, lesion characteristics, and cell types from cytology showed similar performance characteristics to more complicated models previously developed. Cytopathology software may assist expert pathologists and non-expert care providers in reviewing and understanding the brush cytology test results. Data visualization tools are developed to provide high content cellular analyses on single- and multi-cell levels with full transparency of test results data for pathologists. Additionally, oral cytopathology results summarize the test's most important predictors through indications of potential lesion progression for care providers and patients. Along with recently developed instrumentation and cartridges, this simple and sensitive system could provide non-invasive triage for PMOLs detected in primary, secondary, and tertiary care settings. Additional details regarding this study and associated methods, materials, and results using the devices, systems, and methods of the present invention can be found in McRae M P et al., Cancer cytopathology. 2020 March; 128(3):207-20, which is incorporated by reference in its entirety.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Example 2

Traditional clinical observations including lesion size and appearance lack sufficient information content to afford reliable early disease detection on a consistent basis. Most prior research methodologies focus on precancerous vs. malignant lesions and do not consider multiple alternative histopathological endpoints, resulting in over optimistic expectations for practical clinical implementation of cytology. New cytology tools for use at the point of care have the potential to gather new precision lesion diagnostic information with a numerical index can provide options for oral lesion management not previously practical.

It is shown herein that data fusion opportunities yield information with new insights into lesion disease risk. For example it is demonstrated herein that nuclear actin outperforms lesion appearance metrics, and that aggregate metrics fused into single diagnostic model yields higher diagnostic accuracy that traditional metrics based on lesion appearance and risk factors. Using the new Point of Care Oral Cytology Tool (POCOCT) models based on data fusion from cellular phenotypes, nuclear size/shape, localization of nuclear actin, there is strong potential for early disease detection. As might be expected earlier disease detection is more difficult than late stage disease (i.e., lower AUCs) and this observation is now clearly established using carefully acquired prospective clinical study across a broad range of data fields. Cell phenotype distributions from cytology are strong predictors of disease, with different cell types being important for early vs. later stage disease (Type 1N+ cells are important for early disease (2|3,4,5,6) while Types 2 and 3 are important for later stage disease (2,3,4|5,6)). Traditional risk factors (e.g., alcohol and tobacco) do not play a dominant role for distinguishing 2|3,4,5,6 or 2,3,4|5,6 but do show statistically significant OR in 2|6, suggesting that conventional risk factors may not be useful in distinguishing OED gradings. Lesion color plays a dominant role in late stage disease but is not useful for the important task of early disease detection and interception. Lichen planus has a strong protective effect in both early and late stage disease prediction.

The POCOCT assay platform (FIG. 2) allows for the analysis of cellular samples obtained from a minimally invasive brush biopsy sample. The cell suspension collected in this manner allow for the simultaneous quantification of cell morphometric data and expression of molecular biomarkers of malignant potential in an automated manner using refined image analysis algorithms based on pattern recognition techniques and advanced statistical methods. This novel approach turns around biopsy results in a matter of minutes as compared to days for traditional pathology methods, thereby making it amenable to POC settings. The POC testing is expected to have tremendous implications in the rapid management of patient disease by enabling dental practitioners and primary care physicians to circumvent the need for multiple referrals and consultations before obtaining assessment of molecular risk of PMOL.

Table 4 depicts the subject characteristics and histopathological diagnoses based on WHO classification (El-Naggar et al., 2017), of those used in these experiments.

TABLE 4

| Characteristics and Histopathological Diagnoses | |
|---|---|
| | N (%) |
| Total | 486 |
| Sex | |
| Male | 211 (43.4) |
| Female | 275 (56.6) |
| Age | |
| ≤60 | 321 (66.0) |
| >60 | 165 (34.0) |
| Tobacco | |
| Never | 213 (43.8) |
| Any Tobacco Use | 273 (56.2) |
| Previous Smokers | 140 (28.8) |
| Current Smokers | 113 (23.3) |
| Average Pack Years in Tobacco Users* | 13.0 (1.8-30.0) |
| Subject Group | |
| Healthy Volunteer | 121 (24.9) |
| Patients with Previously Diagnosed Malignant Lesion | 36 (7.4) |
| Patients with a Potentially Malignant Lesion | 329 (67.7) |

TABLE 4-continued

Characteristics and Histopathological Diagnoses

| | N (%) |
|---|---|
| Histopathological Diagnosis | |
| Normal | 121 (24.9) |
| Benign | 241 (49.6) |
| Mild Dysplasia | 38 (7.8) |
| Moderate Dysplasia | 12 (2.5) |
| Severe Dysplasia | 9 (1.9) |
| Malignant | 65 (13.4) |

Cellular phenotype models were developed to identify five phenotypes (FIG. 20A): Type 1N− ('mature squamous cells with nuclear actin absent'), Type 1N+ ('mature squamous cells with nuclear actin present'), Type 2 ('small round cells'), Type 3 ('leukocytes'), and Type 4 ('lone nuclei'). Line plots (FIG. 20B) show the distribution of Type 1N+ cells out of the total Type 1 cells. Principal component analysis (FIG. 20C, left) shows cellular phenotypes with substantial separation between cellular phenotype labels. Select variables are represented as vectors (black lines) in which the direction and length of each vector indicate how each variable contributes to the first two principal components (PC1 and PC2). The majority of the variance may be explained by cell size (PC1), cytoplasm actin (PC2), and nuclear actin (PC3, see FIG. 21A-FIG. 21B)). Line plots (FIG. 20C, right) show the distributions Types 1N+, 1N−, 2, and 3 (excludes Type 4 objects without cytoplasm) within the study population, representing the predicted mean cell type percentages and 95% CI within each lesion class: normal ('1', n=121), benign ('2', n=241), mild/moderate dysplasia ('3+4', n=50), severe dysplasia and malignant ('5+6', n=74).

Experiments were conducted by performing principal component analysis of cellular identification models for the five phenotypes that were identified: Type 1N− ('mature squamous cells with nuclear actin absent'), Type 1N+('mature squamous cells with nuclear actin present'), Type 2 ('small round cells'), Type 3 ('leukocytes'), and Type 4 ('lone nuclei'). Select variables are represented as vectors (black lines) in which the direction and length of the vector indicate how each variable contributes to the principal components (PC). FIG. 21A and FIG. 21B show PCs 1 vs. 3 and 2 vs. 3, respectively, in which the majority of the variance may be explained by PCs 1-3 which are largely represented by cell size, cytoplasm actin, and nuclear actin, respectively.

Conditional probability plots in distinguishing benign-|mild dysplasia (FIG. 22A) and moderate severe dysplasia patients (FIG. 22B) were prepared. Post-test probabilities are plotted as a function of pre-test probability for patients with positive (solid lines) and negative (dashed lines) indications for clinical risk factors (lesion color, lesion area, smoking), cellular phenotypes (Types 1N−, 1N+, 2, and 3), and the multivariate POCOCT model.

Positive (+) and negative (−) likelihood ratios (LR) for clinical and cytological predictors in distinguishing benign-|mild dysplasia and moderate|severe dysplasia patients are shown in FIG. 23. Further, the univariate (FIG. 24A) and multivariate (FIG. 24B) adjusted odds ratios and 95% confidence of intervals were calculated for distinguishing benign|mild dysplasia and moderate|severe dysplasia patients.

Diagnostic models for the OED spectrum are shown in FIG. 25A through FIG. 25C. Results are shown for the cross-validated dichotomous algorithms for benign|mild dysplasia (2|3,4,5,6), mild|moderate dysplasia (2,3|4,5,6), low vs. high risk (2,3,4L|4H,5,6), moderate|severe dysplasia (2,3,4|5,6), benign vs. malignant (2|6), and healthy control (no lesion) vs. malignant (1|6) models. Model responses for each subject were averaged over all biomarker assays to inform diagnostic performance. AUC, sensitivity, and specificity are means and 95% confidence intervals for the cross-validated test set.

The potential new signatures of oral epithelial dysplasia (OED) and oral squamous cell carcinoma (OSCC) identified through this cytology-on-a-chip and machine learning approach have a reasonable biological association with the disease and have the potential to serve as novel tests for rapid and effective PMOL screening and surveillance of the entire spectrum of OED and OSCC in multiple care settings. Additional details regarding this study and associated methods, materials, and results using the devices, systems, and methods of the present invention can be found in McRae M P et al., Journal of dental research. 2020 Nov. 12:0022034520973162, which is incorporated by reference in its entirety.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating oral disease in a subject comprising:
    identifying at least one cellular phenotype of one or more cells in a sample of the subject;
    determining a cellular phenotype characteristic based upon the identified cellular phenotype of the cells, wherein the cellular phenotype characteristic is a percent of mature squamous cells of the sample that express nuclear actin;
    using the cellular phenotype characteristic to assess a presence or severity of oral disease in the subject, wherein the percent of mature squamous cells of the sample that express nuclear actin ranging between 10% and 30% indicates the presence of oral disease in the subject; and
    treating the subject identified with oral disease with an oral disease treatment, wherein the treatment regimen is selected from the group consisting of chemotherapy, radiation, hormone therapy, surgery, and targeted therapy, and wherein the oral disease is selected from the group consisting of: oral cancer, potentially malignant oral lesion (PMOL), and oral epithelial dysplasia (OED).

2. The method of claim 1, wherein the determining step further comprises one or more cellular phenotype characteristics selected from the group consisting of: percent of mature squamous cells, percent of non-mature squamous cells, percent of small round cells, percent of white blood cells, and percent of lone nuclei.

3. The method of claim 2, wherein the percent of lone nuclei of a sample between 20% to 100% indicates the presence of oral disease in the subject.

4. The method of claim 1, further comprising:
determining one or more morphological characteristics from individual cells of the sample, said morphological characteristics selected from nuclear area, cell area, cell circularity, cell aspect ratio, and cell roundness;
transmitting the one or more morphological characteristics to a computer; and
using the cellular phenotype characteristics and morphological characteristics to assess the severity of oral disease in the subject.

5. The method of claim 1, further comprising:
determining one or more biomarker levels in cells of the sample, said biomarker selected from the group consisting of alpha V beta 6 (AVB6), Epidermal Growth Factor Receptor (EGFR), Ki67, Geminin, Mini Chromosome Maintenance protein (MCM2), beta catenin, EMPPRIN, CD147, Cofilin, Importin 9, Profilin, thymosin-β4, Wiskott-Aldrich syndrome protein (WASp), Arp2/3 complex, and formins;
transmitting the one or more biomarker levels to a computer; and
using the cellular phenotype characteristics and biomarker levels to assess the severity of oral disease in the subject.

6. The method of claim 1, further comprising:
transmitting one or more demographic data of the subject to a computer, said demographic data selected from the group consisting of gender, age, alcohol intake, and smoking status of the subject; and
using the cellular phenotype characteristics and biomarker levels to assess the severity of oral disease in the subject.

7. The method of claim 1, wherein the method allows for the distinguishing between at least: 1) normal, 2) benign lesions, 3) mild dysplasia, 4) moderate dysplasia, 5) severe dysplasia, and 6) carcinoma in situ/malignant lesion.

8. The method of claim 1, further comprising calculating a risk score based upon the cellular phenotype characteristics.

9. The method of claim 7, further comprising displaying the risk score on an output device.

10. The method of claim 7, wherein said calculation is based on artificial neural nets, logistic regression, linear discriminate analysis, or random forests.

11. The method of claim 1, further comprising transmitting the one or more cellular phenotype characteristics to a remote processor to be assessed by a pathologist.

12. The method of claim 1, further comprising the steps of:
identifying at least one cellular phenotype of one or more cells in a second sample of the subject;
determining a second cellular phenotype characteristic that is a percent of mature squamous cells of the second sample that express nuclear actin based upon the identified cellular phenotype of the cells; and
using the second cellular phenotype characteristic to assess the efficacy of the administered disease treatment regimen.

* * * * *

UNITED STATES PATENT AND TRADEMARK OFFICE
CERTIFICATE OF CORRECTION

| | | |
|---|---|---|
| PATENT NO. | : 12,235,272 B2 | Page 1 of 1 |
| APPLICATION NO. | : 17/147681 | |
| DATED | : February 25, 2025 | |
| INVENTOR(S) | : John T. McDevitt and Michael P. McRae | |

It is certified that error appears in the above-identified patent and that said Letters Patent is hereby corrected as shown below:

In the Specification

On Column 1, Lines 12-19, please replace the paragraph entitled "STATEMENT REGARDING FEDERALLY SPONSORED RESEARCH OR DEVELOPMENT" with the following paragraph:
-- STATEMENT REGARDING FEDERALLY SPONSORED RESEARCH OR DEVELOPMENT
This invention was made with government support under DE025798, and DE020785 awarded by the National Institutes of Health. The government has certain rights in the invention. --

Signed and Sealed this
First Day of April, 2025

Coke Morgan Stewart
*Acting Director of the United States Patent and Trademark Office*